US008388509B2

(12) United States Patent
Hegg et al.

(10) Patent No.: US 8,388,509 B2
(45) **Date of Patent: *Mar. 5, 2013**

(54) SYSTEMS, DEVICES, AND METHODS INCLUDING PARAMAGNETIC OSCILLATION, ROTATION, AND TRANSLATION OF HEMOZOIN ASYMMETRIC NANOPARTICLES IN RESPONSE TO DARK-FIELD OR RHEINBERG DETECTION OF THE PRESENCE OF HEMOZOIN

(75) Inventors: Michael C. Hegg, Seattle, WA (US); Matthew P. Horning, Seattle, WA (US); Jordin T. Kare, Seattle, WA (US); Nathan P. Myhrvold, Bellevue, WA (US); Clarence T. Tegreene, Bellevue, WA (US); Benjamin K. Wilson, Kirkland, WA (US); Lowell L. Wood, Jr., Bellevue, WA (US)

(73) Assignee: Tokitae LLC

( * ) Notice: Subject to any disclaimer, the term of this patent is extended or adjusted under 35 U.S.C. 154(b) by 504 days.

This patent is subject to a terminal disclaimer.

(21) Appl. No.: 12/658,589

(22) Filed: Feb. 10, 2010

(65) Prior Publication Data

US 2010/0222662 A1 Sep. 2, 2010

Related U.S. Application Data

(63) Continuation-in-part of application No. 12/001,765, filed on Dec. 11, 2007, and a continuation-in-part of application No. 12/658,619, filed on Feb. 10, 2010, and a continuation-in-part of application No. 12/658,580, filed on Feb. 10, 2010, and a continuation-in-part of application No. 12/658,617, filed on Feb. 10, 2010, and a continuation-in-part of application No. 12/658,638, filed on Feb. 10, 2010, and a continuation-in-part of application No. 12/658,607, filed on Feb. 10, 2010.

(51) Int. Cl.

| | |
|---|---|
| *A61N 2/00* | (2006.01) |
| *A61N 2/02* | (2006.01) |
| *A61N 2/04* | (2006.01) |

(52) U.S. Cl. ........................................................ 600/9

(58) Field of Classification Search ................ 600/9–15
See application file for complete search history.

(56) References Cited

U.S. PATENT DOCUMENTS

| | | | | |
|---|---|---|---|---|
| 4,291,938 | A | 9/1981 | Wagner | |
| 4,585,315 | A | 4/1986 | Sincerbox et al. | |
| 5,123,898 | A | 6/1992 | Liboff et al. | |
| 5,224,922 | A * | 7/1993 | Kurtz | 600/13 |
| 5,734,498 | A * | 3/1998 | Krasieva et al. | 359/387 |
| 6,621,568 | B1 | 9/2003 | Yonezawa | |
| 6,721,583 | B1 | 4/2004 | Durkin et al. | |
| 6,739,342 | B1 * | 5/2004 | Fredriksson et al. | 128/899 |
| 6,961,599 | B2 | 11/2005 | Lambert et al. | |
| 7,388,668 | B2 | 6/2008 | Potma et al. | |
| 7,461,961 | B2 | 12/2008 | Li | |

(Continued)

FOREIGN PATENT DOCUMENTS

| | | | |
|---|---|---|---|
| WO | WO 2008/056171 | A2 | 5/2008 |
| WO | WO 2009/009899 | A1 | 1/2009 |

OTHER PUBLICATIONS

Jamjoom G. Dark-field microscopy for detection of malaria in unstained blood films. Journal of Clinical Microbiology 17(5); p. 717-721, May 1983.*

(Continued)

*Primary Examiner* — Charles A Marmor, II
*Assistant Examiner* — Catherine E Burk

(57) ABSTRACT

Systems, devices, and methods are described for providing a monitor/treatment device configured to, for example, detect hemozoin, as well as to monitor or treat a malarial infection.

10 Claims, 37 Drawing Sheets

U.S. PATENT DOCUMENTS

| | | | |
|---|---|---|---|
| 2001/0034478 | A1* | 10/2001 | Lambert et al. ............... 600/318 |
| 2002/0155630 | A1 | 10/2002 | Iwabuchi |
| 2003/0194589 | A1 | 10/2003 | Pratt et al. |
| 2004/0135998 | A1 | 7/2004 | Chin |
| 2005/0043636 | A1 | 2/2005 | Gaeta et al. |
| 2005/0087601 | A1 | 4/2005 | Gerst, III et al. |
| 2005/0288564 | A1 | 12/2005 | Iuliano |
| 2006/0012778 | A1* | 1/2006 | Vaughnn ..................... 356/237.2 |
| 2006/0169314 | A1 | 8/2006 | Horio et al. |
| 2007/0115461 | A1 | 5/2007 | Fairley et al. |
| 2007/0236785 | A1 | 10/2007 | Matsumoto |
| 2007/0253227 | A1 | 11/2007 | James et al. |
| 2008/0100834 | A1 | 5/2008 | Kung et al. |
| 2008/0297783 | A1 | 12/2008 | Urano et al. |
| 2009/0041808 | A1 | 2/2009 | Akira et al. |
| 2009/0149726 | A1 | 6/2009 | Hyde et al. |
| 2009/0227044 | A1 | 9/2009 | Dosev et al. |
| 2009/0318784 | A1 | 12/2009 | Newman et al. |
| 2010/0120132 | A1* | 5/2010 | Koo ........................... 435/287.2 |
| 2010/0196920 | A1* | 8/2010 | Lee et al. ....................... 435/7.1 |
| 2010/0222662 | A1 | 9/2010 | Hegg et al. |
| 2010/0256467 | A1 | 10/2010 | Hegg et al. |
| 2011/0204257 | A1 | 8/2011 | Wiseman et al. |

OTHER PUBLICATIONS

Henry Lai. Magnetic fields may hold key to malaria treatment, UW researches find. University of Washinton Today. Mar. 30, 2000.*

Newman D. et al. A Magneto-optic route toward the in vivo diagnosis of malaria: preliminary results and preclinical trial data. Biophysical Journal 95, p. 994-1000, Jul. 2008.*

PCT International Search Report; International App. No. PCT/US 11/00259; bearing a date of Jun. 20, 2011; pp. 1-4.

PCT International Search Report; International App. No. PCT/US 2011/000260; bearing at date of Jun. 20, 2011; pp. 1-4.

PCT International Search Report; International App. No. PCT/US2011/001815; Feb. 14, 2012; pp. 1-2.

Andresen et al.; "Infrared Multiphoton Microscopy: Subcellular-Resolved Deep Tissue Imaging"; Science Direct, Current Opinion in Biotechnology; bearing a date of 2009; pp. 1-9; vol. 20; Elsevier Ltd.; could be located at: www.sciencedirect.com.

Arambage et al.; "Research: Malaria Ookinetes Exhibit Multiple Markers for Apoptosis-Like Programmed Cell Death in vitro"; BioMed Central, Parasites & Vectors; bearing a date of 2009; pp. 1-16; vol. 2, No. 32; BioMed Central Ltd.; located at: http://www.parasitesandvectors.com/content/2/1/32.

Bahadur et al.; "Biomaterials and Magnetism"; Sadhana; bearing dates of Jun./Aug. 2003; pp. 639-656; vol. 28, Parts 3 & 4; Printed in India.

Balasubramanian et al.; "Photoacoustic Spectroscopy and its Use in Biology"; Bioscience Reports; bearing a date of 1983; pp. 981-995; vol. 3; The Biochemical Society.

Barcinski et al.; "Apoptosis in Parasites and Parasite-Induced Apoptosis in the Host Immune System: A New Approach to Parasitic Diseases"; Brazilian Journal of Medical and Biological Research; bearing a date of 1999; pp. 395-401; vol. 32, No. 4.

Bélisle et al.; "Sensitive Detection of Malaria Infection by Third Harmonic Generation Imaging"; Biophysical Journal: Biophysical Letters; bearing a date of 2008; pp. L26-L28; The Biophysical Society.

Biagini et al.; "The Digestive Food Vacuole of the Malaria Parasite is a Dynamic Intracellular $Ca^{2+}$ Store"; The Journal of Biological Chemistry; bearing a date of Jul. 25, 2003; pp. 27910-27915; vol. 278, No. 30; The American Society for Biochemistry and Molecular Biology, Inc.; could be located at: www.jbc.org.

Chen et al.; "Epi-Third and Second Harmonic Generation Microscopic Imaging of Abnormal Enamel"; Optics Express; bearing a date of Jul. 21, 2008; pp. 11670-11679; vol. 16, No. 15; OSA.

Chu et al.; "Functional THG Microscopy with Plasmon-Resonance Enhancement in Silver Nanoparticles"; CThPDD7; bearing a date of 2003; pp. 1-2; Optical Society of America.

Clay et al.; "Spectroscopy of Third-Harmonic Generation: Evidence for Resonances in Model Compounds and Ligated Hemoglobin"; J. Opt. Soc. Am. B; bearing a date of May 2006; pp. 932-950; vol. 23, No. 5; Optical Society of America.

Clay et al.; "Ultrafast Third Harmonic Micro-spectroscopy Reveals a Two-Photon Resonance in Human Hemoglobin"; Photonics West; bearing dates of Jan. 22-25, 2006; pp. 1-8; vol. 6108, No. 6108-8.

Cui et al.; "Cytotoxic Effect of Curcumin on Malaria Parasite *Plasmodium falciparum*: Inhibition of Histone Acetylation and Generation of Reactive Oxygen Species"; Antimicrobial Agents and Chemotherapy; bearing a date of Feb. 2007; pp. 488-494; vol. 51, No. 2; American Society for Microbiology.

De Villiers et al.; "Oriented Nucleation of β-Hematin Crystals Induced at Various Interfaces: Relevance to Hemozoin Formation"; Crystal Growth & Design; bearing a date of 2009; pp. 626-632; vol. 9, No. 1; American Chemical Society.

Débarre et al.; "Quantitative Characterization of Biological Liquids for Third-Harmonic Generation Microscopy"; Biophysical Journal; bearing a date of Jan. 2007; pp. 603-612; vol. 92; The Biophysical Society.

Débarre et al.; "Signal Epidetection in Third-Harmonic Generation Microscopy of Turbid Media"; Optics Express; bearing a date of Jul. 9, 2007; pp. 8913-8924; vol. 15, No. 14; OSA.

Ding et al.; "ELF Magnetic Fields Promote $H_2O_2$-Induced Apoptosis and Necrosis and Its Molecular Mechanism"; $3^{rd}$ International EMF Seminar in China: Electromagnetic Fields and Biological Effects; bearing dates of Oct. 13-17, 2003; pp. 114 (plus cover page), Session 8-7.

Egan, Timothy J.; "Physico-Chemical Aspects of Hemozoin (Malaria Pigment) Structure and Formation"; Journal of Inorganic Biochemistry; bearing a date of 2002; pp. 19-26; vol. 91; Elsevier Science Inc.

Feagin et al.; "Effects of Alternating Magnetic Fields on Malaria Parasites"; $3^{rd}$ International EMF Seminar in China: Electromagnetic Fields and Biological Effects; bearing dates of Oct. 13-17, 2003; pp. 116 (and cover page), Session 9-1.

Galanzha et al.; "In vivo, Noninvasive, Label-Free Detection and Eradication of Circulating Metastatic Melanoma Cells Using Two-Color Photoacoustic Flow Cytometry with a Diode Laser"; Cancer Res: Cell, Tumor, and Stem Cell Biology; bearing a date of Oct. 15, 2009; pp. 7926-7934; vol. 69, No. 20; American Association for Cancer Research.

Halpern et al.; "Oxymetry Deep in Tissues with Low-Frequency Electron Paramagnetic Resonance"; PNAS, Physiology; bearing a date of Dec. 20, 1994; pp. 13047-13051; vol. 91, No. 26; JSTOR.

Hothi et al.; "Kinetic Isotope Effects and Ligand Binding in PQQ-Dependent Methanol Dehydrogenase"; Biochem. J.; bearing a date of 2005; pp. 123-133; vol. 388; Biochemical Society.

Mao et al.; "Third Harmonic Generation in Self-Focused Filaments in Liquids"; bearing a date of 2007; pp. 1-5; Optical Society of America.

Mungthin et al.; "Central Role of Hemoglobin Degradation in Mechanisms of Action of 4-Aminoquinolines, Quinoline Methanols, and Phenanthrene Methanols"; Antimicrobial Agents and Chemotherapy; bearing a date of Nov. 1998; pp. 2973-2977; vol. 42, No. 11; American Society for Microbiology.

Newman et al.; "A Magneto-Optic Route Toward the In Vivo Diagnosis of Malaria: Preliminary Results and Preclinical Trial Data"; Biophysical Journal; bearing a date of Jul. 2008; pp. 994-1000; vol. 95; Biophysical Society.

Orjih, Augustine U.; "Heme Polymerase Activity and the Stage Specificity of Antimalarial Action of Chloroquine"; The Journal of Pharmacology and Experimental Therapeutics; bearing a date of Mar. 6, 1997; pp. 108-112; vol. 282, No. 1; The American Society for Pharmacology and Experimental Therapeutics.

Orjih, Augustine U.; "On the Mechanism of Hemozoin Production in Malaria Parasites: Activated Erythrocyte Membranes Promote β-Hematin Synthesis"; Exp Bio Med; bearing a date of 2001; pp. 746-752; vol. 226, No. 8; The Society for Experimental Biology and Medicine.

Oron et al.; "Harmonic Generation with Temporally Focused Ultrashort Pulses"; J. Opt. Soc. Am. B; bearing a date of Dec. 2005; pp. 2660-2663; vol. 22, No. 12; Optical Society of America.

Oron et al.; "Third-Harmonic Generation with Cylindrical Gaussian Beams"; J. Opt. Soc. Am. B; bearing a date of Nov. 2004; pp. 1964-1968; vol. 21, No. 11; Optical Society of America.

Pandey et al.; "Mechanism of Malarial Haem Detoxification Inhibition by Chloroquine"; Biochem. J.; bearing a date of 2001; pp. 333-338; vol. 355; Biochemical Society.

Parroche et al.; "Malaria Hemozoin is Immunologically Inert but Radically Enhances Innate Responses by Presenting Malaria DNA to Toll-Like Receptor 9"; PNAS; bearing a date of Feb. 6, 2007; pp. 1919-1924 (plus cover page); vol. 104, No. 6; The National Academy of Sciences of the USA; located at: www.pnas.org/cgi/doi/10.1073/pnas.0608745104.

Ribaut et al.; "Methodology: Concentration and Purification by Magnetic Separation of the Erythrocytic Stages of all Human *Plasmodium* Species"; BioMed Central, Malaria Journal; bearing a date of Mar. 5, 2008; 5 pages; vol. 7, No. 45; BioMed Central Ltd.

Sheetz et al.; "Ultrafast Optics: Imaging and Manipulating Biological Systems"; Journal of Applied Physics, Applied Physics Reviews-Focused Review; bearing a date of 2009; pp. 051101-1 through 051101-17; vol. 105, No. 051101; American Institute of Physics.

Sienkiewicz et al.; "Multi-Frequency High-Field EPR Study of Iron Centers in Malarial Pigments"; JACS Communications; bearing a date of 2006; pp. 4534-4535; vol. 128; American Chemical Society.

Squier et al.; "Third Harmonic Generation Microscopy"; Optics Express; bearing a date of Oct. 26, 1998; pp. 315-324; vol. 3, No. 9; Optical Society of America.

Tai et al.; "In vivo Optical Biopsy of Hamster Oral Cavity with Epi-Third-Harmonic-Generation Microscopy"; Optics Express; bearing a date of Jun. 26, 2006; pp. 6178-6187; vol. 14, No. 13; Optical Society of America.

Tai et al.; "In vivo Molecular-Resonant Third Harmonic Generation Microscopy of Hemoglobin"; CTuF4.pdf; bearing a date of 2007; pp. 1-2; Optical Society of America.

Tekwani et al.; "Targeting the Hemozoin Synthesis Pathway for New Antimalarial Drug Discovery: Technologies for In Vitro β-Hematin Formation Assay"; Combinatorial Chemistry & High Throughput Screening; bearing a date of 2005; pp. 63-79; vol. 8; Bentham Science Publishers Ltd.

Wang et al.; "Evaluation of a Multi-Wavelength Reflectance System for Determination of Tissue Optical Properties in the UVA-VIS"; CFC5.pdf; bearing a date of 2007; pp. 1-2; Optical Society of America.

Yelin et al.; "Third-Harmonic Microscopy with a Titanium-Sapphire Laser"; Applied Physics B, Lasers and Optics; bearing a date of 2002; pp. S97-S101; vol. 74; Springer-Verlag.

Yelin et al.; "Laser Scanning Third-Harmonic-Generation Microscopy in Biology"; Optics Express; bearing a date of Oct. 11, 1999; pp. 169-175; vol. 5, No. 8; Optical Society of America.

Zheng et al.; "Multichannel Multiphoton Imaging of Metal Oxides Particles in Biological System"; Proceeding of SPIE; bearing a date of 2004; 9 pages; Paper 5323-55.

Zimmerman et al.; "Diagnosis of Malaria by Magnetic Deposition Microscopy"; Am. J. Trop. Med. Hyg.; bearing a date of 2006; pp. 568-572; vol. 74, No. 4; The American Society of Tropical Medicine and Hygiene.

Zoueu et al.; "Optical Microscope Based on Multispectral Imaging Applied to Plasmodium Diagnosis"; Journal of Applied Sciences; bearing a date of 2008; pp. 2711-2717; vol. 8, No. 15; Asian Network for Scientific Information.

Lamikanra et al.; "Hemozoin (Malaria Pigment) Directly Promotes Apoptosis of Erythroid Precursors"; PLos One, Open Access; bearing a date of Nov. 6, 2009; pp. 1-12; vol. 4, Issue 12, No. e8446; Lamikanra et al.

Lyke et al., "Association of Intraleukocytic Plasmodium Falciparum Malaria Pigment with Disease Severity, Clinical Manifestations, and Prognosis in Severe Malaria"; Am. J. Trop. Med. Hyg.; bearing a date of 2003; pp. 253-259; vol. 69, No. 3; The American Society of Tropical Medicine and Hygiene.

* cited by examiner

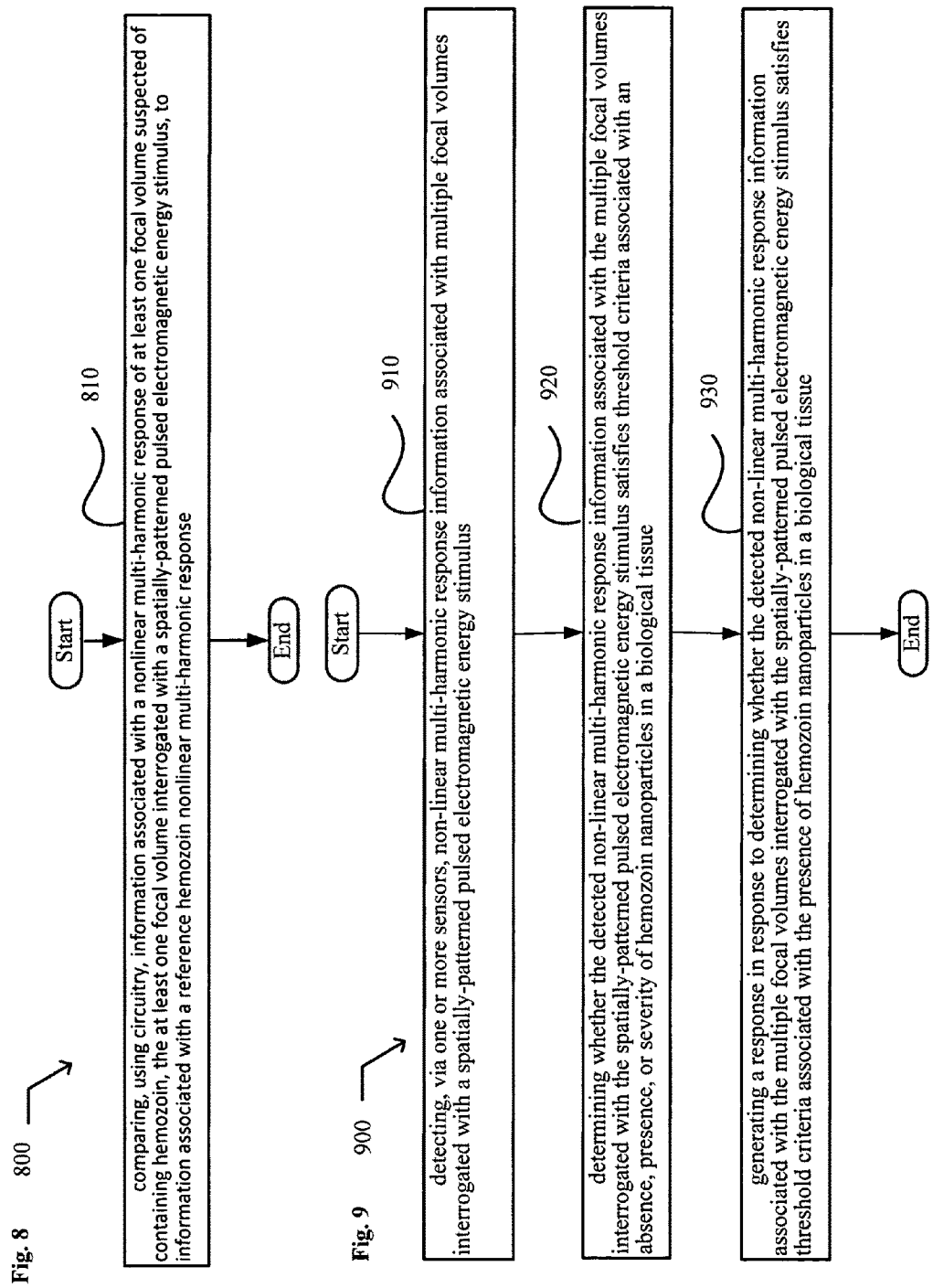

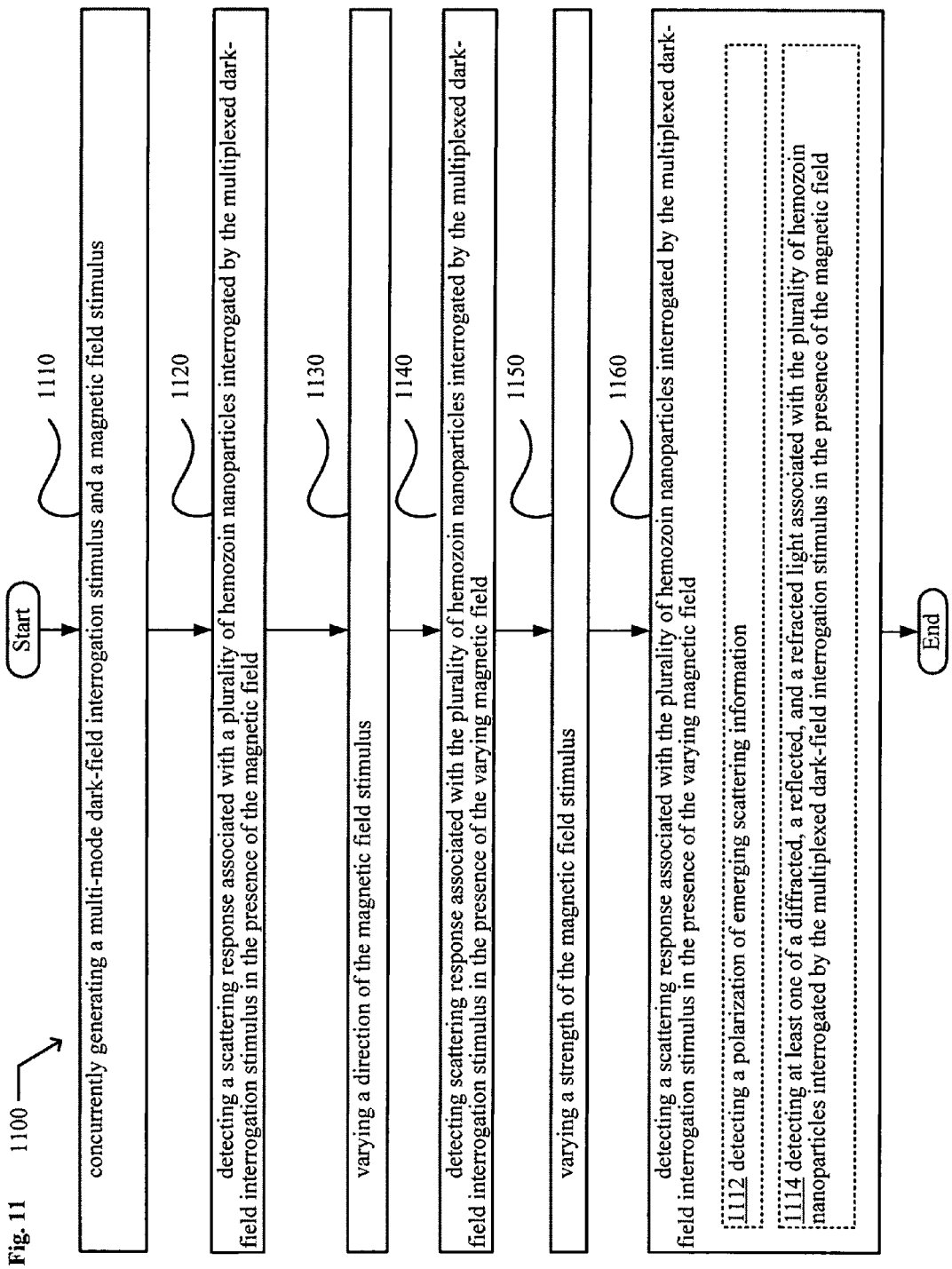

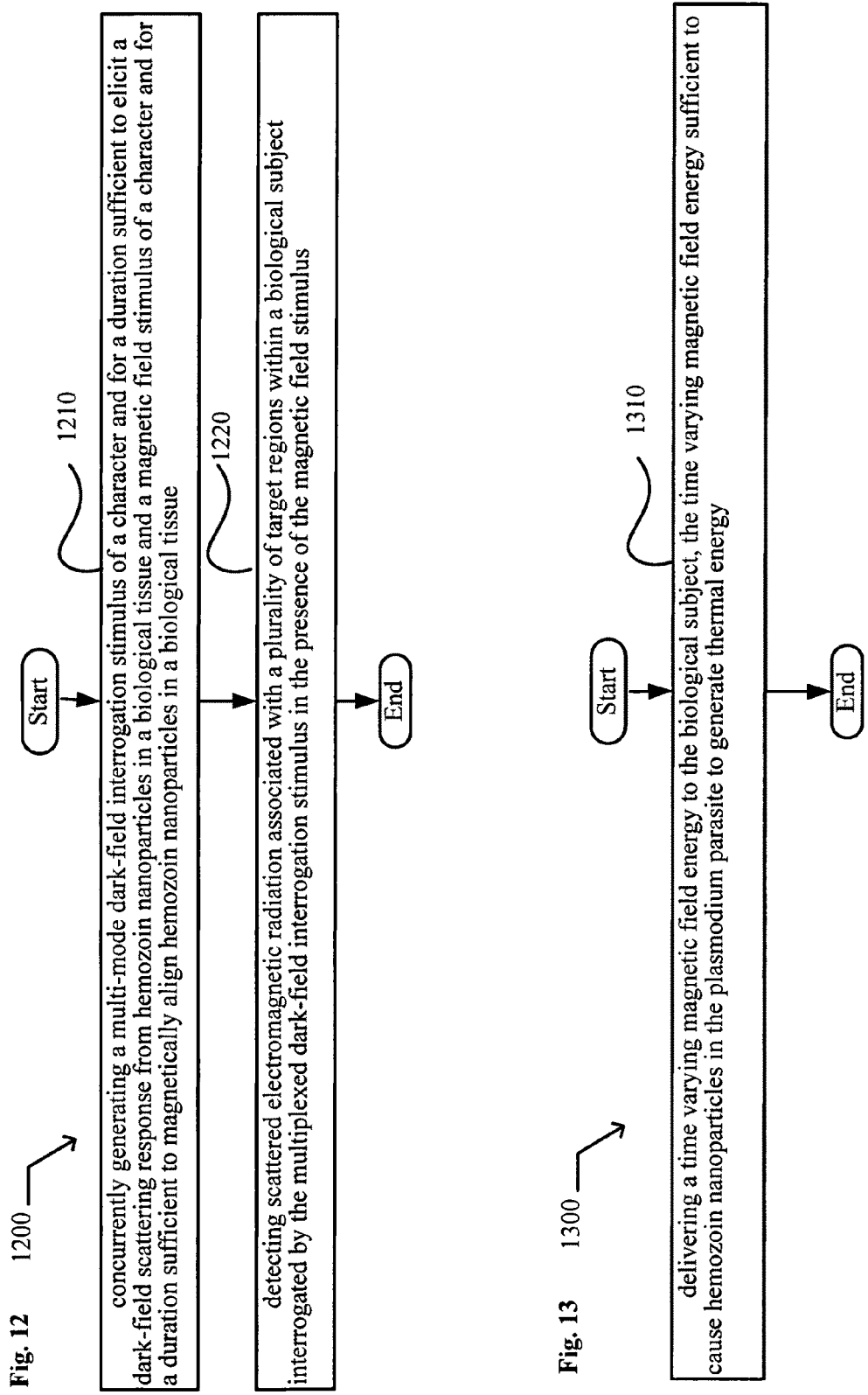

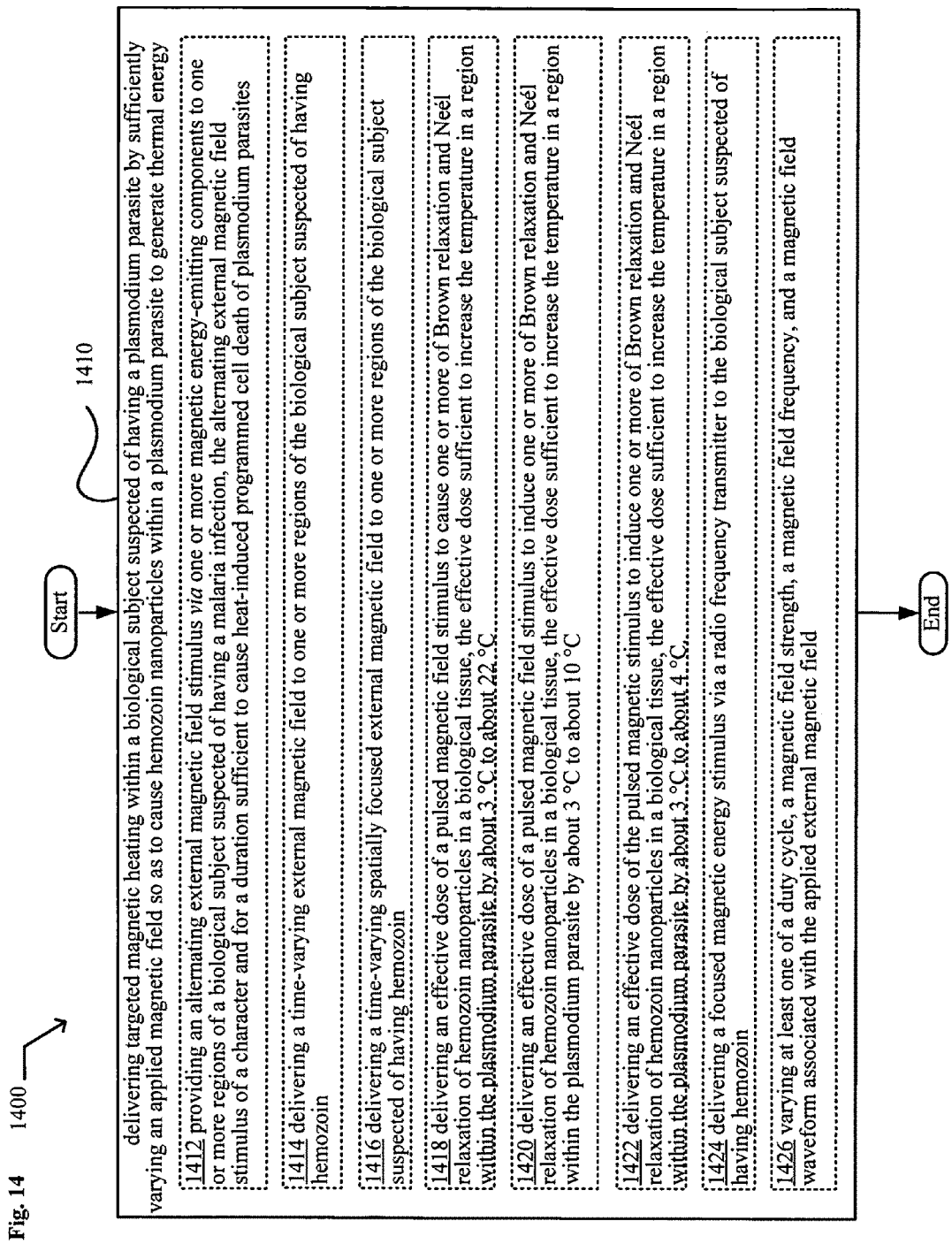

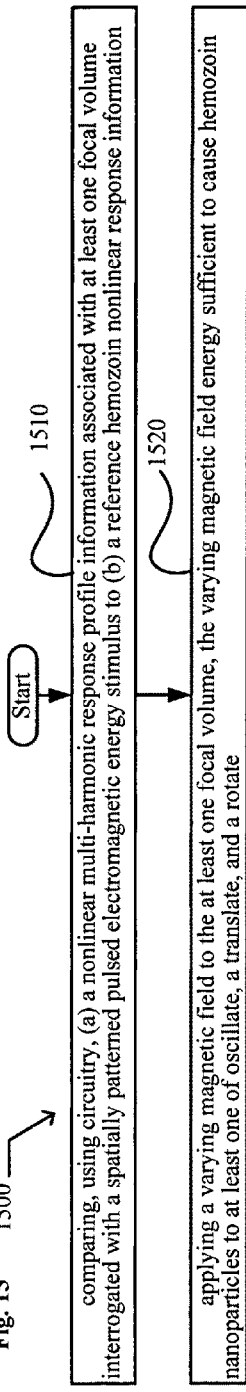
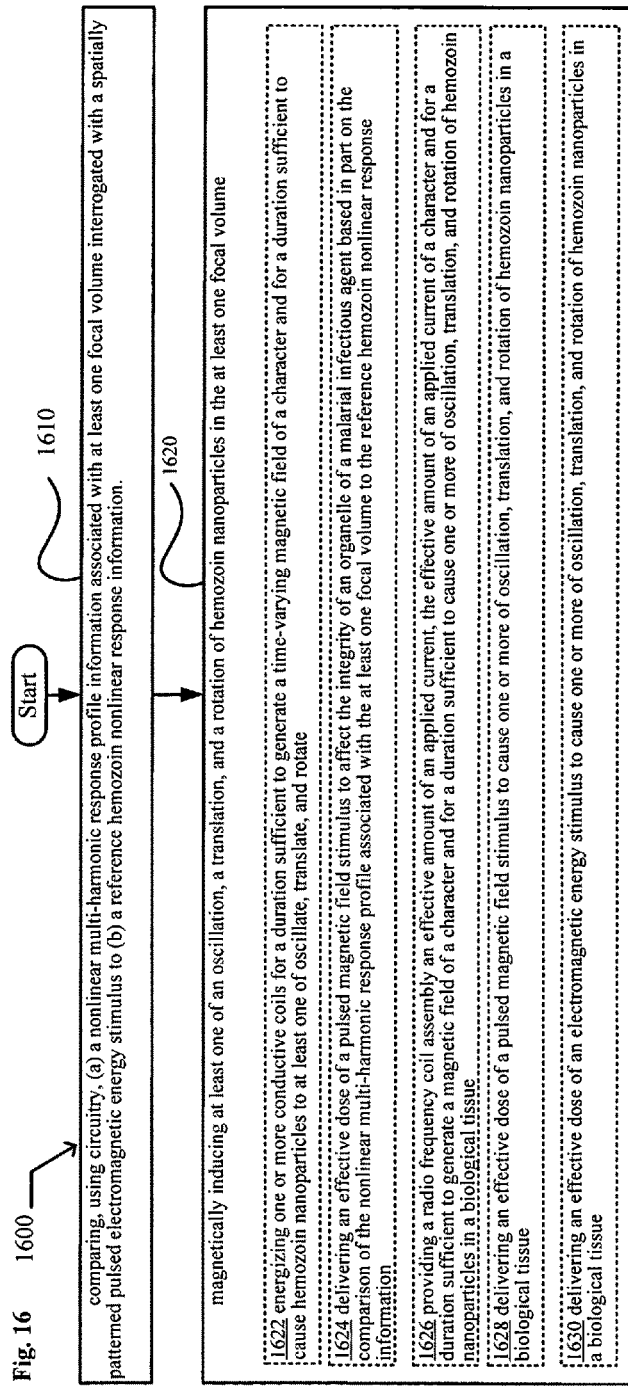

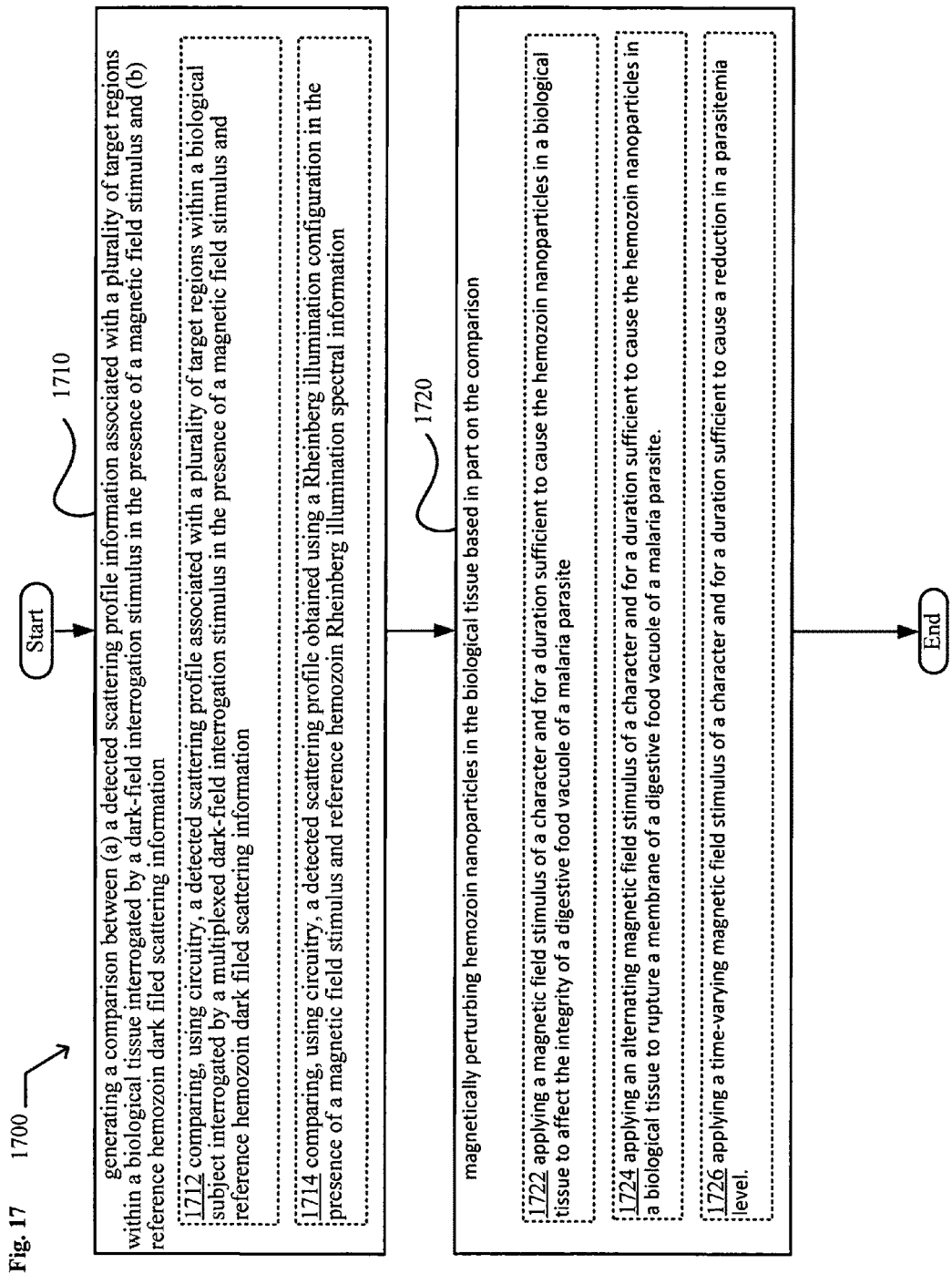

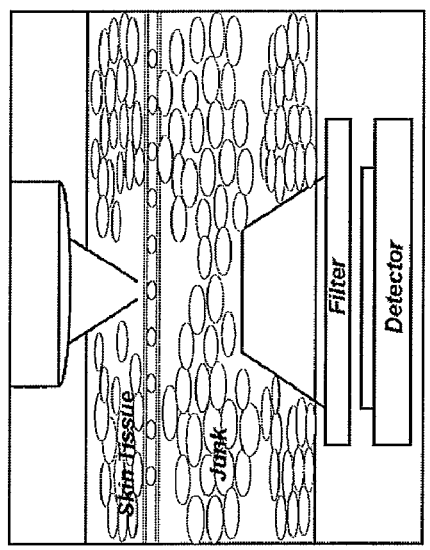
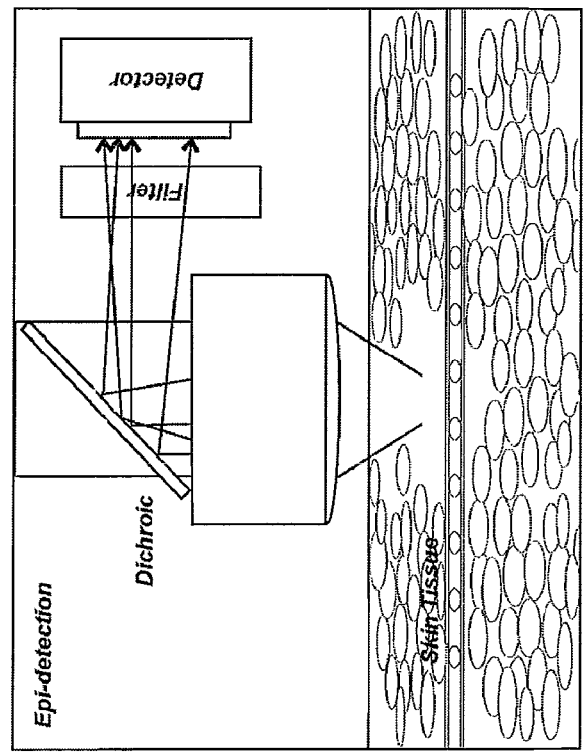

SYSTEMS, DEVICES, AND METHODS INCLUDING PARAMAGNETIC OSCILLATION, ROTATION, AND TRANSLATION OF HEMOZOIN ASYMMETRIC NANOPARTICLES IN RESPONSE TO DARK-FIELD OR RHEINBERG DETECTION OF THE PRESENCE OF HEMOZOIN

CROSS-REFERENCE TO RELATED APPLICATIONS

The present application is related to and claims the benefit of the earliest available effective filing dates from the following listed applications (the "Related Applications") (e.g., claims earliest available priority dates for other than provisional patent applications or claims benefits under 35 U.S.C. §116(e) for provisional patent applications, for any and all parent, grandparent, great-grandparent, etc. applications of the Related Applications). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/001,765, entitled SPECTROSCOPIC DETECTION OF MALARIA VIA THE EYE, naming RODERICK A. HYDE, NATHAN P. MYHRVOLD, CLARENCE T. TEGREENE, LOWELL L. WOOD, JR. as inventors, filed 11, DEC., 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/658,619, entitled SYSTEMS, DEVICES, AND METHODS INCLUDING MULTI-HARMONIC OPTICAL DETECTION OF HEMOZOIN NANOPARTICLES, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10, FEB., 2010, which is currently co-pending, or is an application of which a currently co-pending application is entitled to the benefit of the filing date (0108-004-012A-000000).

For purposes of the USPTO extra-statutory requirements, the present application constitutes a continuation-in-part of U.S. patent application Ser. No. 12/658,580, entitled SYSTEMS, DEVICES, AND METHODS INCLUDING ENHANCED DARK FIELD DETECTION OF HEMOZOIN NANOPARTICLES, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10, FEB., 2010, which is currently co-pending, or is an application of which a currently co-pending application is entitled to the benefit of the filing date (0108-004-012B-000000).

For purposes of the USPTO extra-statutory requirements, the present application constitutes a continuation-in-part of U.S. patent application Ser. No. 12/658,617, entitled SYSTEMS, DEVICES, AND METHODS INCLUDING PARAMAGNETIC OSCILLATION, ROTATION AND TRANSLATION OF HEMOZOIN ASYMMETRIC NANOPARTICLES IN RESPONSE TO MULTI-HARMONIC OPTICAL DETECTION OF THE PRESENCE OF HEMOZOIN, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10, FEB., 2010, which is currently co-pending, or is an application of which a currently co-pending application is entitled to the benefit of the filing date (0108-004-013A-000000).

For purposes of the USPTO extra-statutory requirements, the present application constitutes a continuation-in-part of U.S. patent application Ser. No. 12/658,638, entitled SYSTEMS, DEVICES, AND METHODS INCLUDING PARAMAGNETIC OSCILLATION, ROTATION AND TRANSLATION OF HEMOZOIN ASYMMETRIC NANOPARTICLES IN RESPONSE TO MULTI-HARMONIC OPTICAL DETECTION OF THE PRESENCE OF HEMOZOIN, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10, FEB., 2010, which is currently co-pending, or is an application of which a currently co-pending application is entitled to the benefit of the filing date (0108-004-013B-000000).

For purposes of the USPTO extra-statutory requirements, the present application constitutes a continuation-in-part of U.S. patent application Ser. No. 12/658,607, entitled SYSTEMS, DEVICES, AND METHODS FOR INDUCING ULTRAVIOLET ENERGY GENERATION VIA HEMOZOIN NANOPARTICLES IN A BIOLOGICAL TISSUE, naming MICHAEL C. HEGG, MATTHEW P. HORNING, JORDIN T. KARE, NATHAN P. MYHRVOLD, CLARENCE T. TEGREENE, BENJAMIN K. WILSON, LOWELL L. WOOD, JR. as inventors, filed 10, FEB., 2010, which is currently co-pending, or is an application of which a currently co-pending application is entitled to the benefit of the filing date (0108-004-013D-000000).

The USPTO has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In an aspect, the present disclosure is directed to, among other things, a hemozoin-monitoring device. The hemozoin-monitoring device includes, among other things, a sensor component configured to detect a nonlinear multi-harmonic response profile associated with hemozoin nanoparticles in a biological tissue within multiple focal volumes interrogated by an electromagnetic energy stimulus (e.g., a pulsed electromagnetic energy stimulus, a spatially-patterned electromagnetic energy stimulus, a multiplexed electromagnetic energy stimulus, a spatially-patterned pulsed multiplexed electromagnetic energy stimulus, a temporally patterned electromagnetic energy stimulus, or the like). In an embodiment, the sensor component is configured to detect a nonlinear multi-harmonic response profile using one or more differential illumination configurations (e.g., dark-field illumination, Rheinberg illumination, or the like). In an embodiment, the sensor component is configured to detect a nonlinear multi-harmonic response profile using at least one of a dark-field detection configuration and a Rheinberg detection configuration. In an embodiment, the sensor component is configured to detect a spectral signature characteristic for hemozoin optionally using at least one of a dark-field detection configuration and a Rheinberg detection configuration.

The hemozoin-monitoring device can include, among other things, one or more computer-readable storage media including executable instructions stored thereon that, when executed on a computer, instruct a controller to retrieve from storage one or more parameters associated with reference hemozoin nonlinear response information, and instructions to perform a comparison of a detected nonlinear multi-harmonic response profile to the retrieved one or more parameters. In an embodiment, the hemozoin-monitoring device includes a transceiver configured to concurrently or sequentially transmit or receive information.

In an aspect, the present disclosure is directed to, among other things, a system including an energy-emitting component configured to interrogate one or more focal volumes with a multiplexed electromagnetic energy stimulus. In an embodiment, the energy-emitting component is configured to interrogate at least one focal volume with a pulsed multiplexed electromagnetic energy stimulus. In an embodiment, the energy-emitting component is configured to interrogate at least one focal volume with a spatially-patterned pulsed multiplexed electromagnetic energy stimulus.

The system can include, among other things, circuitry configured to detect nonlinear multi-harmonic response energy associated with hemozoin nanoparticles within one or more focal volumes interrogated by the multiplexed electromagnetic energy stimulus. The system can further include, among other things, circuitry configured to compare information associated with the detected nonlinear multi-harmonic response energy to a reference hemozoin response profile.

In an aspect, the present disclosure is directed to, among other things, a method for detecting a condition associated with plasmodium-infected erythrocytes. The method includes, but is not limited to, comparing, via circuitry, a nonlinear multi-harmonic response profile associated with at least one focal volume interrogated with a spatially-patterned pulsed electromagnetic energy stimulus to reference hemozoin nonlinear response information. In an embodiment, the method includes obtaining spectral information associated with plasmodium-infected erythrocytes by detecting a nonlinear multi-harmonic response spectral profile elicited by a multiplexed (e.g., multi-frequency, multi-peak emission wavelength, multi-waveform, or the like) electromagnetic energy stimulus. In an embodiment, the method includes obtaining spectral information associated with plasmodium-infected erythrocytes by detecting spectral differences between a first and a second region of the biological subject, as well as by detecting spectral differences between nonlinear multi-harmonic responses concurrently or sequentially elicited at multiple wavelengths. Such "differential" measurements may allow for better signal to noise, may reduce the occurrence of false positives, and may minimize the effect of other spectral parameters of the body that vary over time.

In an aspect, a method includes, but is not limited to, comparing, via circuitry, information associated with a nonlinear multi-harmonic response of at least one focal volume suspected of containing hemozoin and that is interrogated with a spatially-patterned pulsed electromagnetic energy stimulus, to information associated with a reference hemozoin nonlinear multi-harmonic response.

In an aspect, a method includes, among other things, eliciting a nonlinear multi-harmonic response from in vivo hemozoin nanoparticles in a biological tissue within a focal volume by interrogating the focal volume with a pulsed electromagnetic energy stimulus having a resolution [0.61*(peak emission wavelength/numerical aperture)] ranging from about 300 nanometers to about 10 micrometers. In an embodiment, the method includes comparing, via circuitry, nonlinear multi-harmonic response information to reference hemozoin nonlinear response information configured as a physical data structure.

In an aspect, a method includes, among other things, detecting a presence of hemozoin by interrogating a biological sample with an electromagnetic stimulus of a character and for a duration to elicit a nonlinear multi-harmonic response from hemozoin nanoparticles in the biological sample. In an embodiment the electromagnetic stimulus is a pulsed electromagnetic energy stimulus having a resolution [0.61*(peak emission wavelength/numerical aperture)] ranging from about 300 nanometers to about 10 micrometers. In an embodiment, the method includes comparing, via circuitry, nonlinear multi-harmonic response information to reference hemozoin nonlinear response information configured as a physical data structure.

In an aspect, a method includes, among other things, interrogating at least one focal volume suspected of containing hemozoin with a spatially-patterned pulsed electromagnetic energy stimulus. In an embodiment, the method includes (a) comparing, using circuitry, information associated with a nonlinear multi-harmonic response, of the at least one focal volume interrogated with the spatially-patterned pulsed electromagnetic energy stimulus, to (b) information associated with a reference hemozoin nonlinear response.

In an aspect, an in situ method includes, among other things, detecting, via one or more sensors, non-linear multi-harmonic response information associated with multiple focal volumes interrogated with a spatially-patterned pulsed electromagnetic energy stimulus. In an embodiment, the method includes determining whether the detected non-linear multi-harmonic response information associated with the multiple focal volumes interrogated with the spatially-patterned pulsed electromagnetic energy stimulus satisfies threshold criteria associated with an absence, presence, or severity of hemozoin nanoparticles in a biological tissue.

In an aspect, the present disclosure is directed to, among other things, a medical diagnostic device. The medical diagnostic device includes, among other things, circuitry configured to generate a multiplexed pulsed electromagnetic energy stimulus having a peak power ranging from about 400 gigawatts to about 8 terawatts. In an embodiment, the medical diagnostic device includes circuitry configured to direct the multiplexed pulsed electromagnetic energy stimulus on a plurality of focal volumes in a biological subject. In an embodiment, the medical diagnostic device includes circuitry configured to detect a multi-harmonic response associated with a plurality of hemozoin nanoparticles in a biological tissue within one or more of the plurality of focal volumes interrogated by the multiplexed pulsed electromagnetic energy stimulus.

In an aspect, a method includes, among other things, selectively energizing a plurality of focal volumes within a biological subject with a pulsed multiplexed electromagnetic energy stimulus, the pulsed multiplexed electromagnetic energy stimulus of a character and for a duration sufficient to elicit a multi-harmonic response from hemozoin nanoparticles carried by an in vivo parasite within one or more of the plurality of focal volumes. In an embodiment, the method includes generating a comparison between an elicited multi-harmonic response and hemozoin multi-harmonic signature information.

In an aspect, the present disclosure is directed to, among other things, an in situ hemozoin-monitoring device. The in situ hemozoin-monitoring device includes, among other things, an actively-controllable excitation component configured to deliver a spatially-patterned pulsed electromagnetic energy stimulus to one or more focal volumes and configured to elicit a non-linear multi-harmonic response information from hemozoin nanoparticles in a biological tissue within the multiple focal volumes. In an embodiment, the in situ hemozoin-monitoring device includes a control means operably coupled to the actively-controllable excitation component and configured to regulate at least one of a numerical aperture, a spaced-apart delivery pattern parameter, and a temporal delivery pattern parameter associated with the delivery of the spatially-patterned pulsed electromagnetic energy stimulus. In an embodiment, the actively-controllable excitation component is configured to regulate at least one parameter associated with a peak power, a peak irradiance, a focal spot size, and a pulse width.

In an aspect, the present disclosure is directed to, among other things, an anti-malarial therapeutic device. The anti-malarial therapeutic device includes, among other things, a sensor component including at least one sensor configured to detect nonlinear multi-harmonic response energy associated with hemozoin nanoparticles within at least one focal volume of a biological tissue interrogated by an electromagnetic energy stimulus. In an embodiment the anti-malarial therapeutic device includes an energy-emitting component configured to deliver an effective amount of a electromagnetic energy stimulus to elicit a nonlinear optical response from hemozoin nanoparticles within the biological tissue, the elicited nonlinear response of a character and for a duration sufficient to modulate a biological activity of a malarial infectious agent within the biological tissue. In an embodiment, the anti-malarial therapeutic device includes a controller operably coupled to at least one sensor of the sensor component and the energy-emitting component, the controller configured to provide a control signal to the energy-emitting component.

In an aspect, the present disclosure is directed to, among other things, a system including circuitry configured to generate a multi-mode dark-field interrogation stimulus. In an embodiment, the system includes circuitry configured to generate a magnetic field. In an embodiment, the system includes circuitry configured to detect scattering information associated with a plurality of hemozoin nanoparticles interrogated by a multiplexed dark-field interrogation stimulus in the presence of the magnetic field.

In an aspect, the present disclosure is directed to, among other things, a medical diagnostic device. The medical diagnostic device includes, among other things, a dark-field electromagnetic energy emitting component. In an embodiment, the dark-field electromagnetic energy emitting component is configured to deliver a multi-mode dark-field interrogation stimulus to at least one blood vessel. The medical diagnostic device can includes, among other things, a magnetic field component. In an embodiment, the magnetic field component is configured to generate a magnetic field of a character and for a duration sufficient to magnetically align, in a biological tissue, a plurality of hemozoin nanoparticles. The medical diagnostic device includes, among other things, an optical energy sensor component. In an embodiment, the optical energy sensor component is configured to detect scatter optical energy from the plurality of hemozoin nanoparticles interrogated by the multi-mode dark-field interrogation stimulus in the presence of the magnetic field.

In an aspect, a method includes, among other things, concurrently generating a multi-mode dark-field interrogation stimulus and a magnetic field stimulus. In an embodiment, the method includes detecting a scattering response associated with a plurality of hemozoin nanoparticles interrogated by the multiplexed dark-field interrogation stimulus in the presence of the magnetic field.

In an aspect, a method includes, among other things, concurrently generating a multi-mode dark-field interrogation stimulus of a character and for a duration sufficient to elicit a dark-field scattering response from hemozoin nanoparticles in a biological tissue. In an embodiment, the detecting scattered electromagnetic radiation associated with a plurality of target regions within a biological subject interrogated by the multiplexed dark-field interrogation stimulus in the presence of the magnetic field stimulus.

In an aspect, the present disclosure is directed to, among other things, an apparatus including an actively-controllable magnetic field generator and a controller operatively coupled to the actively-controllable magnetic field generator. In an embodiment, the actively-controllable magnetic field generator is configured to deliver a varying magnetic field stimulus at a dose sufficient to cause heat generation from hemozoin nanoparticles within a biological sample. In an embodiment, the controller is operatively coupled to the actively-controllable magnetic field generator, and includes one or more processors for controlling at least one of a magnetic field ON duration, a magnetic field strength, a magnetic field frequency, and a magnetic field waveform.

In an aspect, the present disclosure is directed to, among other things, a method of heat-shocking a plasmodium parasite. The method of heat-shocking a plasmodium parasite includes generating targeted heating within a plasmodium parasite by sufficiently varying an applied magnetic field so as to cause hemozoin nanoparticles within a plasmodium parasite to generate thermal energy.

In an aspect, the present disclosure is directed to a method of treating a biological subject suspected of being infected with a plasmodium parasite. The method includes delivering varying magnetic field energy to the biological subject, the varying magnetic field energy sufficient to cause hemozoin nanoparticles in the plasmodium parasite to generate thermal energy.

In an aspect, the present disclosure is directed to, among other things, system for modulating plasmodium parasitic activity. The system for modulating plasmodium parasitic activity includes, among other things, circuitry configured to generate a magnetic field stimulus of a character and for a duration sufficient to elicit hemozoin nanoparticles within a biological sample to deliver magnetically induced hyperthermia therapy in vivo. In an embodiment, the system for modulating plasmodium parasitic activity includes circuitry configured to dynamically control the magnetic field stimulus.

In an aspect, the present disclosure is directed to, among other things, a system including circuitry configured to compare (a) a nonlinear multi-harmonic response energy profile associated with at least one focal volume interrogated with a spatially patterned pulsed electromagnetic energy stimulus to (b) reference hemozoin nonlinear response information. In an embodiment, the system includes circuitry configured to magnetically induce at least one of an oscillation, a translation, and a rotation of hemozoin nanoparticles in a biological sample, the induced at least one of the oscillation, the translation, and the rotation of hemozoin nanoparticles in the biological sample of a character and for a duration sufficient to affect the integrity of an organelle of a plasmodium parasite.

In an aspect, the present disclosure is directed to, among other things, a method of enhancing a Brownian or Neelian process of a hemozoin nanoparticle. In an embodiment, the method of enhancing a Brownian or Neelian process of a hemozoin nanoparticle includes applying a varying magnetic field to at least one focal volume suspected of having hemozoin nanoparticles, the varying magnetic field sufficient to cause hemozoin nanoparticles within the focal volume to at least one of oscillate, a translate, and a rotate. The method of enhancing a Brownian or Neelian process of a hemozoin nanoparticle can further include comparing, using circuitry, (a) a nonlinear multi-harmonic response profile information associated with at least one focal volume interrogated with a spatially patterned pulsed electromagnetic energy stimulus to (b) a reference hemozoin nonlinear response information. In an embodiment, the method may further include generating a response based on the comparison.

In an aspect, the present disclosure is directed to, among other things, a method of treating a plasmodium parasitic infection. In an embodiment, the method of treating the plasmodium parasitic infection includes comparing, using circuitry, (a) a nonlinear multi-harmonic response profile information associated with at least one focal volume interrogated with a spatially patterned pulsed electromagnetic energy stimulus to (b) a reference hemozoin nonlinear response information. In an embodiment, the method of treating a plasmodium parasitic infection includes magnetically inducing at least one of an oscillation, a translation, and a rotation of hemozoin nanoparticles in the at least one focal volume based on the comparison.

In an aspect, the present disclosure is directed to, among other things, a system including circuitry configured to detect a scattered energy from a biological tissue in at least one of a dark-field detection configuration and a Rheinberg detection configuration. In an embodiment, the system includes circuitry configured to magnetically perturb hemozoin nanoparticles in the biological tissue in response to a comparison between detected scattered energy information and reference hemozoin nanoparticles scattered energy information.

In an aspect, a method includes, among other things, generating a comparison between (a) a detected scattering profile information associated with a plurality of target regions within a biological tissue interrogated by a dark-field interrogation stimulus in the presence of a magnetic field stimulus and (b) reference hemozoin dark field scattering information. In an embodiment, the method includes magnetically perturbing hemozoin nanoparticles in the biological tissue based in part on the comparison.

In an aspect, the present disclosure is directed to, among other things, an apparatus including a magnetic field generator configured to concurrently or sequentially generate at least a first electromagnetic energy stimulus and a second electromagnetic energy stimulus, the first electromagnetic energy stimulus of a character and for a duration sufficient to magnetically align hemozoin nanoparticles in a biological tissue, the second electromagnetic energy stimulus of a character and for a duration sufficient to magnetically induce at least one of an oscillation, a translation, and a rotation of the hemozoin nanoparticles in the biological tissue.

In an aspect, the present disclosure is directed to, among other things, a system including circuitry configured to detect a nonlinear multi-harmonic response energy associated with hemozoin nanoparticles within at least one focal volume of a biological tissue interrogated by an electromagnetic energy stimulus. In an embodiment, the system includes circuitry configured to generate an effective amount of a pulsed electromagnetic energy stimulus to elicit a nonlinear response from hemozoin nanoparticles in a biological tissue within the at least one focal volume of the biological tissue. In an embodiment, the elicited nonlinear response is of a character and for a duration sufficient to modulate a biological activity of a malarial infectious agent.

In an aspect, the present disclosure is directed to, among other things, a method for modulating plasmodium parasitic activity. The method includes eliciting a nonlinear multi-harmonic response from hemozoin nanoparticles in a biological tissue by interrogating a plurality of focal volumes with a pulsed electromagnetic energy stimulus having a peak irradiance of less than about 200 gigawatts/cm$^2$ and having at least one peak emission wavelength ranging from about 690 nanometers to about 2100 nanometers. In an embodiment, the pulsed electromagnetic energy stimulus is of a character and for a duration sufficient to modulate a biological activity of a malarial infectious agent. In an embodiment, the pulsed electromagnetic energy stimulus includes a peak irradiance of less than about 200 gigawatts/cm$^2$ and two or more peak emission wavelengths ranging from about 690 nanometers to about 2100 nanometers. In an embodiment, the pulsed electromagnetic energy stimulus includes a peak irradiance of less than about 200 gigawatts/cm$^2$ and three or more peak emission wavelengths ranging from about 690 nanometers to about 2100 nanometers.

In an aspect, the present disclosure is directed to, among other things, a method for detecting plasmodium parasitic activity. The method includes eliciting a nonlinear multi-harmonic response from a biological sample suspected of having a plasmodium parasite by interrogating a plurality of focal volumes with a pulsed electromagnetic energy stimulus having a peak irradiance of less than about 200 gigawatts/cm$^2$ and having at least one peak emission wavelength ranging from about 690 nanometers to about 2100 nanometers. In an embodiment, the pulsed electromagnetic energy stimulus includes a peak irradiance of less than about 200 gigawatts/cm$^2$ and two or more peak emission wavelengths ranging from about 690 nanometers to about 2100 nanometers. In an embodiment, the pulsed electromagnetic energy stimulus includes a peak irradiance of less than about 200 gigawatts/cm$^2$ and three or more peak emission wavelengths ranging from about 690 nanometers to about 2100 nanometers.

In an aspect, the present disclosure is directed to, among other things, an anti-malarial therapeutic method. The an anti-malarial therapeutic method includes applying an electromagnetic energy stimulus of a sufficient strength and duration to elicit hemozoin nanoparticles within a biological sample to generate an in vivo antimicrobial energy stimulus in response to a determination that hemozoin nanoparticles are present within the biological sample.

In an aspect, the present disclosure is directed to, among other things, a method including detecting a hemozoin in a biological tissue by interrogation one or more focal volumes in the biological tissue with a pulsed electromagnetic energy stimulus having a resolution [0.61*(peak emission wavelength/numerical aperture)] ranging from about 300 nanometers to about 10 micrometers. The method may further include comparing, using circuitry, a nonlinear multi-harmonic response associated with the one or more focal volumes in the biological tissue to reference hemozoin nonlinear response information configured as a physical data structure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 8 is a flow diagram of a method according to one illustrated embodiment.

FIG. 9 is a flow diagram of a method according to one illustrated embodiment.

FIG. 11 is a flow diagram of a method according to one illustrated embodiment.

FIG. 12 is a flow diagram of a method according to one illustrated embodiment.

FIG. 13 is a flow diagram of a method according to one illustrated embodiment.

FIG. 14 is a flow diagram of a method according to one illustrated embodiment.

FIG. 15 is a flow diagram of a method according to one illustrated embodiment.

FIG. 16 is a flow diagram of a method according to one illustrated embodiment.

FIG. 17 is a flow diagram of a method according to one illustrated embodiment.

FIG. 31A is a prospective view of a monitor/treatment device according to one illustrated embodiment.

FIG. 31B is a prospective view of a monitor/treatment device using epi-detection according to one illustrated embodiment.

DETAILED DESCRIPTION

Figure 1A:
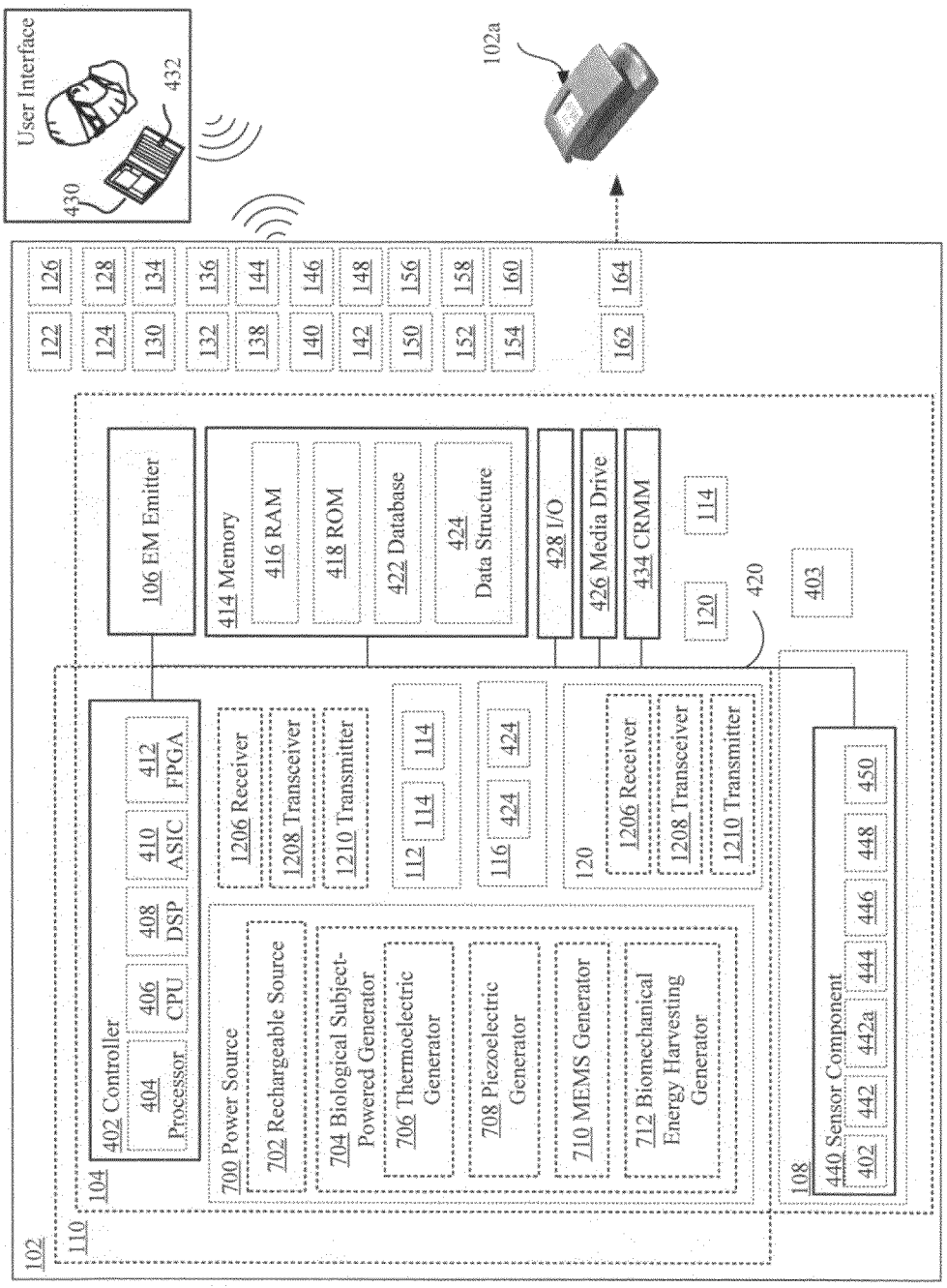
FIG. 1A is a perspective view of a system according to one illustrated embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Malaria remains one of the most important communicable diseases in the world. The World Health Organization estimates that about half of the world's population lives in areas having some risk of exposure to malaria. See, e.g., World Health Organization, *World Malaria Report* 2008, WHO: Geneva 9 (2008). Malaria is a vector-borne infectious disease caused by a eukaryotic protist of the genus *Plasmodium*. Among *Plasmodium* species that can infect humans, examples include *Plasmodium falciparum*, *Plasmodium knowlesi*, *Plasmodium malariae*, *Plasmodium ovale*, and *Plasmodium vivax*. A 2006 World Health Organization estimate indicates that about 247 million cases of malaria occur annually of which 230 million are due to *Plasmodium falciparum*. See, e.g., World Health Organization, *World Malaria Report* 2008, WHO: Geneva 10 (2008).

An aspect includes systems, devices, and methods for detecting (e.g., assessing, calculating, evaluating, determining, gauging, identifying, measuring, monitoring, quantifying, resolving, sensing, or the like) an infectious agent marker present in, for example, a biological sample or tissue (e.g., blood, bone, muscle, skin, adipose tissue, fluid, tendons, organs, ventricles, or the like, either in vivo or in vitro). A non-limiting example includes systems, devices, and methods of actively monitoring a biological subject suspected of being infected with a plasmodium parasite. A non-limiting example includes systems, devices, and methods including dark-field or Rheinberg detection technologies and methodologies.

An aspect includes systems, devices, and methods include multi-harmonic optical detection of hemozoin nanoparticles. A non-limiting example includes systems, devices, and methods including enhanced dark field detection of hemozoin nanoparticles. An aspect includes systems, devices, methods, and compositions for actively detecting and treating a malarial infection. A non-limiting example includes systems, devices, and methods for heat-shocking malaria infected erythrocytes. A non-limiting example includes systems, devices, and methods including paramagnetic oscillation, rotation, and translation of hemozoin asymmetric nanoparticles in response to multi-harmonic optical detection of the presence of hemozoin. A non-limiting example includes systems, devices, and methods including ultraviolet energy generation via hemozoin nanoparticles in a biological tissue.

FIG. 1A shows a system 100, in which one or more methodologies or technologies can be implemented such as, for example, actively detecting or treating a malarial infection. The system 100 can include, but is not limited to, one or more monitor/treatment devices 102. Nonlimiting examples of monitor/treatment devices 102 include hemozoin-monitoring devices, spectrometers, anti-malarial therapeutic devices, malarial retinal diagnostic devices, parasitemia detectors, transcutaneous detectors 102a, opthalmoscopes (e.g., opthalmoscopes employing nonlinear optics, dark-field, or Rheinberg detection configurations, technologies, and methodologies), and the like.

The system 100 can include, among other things, an energy-emitting component 104 configured to interrogate one or more focal volumes with an electromagnetic energy stimulus. Non-limiting examples of energy-emitting components 104 include electromagnetic radiation emitters, and the like. Further non-limiting examples of energy-emitting components 104 include electric circuits, electrical conductors, cavity resonators, electro-mechanical components, electro-opto components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency light-emitting diodes, or the like), arc flashlamps, incandescent emitters, continuous wave bulbs, and the like. In an embodiment, the energy-emitting component 104 includes at least one two-photon excitation component. In an embodiment, the energy-emitting component 104 includes one or more lasers, laser diodes, and light-emitting diodes. In an embodiment, the energy-emitting component 104 includes one or more quantum dots, organic light-emitting diodes, microcavity light-emitting diodes, and polymer light-emitting diodes. In an embodiment, the energy-emitting component 104 includes at least one of an exciplex laser, a diode-pumped solid state laser, and a semiconductor laser. In an embodiment, the energy-emitting component 104 includes one or more tunable ultrafast lasers. In an embodiment, the energy-emitting component 104 includes one or more femtosecond lasers. In an embodiment, the energy-emitting component 104 includes one or more Ti:sapphire lasers. In an embodiment, the energy-emitting component 104 is configured to interrogate at least one focal volume with a spatially-patterned electromagnetic energy stimulus having at least a first region and a second region different from the first region. In an embodiment, the energy-emitting component 104 is configured to interrogate at least one focal volume with a spatially-patterned electromagnetic energy stimulus having at least a first region and a second region, the second region having at least one of an illumination intensity, an energy-emitting pattern, a peak emission wavelength, an ON-pulse duration, an OFF-pulse duration, and a pulse frequency different from the first region. In an embodiment, the energy-emitting component 104 is configured to interrogate at least one focal volume with a spatially-patterned pulsed multiplexed electromagnetic energy stimulus. In an embodiment, the energy-emitting component 104 is configured to generate a multiplexed electromagnetic energy stimulus having, for example, two or more peak emission wavelengths.

In an embodiment, the electromagnetic energy-emitting component 104 is configured to direct (e.g., via one or more waveguides) electromagnetic radiation toward a biological sample (e.g., tissue, blood capillaries underneath the skin, or the like). If the biological sample is infected with malaria parasites, the hemozoin within them will emit a characteristic optical response back through the skin.

In an embodiment, by adjusting the wavelength of the electromagnetic stimulus generated by the energy emitting component 104, it is possible to control the wavelength of light that emerges from the hemozoin (i.e., it is possible to control the wavelength of the emerging nonlinear optical response of the hemozoin. In an embodiment, one or more peak emission wavelengths of the electromagnetic stimulus generated by the energy-emitting component 104 are chosen to elicit a nonlinear optical response of hemozoin to emit within a wavelength range that damages genetic material.

In an embodiment, the energy-emitting component 104 is configured to deliver a spatially-patterned pulsed multiplexed electromagnetic energy stimulus having a peak power ranging from about 400 gigawatts to about 8 terawatts. In an embodiment, the energy-emitting component 104 is configured to generate a spatially-patterned pulsed multiplexed electromagnetic energy stimulus having a peak irradiance of less than about 200 gigawatts/cm^2. In an embodiment, the energy-emitting component 104 is configured to generate a spatially-patterned pulsed multiplexed electromagnetic energy stimulus having an average power ranging from about 1 miliwatt to about 1 watt. In an embodiment, the energy-emitting component 104 is configured to generate a spatially-patterned pulsed multiplexed electromagnetic energy stimulus having one or more peak emission wavelengths ranging from about 690 nanometers to about 2000 nanometers. In an embodiment, the energy-emitting component 104 is configured to generate spatially-patterned pulsed multiplexed electromagnetic energy stimulus having a resolution [0.61*(peak emission wavelength/numerical aperture)] ranging from about 300 nanometers to about 10 micrometers. Energy-emitting components 104 forming part of a monitor/treatment device 102, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, or any combination thereof. One or more of the energy-emitting components 104 may have a peak emission wavelength in the x-ray, ultraviolet, visible, infrared, near infrared, terahertz, microwave, or radio frequency spectrum. In an embodiment, the energy-emitting component 104 includes a patterned energy-emitting source. In an embodiment, the energy-emitting component 104 includes a patterned light-emitting source.

In an embodiment, the energy-emitting component 104 is configured to concurrently or sequentially interrogate multiple focal volumes with the spatially-patterned pulsed multiplexed electromagnetic energy stimulus. In an embodiment, the energy-emitting component 104 is configured to concurrently or sequentially interrogate multiple focal volumes with a spatially-patterned, multifocal depth, electromagnetic energy stimulus.

In an embodiment, the energy-emitting component 104 is configured to deliver an electromagnetic energy stimulus having at least a first peak emission wavelength and a second peak emission wavelength different from the first peak emission wavelength. In an embodiment, the energy-emitting component 104 includes at least one of a first energy emitter and at least one of a second energy emitter, the at least one second energy emitter having a peak emission wavelength different from the at least one first energy emitter. In an embodiment, the energy-emitting component 104 is configured to concurrently or sequentially deliver a first pulsed electromagnetic energy stimulus and a second pulse electromagnetic energy stimulus, the second pulsed energy stimulus having at least one of a pulse duration, a pulse frequency, a pulse intensity, a pulse ratio, and a pulse repetition rate different from the first pulsed electromagnetic energy stimulus. In an embodiment, the energy-emitting component 104 is configured to concurrently or sequentially deliver a first pulsed electromagnetic energy stimulus and a second pulse electromagnetic energy stimulus, the second pulsed electromagnetic energy stimulus having a focal depth different from the first pulsed electromagnetic energy stimulus. In an embodiment, the energy-emitting component 104 is configured to concurrently or sequentially deliver a first pulsed electromagnetic energy stimulus and a second pulse electromagnetic energy stimulus, the second pulsed electromagnetic energy stimulus having a resolution different from the first pulsed electromagnetic energy stimulus. In an embodiment, at least a portion of the energy-emitting component 104 is configured for removable attachment to a biological surface of a biological subject.

In an embodiment, the energy-emitting component 104 is configured to deliver a spatially-focused electromagnetic energy stimulus.

In an embodiment, the energy-emitting component 104 includes a lens array configured to deliver a spaced-apart energy stimuli having at least a first region and at least a second region, the second region having a focal depth different from the first region. In an embodiment, the second region has a peak emission wavelength different from the first region. In an embodiment, the second region has a peak irradiance different from the first region. In an embodiment, the second region has at least one of an intensity, frequency, pulse intensity, pulse duration, pulse ratio, and pulse repetition rate different from an intensity, frequency, pulse intensity, pulse duration, pulse ratio, and pulse repetition rate of the first region. In an embodiment, the energy-emitting component 104 includes one or more orthogonal (or crossed) polarizers. In an embodiment, the sensor component 440 includes one or more orthogonal (or crossed) polarizers.

In an embodiment, the energy-emitting component 104 includes a plurality of selectively-actuatable electromagnetic energy waveguides configured to direct an emitted spatially-patterned pulsed multiplexed electromagnetic energy stimulus to one or more regions of the at least one focal volume. In an embodiment, the energy-emitting component 104 includes a dark-field electromagnetic energy emitting component configured to deliver a multi-mode dark-field interrogation stimulus to at least one blood vessel.

Figure 1B:
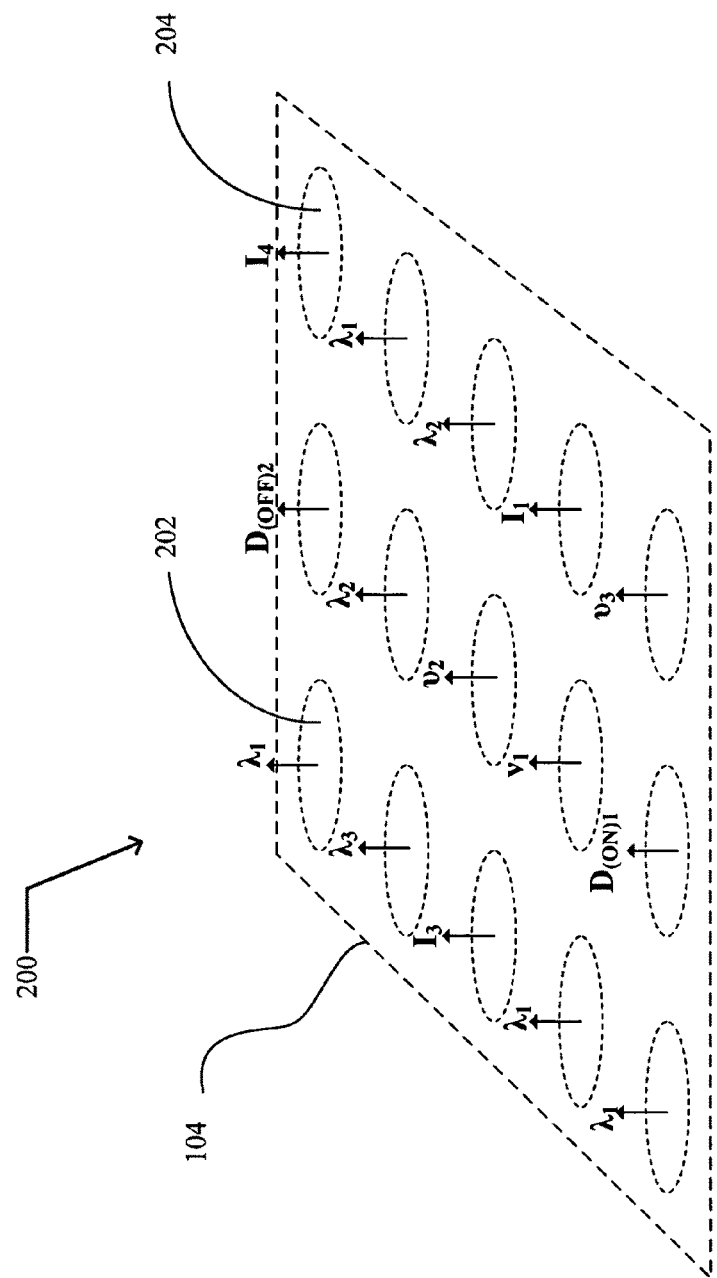
FIG. 1B is top plan view a top plan view of a portion of a monotor/treatment device including at least one energy emitting component delivering a patterned electromagnetic energy stimulus, according to one illustrated embodiment.

Referring to FIG. 1B, in an embodiment, the energy-emitting component 104 is configured to provide an illumination pattern 600 comprising at least a first region 202 and a second region 204. In an embodiment, the second region 204 of the illumination pattern 600 comprises at least one of an illumination intensity ($I_n$), an energy-emitting pattern, a peak emission wavelength ($a_n$), an ON-pulse duration ($D_{(ON)n}$), an OFF-pulse duration ($D_{(OFF)n}$), and a pulse frequency ($a_n$) different from the first region 202. The energy-emitting component 104 can be configured to provide a spatially patterned electromagnetic energy stimulus having a peak emission wavelength in at least one of an x-ray, an ultraviolet, a visible, an infrared, a near infrared, a terahertz, microwave, and a radio frequency spectrum, or combinations thereof, to at least a portion of tissue proximate an monitor/treatment device 102. In an embodiment, the energy-emitting component 104 is configured to provide a spatially patterned optical energy stimulus. The monitor/treatment device 102 can include, but is not limited to, a patterned-light emitting source. In an embodiment, the patterned-light emitting source is configured to provide a spatially patterned energy stimulus to one or more region of a biological subject.

With continued reference to FIG. 1A, the system 100 can include, among other things, circuitry 108 configured to detect (e.g., assess, calculate, evaluate, determine, gauge, measure, monitor, quantify, resolve, sense, or the like) a non-linear optical response (e.g., a nonlinear multi-harmonic response, nonlinear multi-harmonic response energy associated with hemozoin nanoparticles within the at least one focal volume interrogated by an electromagnetic energy stimulus, and the like). Circuitry can include one or more components operably coupled (e.g., communicatively coupled, electromagnetically, magnetically, ultrasonically, optically, inductively, electrically, capacitively coupleable, or the like) to each other. In an embodiment, circuitry can include one or more remotely located components. In an embodiment, remotely located components can be operably coupled via wireless communication. In an embodiment, remotely located components can be operably coupled via one or more receivers, transmitters, transceivers, and the like.

Circuitry can include, among other things, one or more controllers 402 such as a processor (e.g., a microprocessor) 404, a central processing unit (CPU) 406, a digital signal processor (DSP) 408, an application-specific integrated circuit (ASIC) 410, a field programmable gate array (FPGA) 412, or the like, or any combinations thereof, and may include discrete digital or analog circuit elements or electronics, or combinations thereof. Circuitry can include, but is not limited to, one or more field programmable gate arrays 412 having a plurality of programmable logic components. Circuitry can include, but is not limited to, one or more of an application specific integrated circuits having a plurality of predefined logic components. In an embodiment, at least one controller 402 is operably coupled to one or energy-emitting components 104. In an embodiment, circuitry includes one or more controllers 402 configured to concurrently or sequentially operate multiple energy-emitting components 104. In an embodiment, one or more controllers 402 are configured to automatically control at least one waveform characteristic (e.g., intensity, frequency, pulse intensity, pulse duration, pulse ratio, pulse repetition rate, or the like) associated with the delivery of one or more energy stimuli. For example, pulsed waves may be characterized by the fraction of time the energy stimulus is present over one pulse period. This fraction is called the duty cycle and is calculated by dividing the pulse time ON by the total time of a pulse period (e.g., time ON plus time OFF). In an embodiment, a pulse generator 403 may be configured to electronically generate pulsed periods and non-pulsed (or inactive) periods. In an embodiment, circuitry includes a controller 402 operably coupled to the energy-emitting component 104, the controller configured to control at least one parameter associated with a delivery of the spatially-patterned pulsed multiplexed electromagnetic energy stimulus.

In an embodiment, the controller 402 is configured to control at least one of a delivery regimen, a spaced-apart delivery pattern, a spatial modulation, a temporal modulation, a magnitude, a spatial-pattern configuration, and a spatial distribution associated with the delivery of the spatially-patterned multiplexed electromagnetic energy stimulus. In an embodiment, the controller 402 includes one or more processors 404 configured to control one or more parameter associated with one or more of a spatial illumination modulation, a spatial illumination intensity, and a spatial illumination delivery pattern associated with a delivery of the spatially-patterned pulsed multiplexed electromagnetic energy stimulus. In an embodiment, the controller 402 includes one or more processors 404 configured to control one or more parameters associated a pulse frequency, a pulse intensity, a pulse ratio, or a pulse repetition rate associated with a delivery of the spatially-patterned pulsed multiplexed electromagnetic energy stimulus. In an embodiment, the controller 402 includes one or more processors 404 configured to control one or more parameters associated a focal depth distribution associated with a delivery of the spatially-patterned pulsed multiplexed electromagnetic energy stimulus. In an embodiment, the controller 402 includes one or more processors 404 operably coupled to the energy-emitting component and configured to control a spatial distribution of the spatially-patterned pulsed multiplexed electromagnetic energy stimulus. In an embodiment, the system 100 includes at least one processor 404 operable to cause a storing of information associated with magnetically inducing at least one of an oscillation, translation, and rotation of hemozoin nanoparticles in a biological tissue. In an embodiment, the system 100 at least one processor 404 operable to cause a storing of information associated with comparing a nonlinear multi-harmonic response information to reference hemozoin response information on one or more computer-readable storage media.

In an embodiment, the controller 402 includes one or more processors 404 for generating a control signal associated with actively controlling at least one of a duty cycle, a pulse train frequency, and pulse repetition rate associated with a magnetic field applied to the biological sample. In an embodiment, the controller 402 includes one or more processors 404 for generating a control signal associated with actively controlling a magnetic field orientation. In an embodiment, the controller 402 includes one or more processors 404 for generating a control signal associated with actively controlling a magnetic field strength. In an embodiment, the controller 402 includes one or more processors 404 for generating a control signal associated with actively controlling a magnetic field spatial distribution. In an embodiment, the controller 402 includes one or more processors 404 for generating a control signal associated with actively controlling a magnetic field temporal pattern. In an embodiment, the controller 402 includes one or more processors 404 for generating a control signal associated with actively controlling a magnetic field ON duration. In an embodiment, the controller 402 includes one or more processors 404 for generating a control signal associated with actively controlling a polarization of a generated magnetic field.

In an embodiment, the controller 402 is configured to actuate the actively-controllable magnetic field generator in response to the comparison of the detected nonlinear multi-harmonic response profile to one or more reference hemozoin nonlinear response profiles. In an embodiment, the controller 402 is configured to change at least one of a magnetic field ON duration, a magnetic field strength, a magnetic field frequency, and a magnetic field in response to the sensor's detection of a nonlinear multi-harmonic response profile associated with hemozoin nanoparticles in the biological sample. In an embodiment, the controller 402 is configured to change a magnetic field spatial distribution pattern in response to the sensor's detection of a nonlinear multi-harmonic response profile associated with hemozoin nanoparticles in the biological sample. In an embodiment, the controller 402 is configured to change a magnetic field temporal pattern in response to the sensor's detection of a nonlinear multi-harmonic response profile associated with hemozoin nanoparticles in the biological sample.

Circuitry can include, but is not limited to, one or more memories 414 that, for example, store instructions or data, for example, volatile memory (e.g., Random Access Memory (RAM) 416, Dynamic Random Access Memory (DRAM), or the like), non-volatile memory (e.g., Read-Only Memory (ROM) 418, Electrically Erasable Programmable Read-Only Memory (EEPROM), Compact Disc Read-Only Memory (CD-ROM), or the like), persistent memory, or the like. Further non-limiting examples of one or more memories 414 include Erasable Programmable Read-Only Memory (EPROM), flash memory, and the like. The one or more memories 414 can be coupled to, for example, one or more controllers 402 by one or more instruction, data, or power buses 420.

Circuitry can include, but is not limited to, one or more databases 422. In an embodiment, a database 422 includes at least one of reference hemozoin spectral response information, reference hemozoin nonlinear optical response information, heuristically determined parameters associated with at least one in vivo or in vitro determined metric. In an embodiment, a database 422 includes at least one of absorption coefficient data, extinction coefficient data, scattering coefficient data, and the like. In an embodiment, a database 422 includes at least one of stored reference data such as infectious agent marker data, and the like. In an embodiment, a database 422 includes information associated with a disease state of a biological subject. In an embodiment, a database 422 includes measurement data. In an embodiment, a database 422 includes at least one of cryptographic protocol information, regulatory compliance protocol information (e.g., FDA regulatory compliance protocol information, or the like), regulatory use protocol information, authentication protocol information, authorization protocol information, delivery regimen protocol information, activation protocol information, encryption protocol information, decryption protocol information, treatment protocol information, and the like. In an embodiment, a database 422 includes at least one of electromagnetic energy stimulus control delivery information, electromagnetic energy emitter control information, power control information, and the like.

In an embodiment, the system 100 is configured to compare an input associated with at least one characteristic associated with a biological subject to a database 422 of stored reference values, and to generate a response based in part on the comparison. In an embodiment, the system 100 is configured to compare an input associated with at least one characteristic associated the presence of hemozoin to a database 422 of stored reference values, and to generate a response based in part on the comparison.

In an embodiment, the system 100 includes circuitry 108 configured to detect a nonlinear multi-harmonic spectral response resulting from interrogating a biological sample suspected of having hemozoin with an electromagnetic energy stimulus.

The behavior of electric fields, magnetic fields, charge density, and current density can be described, for example, by Maxwell's equations. See e.g., Saleh et al., *Fundamentals of Photonics*, pp. 152-170 ($2^{nd}$ Edition; 2007). Nonlinear optical phenomena include, among other things, those interactions of electromagnetic radiation with matter where the response of the matter (e.g., polarization, power absorption, or the like) is not linearly proportional (i.e., the amount of the response does not scale linearly) to the variables describing the electromagnetic radiation (e.g., irradiance, electric field strength, energy flux, fundamental wavelength, fundamental frequency, and the like). In an embodiment, the energy-emitting component 104 delivers an electromagnetic energy stimulus to one or more focal volumes suspected of containing hemozoin. Depending on the character and duration of the electromagnetic energy, the interaction of the electromagnetic stimulus with hemozoin within the one or more focal volumes results in the generation of a nonlinear optical response that is detected via, for example, scattered radiation.

Nonlinear optical phenomena include, among other things, second harmonic generation (generation of light with a doubled frequency; one-half the wavelength of a fundamental wavelength emitted by an electromagnetic energy source), third harmonic generation (generation of light with a tripled frequency; one-third the wavelength of a fundamental wavelength emitted by an electromagnetic energy source), fourth harmonic generation, difference frequency generation, high harmonic generation, optical parametric amplification, optical parametric generation, optical parametric oscillation, optical rectification, spontaneous parametric down conversion, sum frequency generation, and the like. Further non-limiting examples of nonlinear optical phenomena include Brillouin scattering, multiple photo-ionization, optical Kerr effect, two-photon absorption, and the like.

The polarization density relationship describing the interaction of electromagnetic radiation with matter can be approximated (for sufficiently weak fields, assuming no permanent dipole moments are present) by the following sum of linear and nonlinear parts (see e.g., Saleh et al., *Fundamentals of Photonics*, pp. 873-935 ($2^{nd}$ Edition; 2007):

$$P_i(E) = (\epsilon_0 \chi_{ij}^{(1)} E_j + 2\chi_{ijk}^{(2)} E_j E_k + 4\chi_{ijkl}^{(3)} E_j E_k E_l + \ldots)$$ (eq. 1)

where, $\epsilon_0 \chi_{ij}^{(1)} E_j$ describes the linear first order optical phenomena including absorption and refraction;

$2\chi_{ijk}^{(2)} E_j E_k$ describes the second order nonlinear phenomena including electro-optic rectification, Pockels electro-optic effect, and second-harmonic generation (e.g., frequency doubling); and $4\chi_{ijkl}^{(3)} E_j E_k E_l$ describes the third order nonlinear phenomena including electric field-induced optical rectification, four-wave mixing, intensity-dependent refractive index, quadratic Kerr effect, self-focusing, and third-harmonic generation (e.g., frequency tripling).

In an embodiment, the circuitry 108 configured to detect the nonlinear multi-harmonic response energy includes a sensor component 440 including one or more sensors. In an embodiment, the sensor component 440 is configured to detect a nonlinear multi-harmonic response profile associated with hemozoin nanoparticles interrogated by an electromagnetic energy stimulus, and configured to compare the detected nonlinear multi-harmonic response profile to one or more reference hemozoin nonlinear response profiles. In an embodiment, the reference hemozoin response profile includes one or more heuristically determined parameters associated with at least one in vivo or in vitro determined metric. In an embodiment, the one or more heuristically determined parameters include at least one of a threshold level or a target parameter. In an embodiment, the one or more heuristically determined parameters include threshold information.

In an embodiment, the sensor component 440 includes an optical energy sensor component configured to detect scattered optical energy from the plurality of hemozoin nanoparticles interrogated by the multi-mode dark-field interrogation stimulus in the presence of the magnetic field.

In an embodiment, the sensor component 440 includes an electromagnetic energy sensor component configured to detect, via a dark-field detection configuration, response energy associated with hemozoin nanoparticles interrogated by the multi-mode dark-field stimulus in the presence of the first electromagnetic energy stimulus. The system 100 can include, among other things, circuitry 110 configured to generate at least one of a multi-mode dark-field interrogation stimulus and a multi-mode Rheinberg interrogation stimulus.

In practice, a dark-field detection configuration includes blocking out of central electromagnetic energy rays (via, for example, a dark-field stop or an opaque object) along an optical axis on an objective lens assembly 114, which ordinarily pass through and around a sample. Blocking the central electromagnetic energy rays allows only those oblique rays originating at large angles (i.e., only light scattered by the biological sample within the focal volume) to reach the detector. In an embodiment, the dark-field detection configuration includes a compound microscope assembly including a condenser system enabling electromagnetic energy rays emerging from a focal region in all azimuths to form an inverted hollow cone of illumination having an apex centered in the specimen plane. Dark-field illumination detection techniques can be further enhanced in contrast and selectivity by adding orthogonal (or crossed) polarizers to the illuminator and detector. Cross polarization limits detection to scattering events that depolarize the illumination, greatly reducing false positives and unwanted signal from healthy tissue. This is relevant for both imaging and spectroscopic, in vivo and in vitro system, devices, and methods.

In an embodiment, the sensor component 440 includes an electromagnetic energy sensor component configured to detect, via a Rheinberg detection configuration, response energy associated with hemozoin nanoparticles interrogated by the multi-mode dark-field stimulus in the presence of the first electromagnetic energy stimulus. In practice, a Rheinberg detection configuration resembles a dark-field detection configuration, but rather that using a dark-field stop, an opaque object, etc., along an optical axis; the Rheinberg detection configuration includes a Rheinberg filter of at least two different colors. In an embodiment, the central area, where the dark-field stop would typically reside, is one color (e.g., green) and the outer ring (annulus) a contrasting color (e.g., red). Unmodified light (light that does not impinge on the sample) fills the background with uniform light the color of the central circle, while modified light (light that impinges on the sample and is refracted, scattered, etc.) would have the color of the outer annulus.

In an embodiment, the electromagnetic energy sensor component includes at least one Rheinberg filter. In an embodiment, the electromagnetic energy sensor component is configured to detect scatter energy associated with hemozoin nanoparticles interrogated by the multi-mode dark-field stimulus in the presence of a first electromagnetic energy stimulus or a second electromagnetic energy stimulus. In an embodiment, the electromagnetic energy sensor component includes at least one spectrometer. In an embodiment, the electromagnetic energy sensor component is configured to detect a spectral response associated with hemozoin nanoparticles interrogated by the multi-mode dark-field stimulus in the presence of the first electromagnetic energy stimulus or the second electromagnetic energy stimulus.

In an embodiment, the electromagnetic energy sensor component is configured to detect scatter energy associated with hemozoin nanoparticles interrogated by the multi-mode dark-field stimulus in the presence of the first electromagnetic energy stimulus or the second electromagnetic energy stimulus.

The system 100 can include, among other things, a sensor component 440 including at least one sensor configured to detect nonlinear multi-harmonic response energy associated with hemozoin nanoparticles within at least one focal volume of a biological tissue interrogated by an electromagnetic energy stimulus. The system 100 can include, among other things, a controller 402 operably coupled to at least one sensor of the sensor component 440 and the energy-emitting component 104, the controller 402 configured to provide a control signal to an energy-emitting component.

The system 100 can include, among other things, an energy-emitting component 104 configured to deliver an effective amount of a electromagnetic energy stimulus to elicit a nonlinear optical response from hemozoin nanoparticles within the biological tissue, the elicited nonlinear response of a character and for a duration sufficient to modulate a biological activity of a malarial infectious agent within the biological tissue. In an embodiment, the elicited nonlinear response includes one or more peak emission wavelengths ranging from about 175 nanometers to about 650 nanometers. In an embodiment, the elicited nonlinear response includes one or more peak emission wavelengths ranging from about 250 nanometers to about 270 nanometers. In an embodiment, the elicited nonlinear response includes a peak emission wavelengths of about 260 nanometers.

In an embodiment, the elicited nonlinear response is of a character and for a duration sufficient to induce programmed cell death of a plasmodium parasite including the hemozoin nanoparticles. Many eukaryotic cells, including some unicellular organisms, undergo one or more forms of programmed cell death. Programmed cell death can be induced either by a stimulus such as, for example, non-repairable damage to the cell, infection, starvation, exposure to ionizing radiation, heat or toxic chemicals, or by removal of a repressor agent. The initiation of programmed cell death in response to specific stimuli may represent a favorable adaptation by the organism and may confer advantage during an organism's life-cycle. In the case of plasmodium parasite, for example, programmed cell death of a subset of the parasite population could be a means for preventing early death of the infected host, providing the parasite sufficient time to develop and be transmitted to another vector or host (see, e.g., Deponte & Becker, *Trends Parasitol.*, 20:165-169, 2004, which is incorporated herein by reference). By contrast, necrosis is defined as uncontrolled cell death that results from extreme physical or chemical insult to the cell. Necrosis can be induced by mechanical damage, hypoxia, complement-mediated cell lysis, high temperature, and exposure to highly toxic agents. Necrosis is more likely to provoke an inflammatory response in the host as a result of catastrophic disruption of the cell.

Various types of programmed cell death have been described including, but not limited to, apoptosis, autophagy, oncosis, pyroptosis and paraptosis. Apoptosis is characterized by a series of biochemical events leading to changes in cell morphology and ultimately cellular death. The characteristic changes in cell morphology associated with apoptosis include but not limited to blebbing and fragmentation of the nucleus, formation of apoptotic bodies, changes to the cell membrane such as loss of membrane asymmetry and attachment, cell shrinkage and rounding, changes in cytoplasm density, nuclear fragmentation, chromatin condensation, chromosomal DNA fragmentation, oxidative stress, the release of proteins (e.g., cytochrome c) from the mitochondria into the cytosol, the selective cleavage of proteins by proteases (especially caspases), and the activity of the proteases themselves. In contrast, autophagy is a catabolic process involving the degradation of a cell's own components through the lysosomal machinery, characterized by the formation of large vacuoles which digest away the cellular organelles in a specific sequence prior to destruction of the nucleus. Oncosis is a regulated response to severe DNA damage leading to energy depletion, organelle swelling and cell membrane disruption. Pyroptosis is a pro-inflammatory cell death pathway induced by intracellular bacteria in phagocytic cells and differs from the anti-inflammatory pathways of apoptosis. Paraptosis is morphologically similar to necrosis with formation of cytoplasmic vacuoles and mitochondrial swelling but requires new RNA and protein synthesis, consistent with a programmed biochemical event. See, e.g., Durand & Coetzer, *Bioinform. Biol. Insights* 2:101-117, 2008, which is incorporated herein by reference.

Programmed cell death akin to apoptosis has been observed in plasmodium parasites. For example, cultured ookinetes of *Plasmodium berghei* exhibit multiple markers for apoptosis-like programmed cell death including loss of mitochondrial membrane potential, nuclear chromatin condensation, DNA fragmentation, translocation of phosphatidylserine to the outer surface of the cell membrane and caspase-like activity (see, e.g., Arambage, et al., *Parasit. Vectors* 2:32, 2009, which is incorporated herein by reference). While the genomes of plasmodium parasites appear to lack homologs of the mammalian caspases, other proteases including metacaspases and calpain may play a role in mediating programmed cell death in plasmodium parasites (see, e.g., Wu et al., *Genome Res.*, 13:601-616, 2003; Chat et al., *Mol. Biochem. Parasitol.*, 153:41-47, 2007, which are incorporated herein by reference).

Programmed cell death akin to autophagy has also been observed in plasmodium parasites. For example, treatment of blood stage *Plasmodium falciparum* with S-nitroso-N-acetyl-penicillamine (SNAP), staurosporine, and chloroquine inhibits parasitemia and induces autophagy-like morphology with vacuolization of cellular components (see, e.g., Totino, et al., *Exp. Parasitol.*, 118:478-486, 2008, which is incorporated herein by reference).

Programmed cell death can be induced by heat-shock or acute exposure to temperatures above the normal physiological range of the organism. Hyperthermia therapy between 40° C. and 60° C. can result in disordered cellular metabolism and membrane function and in many instances, cell death. In general, at temperatures below 60° C., hyperthermia is more likely to induce programmed cell death without substantially inducing necrosis. At temperatures greater than about 60° C., the likelihood of inducing coagulation necrosis of cells and tissue increases. Relatively small increases in temperature, e.g., 3° C., above the normal functioning temperature of a cell can cause programmed cell death. For example, temperatures ranging from 40° C. to 47° C. can induce cell death in a reproducible time and temperature dependent manner in cells normally functioning at 37° C. Elevating the temperature of a mammalian cell, for example, to 43° C. can cause changes in cellular protein expression and increased programmed cell death. See, e.g., Somwaru, et al., *J. Androl.* 25:506-513, 2004; Stankiewicz, et al., *J. Biol. Chem.* 280:38729-38739, 2005; Sodja, et al., *J. Cell Sci.* 111:2305-2313, 1998; Setroikromo, et al., *Cell Stress Chaperones* 12:320-330, 2007; Dubinsky, et al., *AJR* 190:191-199, 2008; Lepock. *Int. J. Hyperthermia*, 19:252-266, 2003; Roti Roti *Int. J. Hyperthermia* 24:3-15, 2008; Fuchs, et al., "The Laser's Position in Medicine" pp 187-198 in *Applied Laser Medicine*. Ed. Hans-Peter Berlien, Gerhard J. Muller, Springer-Verlag New York, LLC, 2003; which are all incorporated herein by reference.

*Plasmodium* parasites are also susceptible to programmed cell death in response to hyperthermia therapy. For example, established isolates of *Plasmodium falciparum* as well as wild isolates derived from patients with malaria fail to grow at a culture temperature of 40° C., with schizonts exhibiting chromatin condensation (pyknosis) and hyposegmentation (see Kwiatkowski, *J. Exp. Med.* 169:357-361, 1989, which is incorporated herein by reference). It is suggested that the marked inhibition of *Plasmodium falciparum* growth at elevated temperature is due to disruption of the latter half of the asexual erythrocytic cycle, with developing schizonts particularly vulnerable to heat-shock. Treatment of erythrocyte stage *Plasmodium falciparum* at 40° C. also appears to induce cytoplasmic vacuolization and disruption of the parasite's food vacuole (see, e.g., Porter et al., *J. Parasitol.* 94:473-480, 2008). Exposure of *Plasmodium falciparum* to a temperature of 41° C. for as little as two minutes causes relative decreases in the number of parasites in the ring stage, trophozoite stage, and schizont stage measured 48 hours later by 20%, 70%, and 100%, respectively (see, e.g., Joshi et al., *FEBS* 312:91-94, 1992, which is incorporated herein by reference). Heating erythrocyte stage *Plasmodium falciparum* at 41° C. for 2, 8, and 16 hours reduces survival of the parasites by 23%, 66%, and 100%, respectively (see Oakley et al., *Infection Immunity* 75:2012-2025, 2007, which is incorporated herein by reference). The reduction in survival under these heat-shock conditions is accompanied by the appearance of "crisis forms" of the parasite and a time depend increase in positive terminal deoxynucleotidyltransferase-mediated dUTP-biotin nick end labeling (TUNEL) activity, indicators of programmed cell death. The response to heat-shock is also accompanied by changes in plasmodium parasite gene and protein expression suggesting that exposure to elevated temperature, e.g., 41° C., induces an organized signaling pathway involved in promoting programmed cell death as a response to elevated temperature. For example, mRNA and protein corresponding to the *Plasmodium falciparum* heat shock protein 70 (PfHSP-70) are elevated 7.42 fold and 3.7 fold, respectively in response to heat-shock at 41° C. A number of other parasite proteins are up or down regulated in response to hyperthermia including other stress proteins, DNA repair/replication proteins, histones, RNA processing proteins, secretion and trafficking proteins, and various serine/threonine protein kinases (see Oakley et al., *Infection Immunity* 75:2012-2025, 2007, which is incorporated herein by reference).

In some instances, programmed cell death in plasmodium parasites may be induced by exposure to one or more drugs. For example, the anti-malarial drug chloroquine concentrates in the plasmodium parasite food vacuole where it caps hemozoin molecules to prevent further biocrystallization of heme, leading to accumulation of heme in the parasite. Chloroquine complexed to heme is highly toxic to the plasmodium parasite and disrupts membrane function, causing cell lysis and ultimately parasite cell autodigestion. See, e.g., Orjih et al., *Science*, 214:667-669, 1981, which is incorporated herein by reference. In another example, treatment of erythrocyte stage *Plasmodium falciparum* with atovaquone reduces the number of detectable infected erythrocytes 2- to 3-fold with a concomitant loss in parasite mitochondrial membrane potential, a marker of programmed cell death (see Nyajeruga et al., *Microbes Infect.* 8:1560-1568, 2006, which is incorporated herein by reference). Treatment of erythrocyte stage *Plasmodium falciparum* with S-nitroso-N-acetyl-penicillamine (SNAP) induces abnormal parasite forms, "crisis forms", and DNA degradation, also markers of programmed cell death. The inhibition of plasmodium parasite growth and induction of plasmodium parasite death by various anti-malarial drugs may be accompanied by changes in the plasmodium parasite proteosome. For example, treatment of *Plasmodium falciparum* with artemisinin and chloroquine results in upregulation of 41 and 38 parasite proteins respectively (see, e.g., Prieto, et al., *PLoS ONE*, 3:e4098, 2008, which is incorporated herein by reference). In an embodiment, the system or device described herein can be used sequentially, or concurrently with anti-malarial drugs to, for example, induce programmed cell death in *Plasmodium falciparum*.

In an embodiment, the elicited nonlinear response is of a character and for a duration sufficient to cause a cellular stress, a cellular structural change (e.g., chromatin condescension, cell shrinkage, deoxyribonucleic acid fragmentation, etc.), activation of a caspases gene, or the like, associated with the induction of programmed cell death (e.g., apoptosis, death of a cell mediated by an intracellular program, or the like) of a cell, a host cell, a malarial infectious agent, or the like.

In an embodiment, the elicited nonlinear response is of a character and for a duration sufficient to generate antimicrobial energy. In an embodiment, nonlinear harmonic generation of ultraviolet radiation by hemozoin in a biological tissue (e.g., in vivo hemozoin) may permite irradiation of malaria parasites with antimicrobial energy. The incident electromagnetic energy stimulus can be focused and pulsed in order to increase the intensity to levels sufficient for effective harmonic generation. In an embodiment, the time-duty-cycle can be at a low enough level so that linear energy deposition of the incident light does not damage other tissues. The treatment can occur in vivo (e.g., transdermal, in-eye, via fiber optic, etc.) or ex vivo (e.g., blood flow through external device). In an embodiment, the electromagnetic energy stimulus includes a narrow-bandwidth light to increase the spectral brightness and hence the harmonic generation efficiency. In an embodiment, the electromagnetic energy is delivered via multiple pulses to increase total output. In an embodiment, phase-matched pulse-stacking is use to combine multiple beams/pulses at target site.

In an embodiment, the elicited nonlinear response is of a character and for a duration sufficient to generate a sterilizing energy stimulus having one or more peak emission wavelengths in the ultraviolet range. In an embodiment, the elicited nonlinear response is of a character and for a duration sufficient to induce programmed cell death of a host cell carrying the malarial infectious agent.

In an embodiment, the circuitry 108 configured to detect the nonlinear multi-harmonic response energy includes one or more electromagnetic sensors 442. Non-limiting examples of electromagnetic sensors 442 includes electromagnetic devices having a detectable response to received or absorbed electromagnetic energy. Electromagnetic sensors can include antennas (e.g., wire/loop antennas, horn antennas, reflector antennas, patch antennas, phased array antennas, or the like) solid-state photodetectors (e.g., photodiodes, charged-coupled devices, and photoresistors), vacuum photodetectors (e.g., phototubes and photomultipliers) chemical photodetectors (e.g., photographic emulsions), cryogenic photodetectors (e.g., bolometers), photoluminescent detectors (e.g., phosphor powders or fluorescent dyes/markers), micro-electro-mechanical systems (MEMS) detectors (e.g., microcantilever arrays with electromagnetically responsive materials or elements) or any other devices operable to detect and/or transduce electromagnetic energy.

In an embodiment, the circuitry 108 configured to detect the nonlinear multi-harmonic response energy includes one or more sensors 442 configured to detect a nonlinear response profile of one or more hemozoin nanoparticles interrogated by an electromagnetic energy stimulus. Non-limiting examples of sensor 442 include charge-coupled devices, complementary metal-oxide-semiconductor devices, photodiode image sensor devices, or whispering gallery mode micro cavity devices.

In an embodiment, the circuitry 108 configured to detect the nonlinear multi-harmonic response energy includes at least one of a time-integrating optical component, a linear time-integrating component, a nonlinear optical component, and a temporal auto-correlating component. In an embodiment, the circuitry 108 configured to detect the nonlinear multi-harmonic response energy includes one or more one-, two-, or three-dimensional photodiode arrays. In an embodiment, the circuitry 108 configured to detect the nonlinear multi-harmonic response energy includes one or more sensors 442 for detecting a nonlinear response profile of one or more hemozoin nanoparticles within the at least one focal volume. In an embodiment, the circuitry 108 configured to detect the nonlinear multi-harmonic response energy includes at least one charge-coupled device for detecting a nonlinear response profile of hemozoin nanoparticles within the at least one focal volume. In an embodiment, the circuitry 108 configured to detect the nonlinear multi-harmonic response energy includes at least one spectrometer configured to detect a nonlinear spectral response profile of hemozoin nanoparticles within the at least one focal volume. In an embodiment, the circuitry 108 configured to detect the nonlinear multi-harmonic response energy includes at least one ultraviolet-visible (UV-VIS) diode array detector for detecting a nonlinear response profile of hemozoin nanoparticles within the at least one focal volume. In an embodiment, the circuitry 108 configured to detect the nonlinear multi-harmonic response energy includes at least one high-sensitivity ultraviolet-visible (UV-VIS) diode array detector for detecting a nonlinear response profile of hemozoin nanoparticles within the at least one focal volume. In an embodiment, the circuitry 108 configured to detect the nonlinear multi-harmonic response energy includes circuitry configured to detect a transcutaneously emitted multi-harmonic photonic response (e.g., a nonlinear optical response to an electromagnetic energy stimulus).

In an embodiment, the circuitry 108 configured to detect the nonlinear multi-harmonic response energy includes a multiplet of sensors 442 operable at a corresponding multiplet of wavelengths or wavelength bands, i.e., a first sensor operable at a first wavelength/wavelength band, a second sensor operable at a second wavelength/wavelength band, etc. In an embodiment, the circuitry 108 configured to detect the nonlinear multi-harmonic response energy includes a focal plane array of sensors 442 or sensor multiplets (e.g., a Bayer or Foveon sensor).

In an embodiment, the circuitry 108 configured to detect the nonlinear multi-harmonic response energy includes a sensor component 440 configured to detect a nonlinear multi-harmonic response profile associated with hemozoin nanoparticles in a biological tissue within multiple focal volumes interrogated by a pulsed electromagnetic energy stimulus. In an embodiment, the circuitry 108 configured to detect the nonlinear multi-harmonic response energy includes at least one sensor 442 for detecting nonlinear multi-harmonic response energy associated with at least one of a second harmonic response, a third harmonic response, and a fourth harmonic response elicited by an electromagnetic energy stimulus (e.g., a pulsed electromagnetic energy stimulus, a spatially-patterned electromagnetic energy stimulus, a multiplexed electromagnetic energy stimulus, a spatially-patterned pulsed multiplexed electromagnetic energy stimulus, a temporally patterned electromagnetic energy stimulus, or the like).

In an embodiment, the circuitry 108 configured to detect the nonlinear multi-harmonic response energy includes an optical waveguide assembly 112 and at least one sensor 442 for collecting and detecting via an epi-collection mode at least one of a second harmonic response, a third harmonic response, and a fourth harmonic response elicited by the spatially-patterned pulsed multiplexed electromagnetic energy stimulus. The optical waveguide assembly 112 can take a variety of forms and configurations. In an embodiment, the optical waveguide assembly 112 includes one or more lenses, optical elements (e.g., a beamsplitter and lens), diffractive elements (e.g. Fresnel lenses), filters, polarizers, and the like to guide and shape electromagnetic radiation from a source (e.g., an energy-emitting component 104, a nonlinear optical response, and the like). In an embodiment, Dark-field illumination detection techniques can be further enhanced in contrast and selectivity by adding orthogonal (or crossed) polarizers to the illuminator and detector. Cross polarization limits detection to scattering events that depolarize the illumination, greatly reducing false positives and unwanted signal from healthy tissue. This is relevant for both imaging and spectroscopic, in vivo and in vitro system, devices, and methods.

Non-limiting examples of lenses include cylindrical graded index (GRIN) lenses, doublet or triplet lenses, that gather and shape electromagnetic radiation from a source (e.g., an energy-emitting component 104, a nonlinear optical response, and the like). Where the electromagnetic radiation source includes optical fibers that feed one or more lenses, the lenses are optionally bonded to or integral with the fibers.

In an embodiment, the optical waveguide assembly 112 includes one or more of polarization sensitive materials, chromatic correction, or other optical techniques for controlling the shape, phase, polarization, or other characteristics of the electromagnetic radiation. In an embodiment, the optical waveguide assembly 112, includes one or more polarizers, color filters, exit pupil expanders, chromatic correction elements, eye-tracking elements, and background masks may be incorporated for certain application as appropriate. In an embodiment, the optical waveguide assembly 112 includes at least one Rheinberg filter. In an embodiment, the optical waveguide assembly 112 includes an objective lens assembly 114 having a selectively controllable numerical aperture ranging from about 0.5 to about 1.4. In an embodiment, the circuitry 108 configured to detect the nonlinear multi-harmonic response energy includes a controller 402 for actively controlling a numerical aperture of an objective lens assembly 114 having a selectively controllable numerical aperture ranging from about 0.5 to about 1.4. In an embodiment, the system 100 includes an objective lens assembly 114 having a numerical aperture ranging from about 0.5 to about 1.4.

In an embodiment, the optical waveguide assembly 112 is configured to receive a portion of scattered radiation in a dark field collection configuration. In an embodiment, the optical waveguide assembly 112 is configured to receive a portion of scattered radiation in a Rheinberg collection configuration. In an embodiment, the optical waveguide assembly 112 is configured to receive a portion of scattered radiation in an epi-collection configuration. In an embodiment, the circuitry 108 configured to detect the nonlinear multi-harmonic response energy includes circuitry configured to detect, in situ, nonlinear multi-harmonic response energy associated with hemozoin nanoparticles within the at least one focal volume interrogated by the spatially-patterned pulsed multiplexed electromagnetic energy stimulus.

The system 100 can include, among other things, circuitry 116 configured to compare information associated with a detected nonlinear multi-harmonic response information to reference information configured as a data structure 424. The system 100 can include, among other things, circuitry 116 configured to compare information associated with a detected nonlinear multi-harmonic response information to reference hemozoin response information configured as a data structure 424. In an embodiment, the data structure 424 includes one or more heuristics. In an embodiment, the one or more heuristics include a heuristic for determining a rate of change associated with at least one physical parameter associated with a biological fluid. In an embodiment, the one or more heuristics include a heuristic for determining the presence of hemozoin nanoparticles. In an embodiment, the one or more heuristics include a heuristic for determining the presence of an infectious agent. In an embodiment, the one or more heuristics include a heuristic for determining at least one dimension of an infected tissue region. In an embodiment, the one or more heuristics include a heuristic for determining a location of an infection. In an embodiment, the one or more heuristics include a heuristic for determining a rate of change associated with a biochemical marker within the one or more focal volumes. In an embodiment, the one or more heuristics include a heuristic for determining a biochemical marker aggregation rate (e.g., a hemozoin aggregation rate, a hemozoin polymer aggregation rate, or the like). In an embodiment, the one or more heuristics include a heuristic for determining a type of biochemical marker. In an embodiment, the one or more heuristics include a heuristic for generating at least one initial parameter. In an embodiment, the one or more heuristics include a heuristic for forming an initial parameter set from one or more initial parameters. In an embodiment, the one or more heuristics include a heuristic for generating at least one initial parameter, and for forming an initial parameter set from the at least one initial parameter. In an embodiment, the one or more heuristics include at least one pattern classification and regression protocol.

In an embodiment, at least one data structure 424 includes information associated with at least one parameter associated with hemozoin nonlinear optical phenomena spectral information. For example, in an embodiment, a data structure 424 includes information associated with at least one parameter associated with at least one of hemozoin second harmonic response spectral information, hemozoin third harmonic response spectral information, and hemozoin fourth harmonic response spectral information.

The system 100 can include, but is not limited to, one or more computer-readable media drives 426, interface sockets, Universal Serial Bus (USB) ports, memory card slots, and the like, and one or more input/output components 428 such as, for example, a graphical user interface 430, a display, a keyboard 432, a keypad, a trackball, a joystick, a touch-screen, a mouse, a switch, a dial, and the like, and any other peripheral device. In an embodiment, the system 100 includes one or more user input/output components 428 that operably coupled to at least one controller 402 to control (electrical, electromechanical, software-implemented, firmware-implemented, or other control, or combinations thereof) at least one parameter associated with the energy delivery associated with the one or more energy-emitting components 104. The system 100 can include, but is not limited to, one or more modules optionally operable for communication with one or more input/output components 428 that are configured to relay user output and/or input. In an embodiment, a module includes one or more instances of electrical, electromechanical, software-implemented, firmware-implemented, or other control devices. Such device include one or more instances of memory 414, controllers 402, ports, valves 132, antennas, power, or other supplies; logic modules or other signaling modules; gauges or other such active or passive detection components; or piezoelectric transducers, shape memory elements, micro-electro-mechanical system (MEMS) elements, or other actuators.

The computer-readable media drive 426 or memory slot may be configured to accept signal-bearing medium (e.g., computer-readable memory media, computer-readable recording media, or the like). In an embodiment, a program for causing the system 100 to execute any of the disclosed methods can be stored on, for example, a computer-readable recording medium (CRMM) 434, a signal-bearing medium, and the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.), etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like.

In an embodiment, the system 100 includes signal-bearing media in the form of one or more logic devices (e.g., programmable logic devices, complex programmable logic device, field-programmable gate arrays, application specific integrated circuits, or the like) comprising, for example, a data structure 424 including one or more look-up tables. The system 100 can include, but is not limited to, signal-bearing media having reference hemozoin nonlinear response information configured as a data structure 424. In an embodiment, the data structure 424 includes at least one of malarial infection indication information, hemozoin spectral information, hemozoin optical response information, diseased state indication information, and diseased tissue indication information.

The system 100 can include among other things, one or more receivers 1206, transceivers 1208, transmitters 1210, or the like. In an embodiment, at least one of the one or more receiver 1206, transceivers 1208, and transmitters 1210, can be, for example, wirelessly coupled to a controller 402 that communicates with a control unit of the system 100 via wireless communication. In an embodiment, at least one of the one or more receivers 1206 and transceivers 1208 is configured to acquire information associated with a set of targets, biomarkers, or the like for detection. In an embodiment, at least one of the one or more receivers 1206 and transceivers 1208 is configured to acquire information associated with a set of physiological characteristic for detection. In an embodiment, at least one of the one or more receivers 1206 and transceivers 1208 is configured to acquire information associated with one or more physiological characteristics for detection. In an embodiment, at least one of the one or more receivers 1206 and transceivers 1208 is configured to acquire information associated with one or more hemozoin characteristics for detection.

In an embodiment, the system 100 includes at least one transceiver configured to report status information at a plurality of time intervals in response to the comparison. In an embodiment, the system 100 includes at least one transceiver configured to request reference hemozoin nonlinear response information in response to the comparison.

In an embodiment the system 100 includes a transmitter configured to send comparison information associated with a comparison of detected nonlinear multi-harmonic response energy to the reference hemozoin response profile. In an embodiment, at least one of a receiver and a transceiver is configured to obtain information regarding a target detection set of one or more characteristics associated with the biological subject. In an embodiment the system 100 includes at least one of a transmitter, a receiver, and a transceiver configured to acquire magnetization-induced nonlinear optical response information emitted by a biological sample. In an embodiment the system 100 includes at least on transceiver configured to concurrently or sequentially transmit or receive information.

The system 100 can include, among other things, circuitry 116 configured to compare information associated with a detected nonlinear multi-harmonic response energy to a reference hemozoin response profile. In an embodiment, the circuitry 116 configured to compare information associated with the detected nonlinear multi-harmonic response energy to the reference hemozoin response profile includes one or more computer-readable memory media having a reference hemozoin response profile configured as a data structure 424, the reference hemozoin response profile including at least one of hemozoin second harmonic response spectral information, hemozoin third harmonic response spectral information, and hemozoin fourth harmonic response spectral information. In an embodiment, the reference hemozoin response profile includes reference nonlinear response information indicative of a hemozoin nanoparticle aggregation rate. In an embodiment, the reference hemozoin response profile includes reference nonlinear response information indicative of a presence of a hemoglobin metabolite including a heme polymer.

In an embodiment, the reference hemozoin response profile includes reference hemozoin nanoparticle nonlinear susceptibility information.

In an embodiment, the circuitry 116 configured to compare the detected nonlinear multi-harmonic response energy to the reference hemozoin response profile includes one or more computer-readable memory media having a reference hemozoin response profile configured as a data structure 424, the reference hemozoin response profile including at least one of hemozoin nonlinear response information, hemozoin spectral information, and hemozoin nonlinear susceptibility information.

In an embodiment, the circuitry 116 configured to compare the detected nonlinear multi-harmonic response energy to the reference hemozoin response profile includes one or more computer-readable storage media including executable instructions stored thereon that, when executed on a computer, instruct a controller 402 to (a) retrieving from storage one or more parameters associated with reference hemozoin nonlinear response information; and to (b) perform a comparison of a detected nonlinear multi-harmonic response profile to the retrieved one or more parameter. In an embodiment, the one or more computer-readable storage media further include executable instructions stored thereon that, when executed on a computer, instruct a controller 402 to determine one or more of a presence, an absence, and a severity of malaria in response to the comparison.

In an embodiment, the circuitry 116 configured to compare the detected nonlinear multi-harmonic response energy to the reference hemozoin response profile includes a transmitter configured to send comparison information associated with a comparison of in situ detected nonlinear multi-harmonic response energy to the reference hemozoin response profile. In an embodiment, the circuitry 116 configured to compare the detected nonlinear multi-harmonic response energy to the reference hemozoin response profile includes a transceiver configured to receive a request to transmit at least one of hemozoin reference information, in situ detected nonlinear multi-harmonic response energy, and comparison information.

In an embodiment, the circuitry 116 configured to compare the detected nonlinear multi-harmonic response energy to the reference hemozoin response profile includes a transceiver configured to receive hemozoin filtering information. In an embodiment, the circuitry 116 configured to compare the detected nonlinear multi-harmonic response energy to the reference hemozoin response profile includes a transceiver configured to receive spatially-patterned pulsed multiplexed electromagnetic energy stimulus delivery parameter information. In an embodiment, the circuitry 116 configured to compare the detected nonlinear multi-harmonic response energy to the reference hemozoin response profile includes a transceiver configured to report status information at regular or irregular time intervals. In an embodiment, the circuitry 116 configured to compare the detected nonlinear multi-harmonic response energy to the reference hemozoin response profile includes circuitry configured to store paired and unpaired nonlinear multi-harmonic response data. In an embodiment, the circuitry 116 configured to compare the detected nonlinear multi-harmonic response energy to the reference hemozoin response profile includes at least one processor operable to cause a storing of information associated with comparing the nonlinear multi-harmonic response energy to the reference hemozoin response profile on one or more computer-readable storage media.

The system 100 can include, among other things, circuitry 120 configured to wirelessly communicate comparison information associated with comparing detected nonlinear multi-harmonic response energy to the reference hemozoin response profile.

The system 100 can include, among other things, circuitry 122 configured to selectively tune at least one of a wavelength distribution of the spatially-patterned pulsed multiplexed electromagnetic energy stimulus and a wavelength distribution of a collected in situ nonlinear multi-harmonic response.

The system 100 can include, among other things, circuitry 124 configured to generate a response based least in part on one or more comparisons between detected nonlinear multi-harmonic response energy and the reference hemozoin response profile. In an embodiment, the response includes at least one of a visual representation, an audio representation (e.g., an alarm, an audio waveform representation of a tissue region, or the like), a haptic representation, and a tactile representation (e.g., a tactile diagram, a tactile display, a tactile graph, a tactile interactive depiction, a tactile model (e.g., a multidimensional model of an infected tissue region, or the like), a tactile pattern (e.g., a refreshable Braille display), a tactile-audio display, a tactile-audio graph, or the like). In an embodiment, the response includes generating at least one of a visual, an audio, a haptic, and a tactile representation of at least one of biological sample spectral information, tissue spectral information, fat spectral information, muscle spectral information, bone spectral information, blood component spectral information, hemozoin spectral information and the like. In an embodiment, the response includes generating at least one of a visual, an audio, a haptic, and a tactile representation of at least one physical or biochemical characteristic associated with a biological subject. In an embodiment, the response includes generating at least one of a visual, an audio, a haptic, and a tactile representation of at least one physical or biochemical characteristic associated with a parasitic infection, a disease state, or the like In an embodiment, the response includes initiating one or more treatment protocols. In an embodiment, the response includes initiating at least one treatment regimen. In an embodiment, the response includes delivering an energy stimulus. In an embodiment, the response includes delivering an active agent. In an embodiment, the response includes concurrently or sequentially delivering an energy stimulus and an active agent. In an embodiment, the response includes at least one of a response signal, a control signal, a change to a treatment parameter, and the like.

In an embodiment, the response includes a change to a character of an electromagnetic energy stimulus. For example, in an embodiment, the response includes a change to at least one of a peak power, a peak irradiance, a focal spot size, a pulse width, a peak emission wavelength, and the like. In an embodiment, the response includes a change to at least one of an electromagnetic energy stimulus intensity, an electromagnetic energy stimulus frequency, an electromagnetic energy stimulus pulse frequency, an electromagnetic energy stimulus pulse ratio, an electromagnetic energy stimulus pulse intensity, an electromagnetic energy stimulus pulse duration time, an electromagnetic energy stimulus pulse repetition rate, and the like.

In an embodiment, the circuitry 124 configured to generate a response based least in part on one or more comparisons includes one or more receivers, transmitter, transceivers, and the like. In an embodiment, the circuitry 124 configured to generate a response based least in part on one or more comparisons includes at least one of a transmitter and a transceivers configured to send comparison information associated with a comparison of detected nonlinear multi-harmonic response energy to the reference hemozoin response profile.

In an embodiment, the circuitry 124 configured to generate a response based least in part on one or more comparisons includes at least one of a receiver and a transceiver configured to obtain reference hemozoin response profile information.

The system 100 can include, among other things, circuitry 126 configured to generate a magnetic field. In an embodiment, the circuitry 126 configured to generate the magnetic field includes a radio frequency transmitter configured to generate a radio frequency signal. In an embodiment, the circuitry 126 configured to generate the magnetic field includes a radio frequency transmitter configured to generate a radio frequency signal of a character and for a duration sufficient to magnetically align, in vivo, a plurality of hemozoin nanoparticles. In an embodiment, the 126 circuitry configured to generate the magnetic field includes one or more coils configured to generate one or more radio frequency pulses.

The system 100 can include, among other things, circuitry 128 configured to generate a magnetic field stimulus. In an embodiment, the circuitry 128 configured to generate the electromagnetic field stimulus includes a radio frequency transmitter configured to generate a radio frequency signal. In an embodiment, the circuitry 128 configured to generate the electromagnetic field stimulus includes one or more conductive traces configured to generating a magnetic field in the presence of an applied potential. In an embodiment, the circuitry 128 configured to generate the electromagnetic field stimulus includes one or more coils configured to generate one or more radio frequency pulses. In an embodiment, the circuitry 128 configured to generate the electromagnetic field stimulus includes a plurality of radio frequency coils. In an embodiment, the circuitry 128 configured to generate the electromagnetic field stimulus includes a plurality of coils configured to generate a time-varying magnetic field. In an embodiment, a generated electromagnetic field stimulus is of a character and for a duration sufficient to elicit hemozoin nanoparticles within a biological sample to deliver magnetically induced hyperthermia therapy in vivo. Because hemozoin nanoparticles are paramagnetic, in an embodiment, applying a magnetic field gradients can apply force to the hemozoin in malaria parasites. In an embodiment, applying a time varying magnetic fields to hemozoin can result in heating the hemozoin and hence the parasites; sufficient heat will kill them, while not being substantially affecting the normal function of other cells.

The system 100 can include, among other things, circuitry 130 configured to detect scattering information associated with a plurality of hemozoin nanoparticles interrogated by at least one of a multiplexed dark-field interrogation stimulus and a multiplexed Rheinberg interrogation stimulus in the presence of a magnetic field.

The system 100 can include, among other things, circuitry 128 configured to generate a magnetic field stimulus of a character and for a duration sufficient to elicit hemozoin nanoparticles within a biological sample to deliver magnetically induced hyperthermia therapy in vivo.

The system 100 can include, among other things, circuitry 132 configured to dynamically control the magnetic field stimulus. In an embodiment, the circuitry 132 configured to dynamically control the magnetic field stimulus includes one or more processors 404 operably coupled to the circuitry 128 configured to generate the electromagnetic field stimulus and configured to manage one or more parameters associated with deliver of a pulsed magnetic stimulus to a region of a biological subject. In an embodiment, the circuitry 132 configured to dynamically control the magnetic field stimulus includes one or more processors 404 configured to regulate at least one of a delivery regimen parameter, a spaced-apart delivery pattern parameter, and a temporal delivery pattern parameter associated with generating the electromagnetic field stimulus.

The system 100 can include, among other things, circuitry 134 configured to compare a detected scattering information to reference hemozoin dark-field scattering data. In an embodiment, the circuitry 134 configured to compare the nonlinear multi-harmonic response energy profile includes one or more computer-readable memory media having reference hemozoin nonlinear response information configured as a data structure. In an embodiment, the reference hemozoin nonlinear response information includes modeled reference comparison information. In an embodiment, the circuitry 134 configured to compare the nonlinear multi-harmonic response energy profile includes one or more computer-readable memory media having reference hemozoin nonlinear response information configured as a data structure. In an embodiment, the reference hemozoin nonlinear response information includes at least one of in situ detected nonlinear response information, hemozoin spectral information, and hemozoin nonlinear susceptibility information.

The system 100 can include, among other things, circuitry 136 configured to compare (a) a nonlinear multi-harmonic response energy profile associated with at least one focal volume interrogated with a spatially patterned pulsed electromagnetic energy stimulus to (b) reference hemozoin nonlinear response information.

The system 100 can include, among other things, circuitry 138 configured to magnetically induce at least one of an oscillation, a translation, and a rotation of hemozoin nanoparticles in a biological sample, the induced at least one of the oscillation, the translation, and the rotation of hemozoin nanoparticles in the biological sample of a character and for a duration sufficient to affect the integrity of an organelle of a plasmodium parasite. In an embodiment, the circuitry 138 configured to magnetically induce at least one of an oscillation, a translation, and a rotation of hemozoin nanoparticles in a biological tissue includes a flexible circuit having a one or more conductive traces configured to generate a magnetic field in the presence of an applied potential. In an embodiment, the circuitry 138 configured to magnetically induce at least one of an oscillation, a translation, and a rotation of hemozoin nanoparticles in a biological tissue includes a printed circuit having a one or more conductive traces configured to generate a magnetic field in the presence of an applied electrical current. In an embodiment, the circuitry 138 configured to magnetically induce at least one of an oscillation, a translation, and a rotation of hemozoin nanoparticles in a biological tissue includes at least one of a receiver, transmitter, and a transceiver. In an embodiment, the circuitry 138 configured to magnetically induce at least one of an oscillation, a translation, and a rotation of hemozoin nanoparticles in a biological tissue includes at least one electromagnet. In an embodiment, the circuitry 138 configured to magnetically induce at least one of an oscillation, a translation, and a rotation of hemozoin nanoparticles in a biological tissue includes at least one permanent magnet.

The system 100 can include, among other things, circuitry 140 configured to communicate comparison information associated with comparing the nonlinear multi-harmonic response energy profile.

The system 100 can include, among other things, circuitry 142 configured to communicate treatment information associated with magnetically inducing at least one of the oscillation, the translation, and the rotation of hemozoin nanoparticles.

The system 100 can include, among other things, circuitry 144 configured to detect a scattered energy from a biological tissue in at least one of a dark-field detection configuration and a Rheinberg detection configuration. In an embodiment, the circuitry 144 configured to detect the scattered energy includes at least one sensor configured to receive a portion of the scattered energy in a dark-field detection configuration. In an embodiment, the circuitry 144 configured to detect the scattered energy includes at least one sensor configured to receive a portion of the scattered energy in a Rheinberg detection configuration. In an embodiment, the circuitry 144 configured to detect the scattered energy includes a lens array assembly configured receive at least a portion of the scattered energy from the biological subject. In an embodiment, the circuitry 144 configured to detect the scattered energy includes a Rheinberg differential color illumination assembly configured receive at least a portion of the scattered energy from the biological subject. In an embodiment, the circuitry 144 configured to detect the scattered energy includes at least one Rheinberg filter.

The system 100 can include, among other things, circuitry 146 configured to magnetically perturb hemozoin nanoparticles in a biological tissue in response to a comparison between detected scattered energy information and reference hemozoin nanoparticles scattered energy information. In an embodiment, the circuitry 146 configured to magnetically perturb hemozoin nanoparticles in a biological tissue includes a coil assembly configured to magnetically induce at least one of an oscillation, a translation, and a rotation of hemozoin nanoparticles in a biological tissue. In an embodiment, the circuitry 146 configured to magnetically perturb hemozoin nanoparticles in a biological tissue includes one or more conductive traces configured to cause at least one of an oscillation, a translation, and a rotation of hemozoin nanoparticles in a biological tissue. In an embodiment, the circuitry 146 configured to magnetically perturb hemozoin nanoparticles in a biological tissue includes one or more processors 404 that, when activated, generate a control signal that causes the comparison between the detected scattered energy and the reference hemozoin nanoparticles scattered energy information.

The system 100 can include, among other things, circuitry 148 configured to impinge an effective amount of an electromagnetic energy stimulus in a dark-field configuration onto one or more regions of the biological tissue to produce scattered energy from the biological tissue. In an embodiment, the circuitry 148 configured to impinge the effective amount of an electromagnetic energy stimulus includes a lens array assembly configured to focus one or more incident electromagnetic energy stimuli onto the biological subject and to receive scattered energy therefrom.

The system 100 can include, among other things, circuitry 150 configured to detect a nonlinear multi-harmonic response energy associated with hemozoin nanoparticles within at least one focal volume of a biological tissue interrogated by an electromagnetic energy stimulus. In an embodiment, the circuitry 150 configured to detect the nonlinear multi-harmonic response energy includes at least one charged-coupled device configured to detect at least one of a second harmonic response, a third harmonic response, and a fourth harmonic response associated with hemozoin nanoparticles within at least one focal volume interrogated by an electromagnetic energy stimulus. In an embodiment, the circuitry 150 configured to detect the nonlinear multi-harmonic response energy includes at least one ultraviolet-visible diode array detector for detecting at least one of a second harmonic response, a third harmonic response, and a fourth harmonic response associated with hemozoin nanoparticles within at least one focal volume interrogated by an electromagnetic energy stimulus. In an embodiment, the circuitry 150 configured to detect the nonlinear multi-harmonic response energy includes circuitry configured to detect a transcutaneously emitted multi-harmonic photonic response.

In an embodiment, the circuitry 150 configured to detect the nonlinear multi-harmonic response energy includes one or more sensors 442 for detecting a nonlinear response profile of one or more hemozoin nanoparticles within the at least one focal volume. In an embodiment, the circuitry 150 configured to detect the nonlinear multi-harmonic response energy includes one or more sensors 442 for detecting a spectral response of one or more hemozoin nanoparticles within the at least one focal volume. In an embodiment, the circuitry 150 configured to detect the nonlinear multi-harmonic response energy includes circuitry configured to detect, in situ, nonlinear multi-harmonic response energy associated with hemozoin nanoparticles within the at least one focal volume interrogated by the spatially patterned pulsed multiplexed electromagnetic energy stimulus. In an embodiment, the circuitry 150 configured to detect the nonlinear multi-harmonic response energy includes an optical waveguide assembly and at least one sensor for collecting and detecting via an epi-collection mode at least one of a second harmonic response, a third harmonic response, and a fourth harmonic response elicited by the spatially patterned pulsed multiplexed electromagnetic energy stimulus. In an embodiment, the circuitry 150 configured to detect the nonlinear multi-harmonic response energy includes an optical waveguide assembly and at least one sensor for collecting and detecting via a Rheinberg detection configuration at least one of a second harmonic response, a third harmonic response, and a fourth harmonic response elicited by the spatially patterned pulsed multiplexed electromagnetic energy stimulus.

The system 100 can include, among other things, circuitry 152 configured to generate an effective amount of a pulsed electromagnetic energy stimulus to elicit a nonlinear response from hemozoin nanoparticles in a biological tissue within the at least one focal volume of the biological tissue. In an embodiment, the elicited nonlinear response is of a character and for a duration sufficient to modulate a biological activity of a malarial infectious agent.

Absorption, transmission, scattering, etc., of electromagnetic radiation varies among biological tissues, biological samples, equipment, other materials, and the like. For example, the range of about 800 nanometers to about 1300 nanometers is a range where photon absorption and scattering are minimal for dermal tissue (creating a region that is optimal for efficient optical power transfer across the skin). Accordingly, in an embodiment, the peak emission wavelength of the electromagnetic stimulus generated by the energy-emitting component 104 is chosen to maximize the delivery and detection to and from a sample of interest. For example, to improve transcutaneous transmission of an electromagnetic stimulus of and subsequent detection of a generated nonlinear optical response, a peak emission wavelength of electromagnetic stimulus is chosen within a range of about 1000 nanometers to about 1300 nanometers. This will results in a nonlinear optical response from hemozoin ranging from about 500 nanometers to about 650 nanometers (for second harmonic generation; one-half the wavelength); from about 333 nanometers to about 433 nanometers (for third harmonic generation; one-third the wavelength), etc. In an embodiment, one or more peak emission wavelengths of the electromagnetic stimulus generated by the energy-emitting component 104 are chosen to elicit a nonlinear optical response of hemozoin to emit within a wavelength range that damages genetic material. Other ranges may be more optimal for efficient optical power transfer across, for example, medical equipment, medical settings, in vitro ware, or the like.

In an embodiment, the circuitry 152 configured to generate the effective amount of a pulsed electromagnetic energy stimulus includes at least one of a first energy emitter having a peak emission wavelength ranging from about 690 nanometers to about 2100 nanometers and at least one of a second energy emitter having a peak emission wavelength ranging from about 1000 nanometers to about 2000 nanometers for multiplex nonlinear response assaying. In an embodiment, the circuitry 152 configured to generate the effective amount of a pulsed electromagnetic energy stimulus includes an energy-emitting component 104 configured to interrogate at least one focal volume with a spatially patterned pulsed multiplexed electromagnetic energy stimulus.

In an embodiment, the circuitry 152 configured to generate the effective amount of a pulsed electromagnetic energy stimulus includes one or more lasers, laser diodes, and light-emitting diodes. In an embodiment, the circuitry 152 configured to generate the effective amount of a pulsed electromagnetic energy stimulus includes one or more quantum dots, organic light-emitting diodes, microcavity light-emitting diodes, and polymer light-emitting diodes. In an embodiment, the circuitry 152 configured to generate the effective amount of a pulsed electromagnetic energy stimulus includes one or more femtosecond lasers. In an embodiment, the circuitry 152 configured to generate the effective amount of a pulsed electromagnetic energy stimulus includes a patterned energy-emitting source. In an embodiment, the circuitry 152 configured to generate the effective amount of a pulsed electromagnetic energy stimulus includes a lens array configured to deliver a spaced-apart energy stimuli having at least a first region and a second region, the second region having a focal depth different from the first region.

The system 100 can include, among other things, circuitry 154 configured to generate a multiplexed pulsed electromagnetic energy stimulus having a peak power ranging from about 400 gigawatts to about 8 terawatts.

The system 100 can include, among other things, circuitry 156 configured to direct the multiplexed pulsed electromagnetic energy stimulus on a plurality of focal volumes in a biological subject.

The system 100 can include, among other things, circuitry 158 configured to detect a multi-harmonic response associated with a plurality of hemozoin nanoparticles in a biological tissue within one or more of the plurality of focal volumes interrogated by the multiplexed pulsed electromagnetic energy stimulus. In an embodiment, the circuitry 158 configured to detect the multi-harmonic response includes at least one epi-direction sensor for detecting, in situ, an emitted multi-harmonic response associated with the plurality of hemozoin nanoparticles in a biological tissue interrogated by the multiplexed pulsed electromagnetic energy stimulus.

The system 100 can include, among other things, a magnetic field component 160 configured to generate a magnetic field of a character and for a duration sufficient to magnetically align, in vivo, a plurality of hemozoin nanoparticles. In an embodiment, the magnetic field component 160 includes a radio frequency transmitter configured to generate a radio frequency signal. In an embodiment, the magnetic field component 160 includes one or more coils configured to generate one or more radio frequency pulses. In an embodiment, the medical diagnostic device is configured for removable attachment to a biological surface of a biological subject.

The system 100 can include, among other things, a physical coupling element configured to removably-attach at least one of the dark-field electromagnetic energy emitting component, the magnetic field component, and the optical energy sensor component to a biological surface of a biological subject.

The system 100 can include, among other things, an actively-controllable magnetic field generator 162 configured to deliver a varying magnetic field stimulus at a dose sufficient to cause heat generation from hemozoin nanoparticles within a biological sample. In an embodiment, the actively-controllable magnetic field generator 162 includes circuitry configured to generate and deliver an electromagnetic energy stimulus of a character and for a duration sufficient to cause hemozoin nanoparticles within the biological sample interrogated by an electromagnetic energy stimulus to generate thermal energy. In an embodiment, the actively-controllable magnetic field generator 162 includes an electrical coil assembly that, when energized, generates a magnetic field of a character and for a duration to induce one or more of the Brownian process and the Neélian process within the biological sample including hemozoin nanoparticles. In an embodiment, the actively-controllable magnetic field generator 162 includes a magnetic field generating coil assembly for applying a varying magnetic field. In an embodiment, the actively-controllable magnetic field generator 162 includes a volume coil arrangement including a plurality of coils for generating a circularly polarized magnetic field. In an embodiment, the actively-controllable magnetic field generator 162 includes one or more electromagnets.

In an embodiment, the actively-controllable magnetic field generator 162 includes one or more alternating current electromagnets. In an embodiment, the actively-controllable magnetic field generator 162 includes one or more coils that are configured to generate a magnetic field of a character and for a duration sufficient to increase the temperature of a region within a plasmodium parasite including the hemozoin nanoparticles by about 3° C. to about 22° C. In an embodiment, the actively-controllable magnetic field generator 162 includes one or more coils that are configured to generate a magnetic field of a character and for a duration sufficient to increase the temperature of a hemozoin-containing-region within a plasmodium parasite existing within the biological sample by about 3° C. to about 10° C. In an embodiment, the actively-controllable magnetic field generator 162 includes one or more coils that are configured to generate a magnetic field of a character and for a duration sufficient to increase the temperature of a region within a plasmodium parasite including the hemozoin nanoparticles by about 3° C. to about 4° C.

In an embodiment, the actively-controllable magnetic field generator 162 is configured to generate a magnetic field of a character and for a duration sufficient to cause a temperature increase within a region of a plasmodium parasite including the hemozoin nanoparticles. In an embodiment, the actively-controllable magnetic field generator 162 is configured to generate a magnetic field of a sufficient strength or duration to attenuate an activity of a malarial infectious agent. In an embodiment, the actively-controllable magnetic field generator 162 is configured to provide a magnetic field of a sufficient strength or duration to modulate heme polymerase activity of a malarial infectious agent.

In an embodiment, the actively-controllable magnetic field generator 162 is configured to provide a magnetic field of a character and for a duration sufficient to ameliorate a plasmodium parasitic effect without substantially disrupting the integrity of an erythrocyte encapsulating a plasmodium parasite. In an embodiment, the actively-controllable magnetic field generator 162 is configured to provide a magnetic field of a character and for a duration sufficient to cause a temperature increase within a region of a plasmodium parasite in the biological sample, the temperature increase sufficient to cause heat-induced programmed cell death in the plasmodium parasite.

In an embodiment, the actively-controllable magnetic field generator 162 is configured to provide a magnetic field of a character and for a duration sufficient to cause programmed cell death of a host cell carrying the malarial infectious agent. In an embodiment, the actively-controllable magnetic field generator 162 is configured to provide a magnetic field of a character and for a duration sufficient to cause a temperature increase within a region of a plasmodium parasite in the biological sample, the temperature increase sufficient to reduce a parasitemia level. In an embodiment, the actively-controllable magnetic field generator 162 is configured to generate an alternating current magnetic field of a character and for a duration sufficient to cause a temperature increase in a region within a plasmodium parasite including the hemozoin nanoparticles and to ameliorate a plasmodium parasitic effect without substantially disrupting the integrity of an erythrocyte encapsulating the plasmodium parasite.

In an embodiment, the actively-controllable magnetic field generator 162 includes one or more conductive coils configured to generate a time-varying magnetic field in response to an applied current, the time-varying magnetic field of a character and for a duration sufficient to cause hemozoin nanoparticles within the biological sample to generate heat as a result of one or more of the Brownian process and the Neélian process. In an embodiment, the actively-controllable magnetic field generator 162 generates a magnetic field of a character and for a duration sufficient to induce heat-damage to an organelle membrane within a plasmodium parasite within the biological sample. In an embodiment, the actively-controllable magnetic field generator 162 includes at least one radio frequency transmitter including one or more one radio frequency coils configured to generate a localized radio frequency stimulus.

In an embodiment, the actively-controllable magnetic field generator 162 is configured to concurrently or sequentially generate at least a first electromagnetic energy stimulus and a second electromagnetic energy stimulus, the first electromagnetic energy stimulus of a character and for a duration sufficient to magnetically align hemozoin nanoparticles in a biological tissue, the second electromagnetic energy stimulus of a character and for a duration sufficient to magnetically induce at least one of an oscillation, a translation, and a rotation of the hemozoin nanoparticles in the biological tissue. In an embodiment, the induced at least one of the oscillation, the translation, and the rotation of the hemozoin nanoparticles in a biological tissue is sufficient to affect an integrity of an organelle of a malarial infectious agent. In an embodiment, the induced at least one of the oscillation, the translation, and the rotation of the hemozoin nanoparticles in a biological tissue is sufficient to affect the integrity of a digestive food vacuole of a malaria parasite. In an embodiment, the induced at least one of the oscillation, the translation, and the rotation of the hemozoin nanoparticles in a biological tissue is sufficient to disrupt an in vivo heme polymerization process.

The system 100 can include, among other things, a controller 402 operatively coupled to the actively-controllable magnetic field generator. In an embodiment, the controller 402 includes one or more processors 404 for controlling at least one of a magnetic field ON duration, a magnetic field strength, a magnetic field frequency, and a magnetic field waveform.

The system 100 can include, among other things, a dark-field electromagnetic energy emitting component configured to interrogate at least one focal volume of biological tissue with a multi-mode dark-field stimulus.

The system 100 can include, among other things, one or more power sources 700. In an embodiment, the power source 700 is electromagnetically, magnetically, ultrasonically, optically, inductively, electrically, or capacitively coupleable to one or more energy-emitting components 104. In an embodiment, the power source 700 is carried by a monitor/treatment device 102. In an embodiment, the power source 700 comprises at least one rechargeable power source 702. In an embodiment, the power source 700 is configured to wirelessly receive power from a remote power supply.

In an embodiment, the monitor/treatment device 102 includes one or more biological-subject (e.g., human)-powered generators 704. In an embodiment, the biological-subject-powered generator 704 is configured to harvest energy from, for example, motion of one or more joints. In an embodiment, the biological-subject-powered generator 704 is configured to harvest energy generated by the biological subject using at least one of a thermoelectric generator 706, piezoelectric generator 708, electromechanical generator 710 (e.g., a microelectromechanical systems (MEMS) generator, or the like), biomechanical-energy harvesting generator 712, and the like.

In an embodiment, the biological-subject-powered generator 704 is configured to harvest thermal energy generated by the biological subject. In an embodiment, a thermoelectric generator 706 is configured to harvest heat dissipated by the biological subject. In an embodiment, the biological-subject-powered generator 704 is configured to harvest energy generated by any physical motion or movement (e.g., walking,) by biological subject. For example, in an embodiment, the biological-subject-powered generator 704 is configured to harvest energy generated by the movement of a joint within the biological subject. In an embodiment, the biological-subject-powered generator 704 is configured to harvest energy generated by the movement of a fluid (e.g., biological fluid) within the biological subject.

Among power sources 700 examples include, but are not limited to, one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, and the like. Further non-limiting examples of power sources 700 include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, and the like. In an embodiment, the monitor/treatment device 102 includes one or more generators configured to harvest mechanical energy from for example, ultrasonic waves, mechanical vibration, blood flow, and the like. In an embodiment, the monitor/treatment device 102 includes one or more power receivers 732 configured to receive power from an in vivo or ex vivo power source. In an embodiment, the in vivo power source includes at least one of a thermoelectric generator, a piezoelectric generator, an electromechanical energy to electricity generator, and a biomechanical-energy harvesting generator.

In an embodiment, the power source 700 includes at least one of a thermoelectric generator, a piezoelectric generator, an electromechanical generator, and a biomechanical-energy harvesting generator, and at least one of a button cell, a chemical battery cell, a fuel cell, a secondary cell, a lithium ion cell, a micro-electric patch, a nickel metal hydride cell, silver-zinc cell, a capacitor, a super-capacitor, a thin film secondary cell, an ultra-capacitor, and a zinc-air cell. In an embodiment, the power source 700 includes at least one rechargeable power source.

In an embodiment, a monitor/treatment device 102 includes a power source 700 including at least one of a thermoelectric generator a piezoelectric generator, an electromechanical generator, and a biomechanical-energy harvesting generator. In an embodiment, the power source 700 is configured to manage a duty cycle associated with emitting an effective amount of the electromagnetic energy stimulus from the one or more energy-emitting components 104. In an embodiment, the power source 700 is configured to manage a duty cycle associated with emitting an effective amount of a sterilizing energy stimulus from the one or more energy-emitting components 104.

In an embodiment, the power source 700 is configured to manage a duty cycle associated with magnetically inducing at least one of an oscillation, a translation, and a rotation of hemozoin nanoparticles in a biological tissue. In an embodiment, the power source 700 is configured to manage a duty cycle associated with comparing the nonlinear multi-harmonic response energy profile associated with at least one focal volume interrogated with the spatially patterned pulsed electromagnetic energy stimulus to reference hemozoin nonlinear response information. The system 100 can include, among other things, an energy storage device. In an embodiment, the energy storage device includes at least one of a battery, a capacitor, and a mechanical energy store.

Figure 2A:
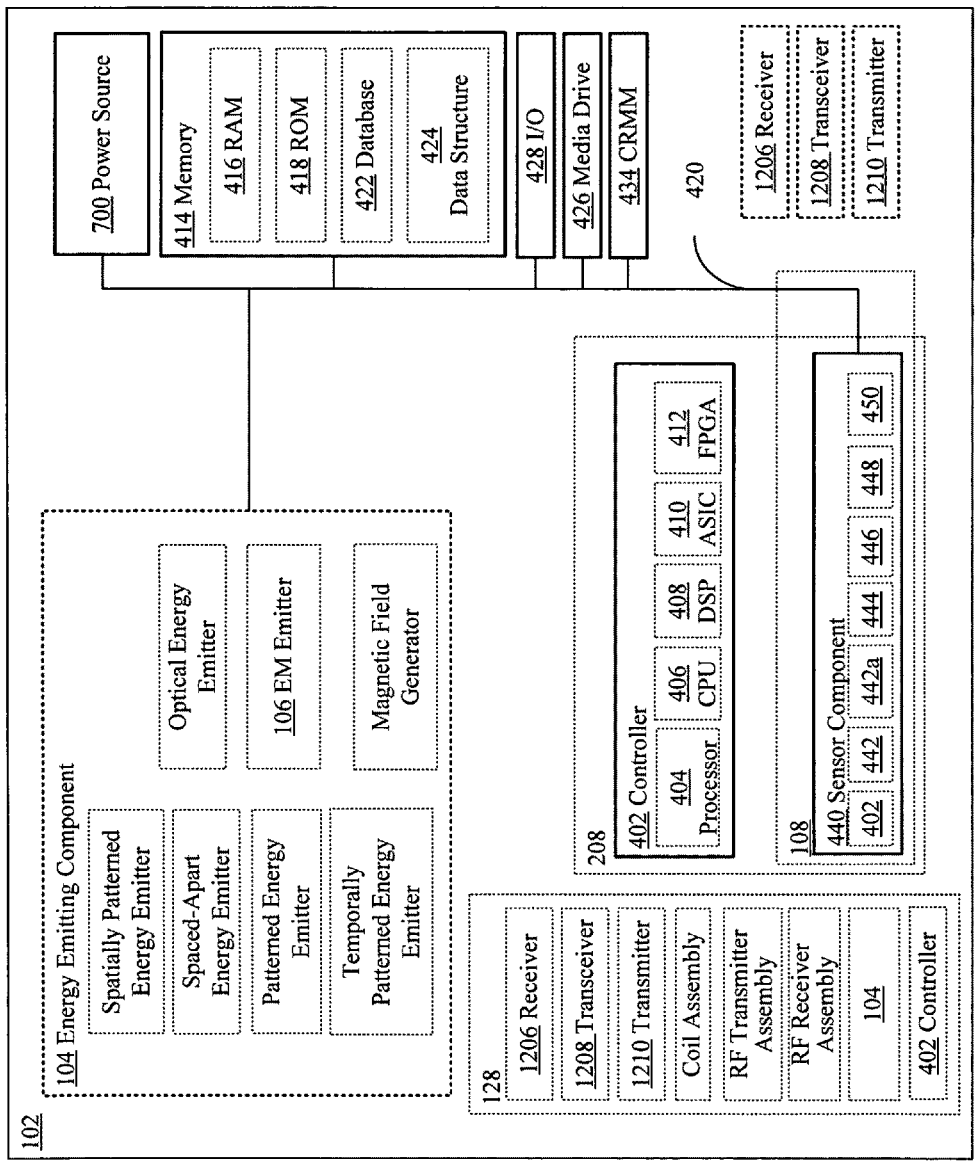
FIG. 2A is a perspective view of a system for modulating plasmodium parasitic activity according to one illustrated embodiment.

FIG. 2A shows a system 100 for modulating plasmodium parasitic activity. The system 100 for modulating plasmodium parasitic activity includes, among other things, circuitry 128 configured to generate a magnetic field stimulus of a character and for a duration sufficient to elicit hemozoin nanoparticles within a biological sample to deliver magnetically induced hyperthermia therapy in situ, in vitro, in vivo, or the like. In situ includes in vivo or in vitro. In an embodiment, the system 100 for modulating plasmodium parasitic activity includes circuitry 208 configured to dynamically control the magnetic field stimulus. In an embodiment, the circuitry 208 configured to dynamically control the magnetic field stimulus includes one or more processors 404 operably coupled to the circuitry 202 configured to generate the electromagnetic field stimulus and configured to manage one or more parameters associated with deliver of a pulsed magnetic stimulus to a region of a biological subject. In an embodiment, the circuitry 208 configured to dynamically control the magnetic field stimulus includes one or more processors 404 configured to regulate at least one of a delivery regimen parameter, a spaced-apart delivery pattern parameter, and a temporal delivery pattern parameter associated with generating the electromagnetic field stimulus.

Figure 2B:
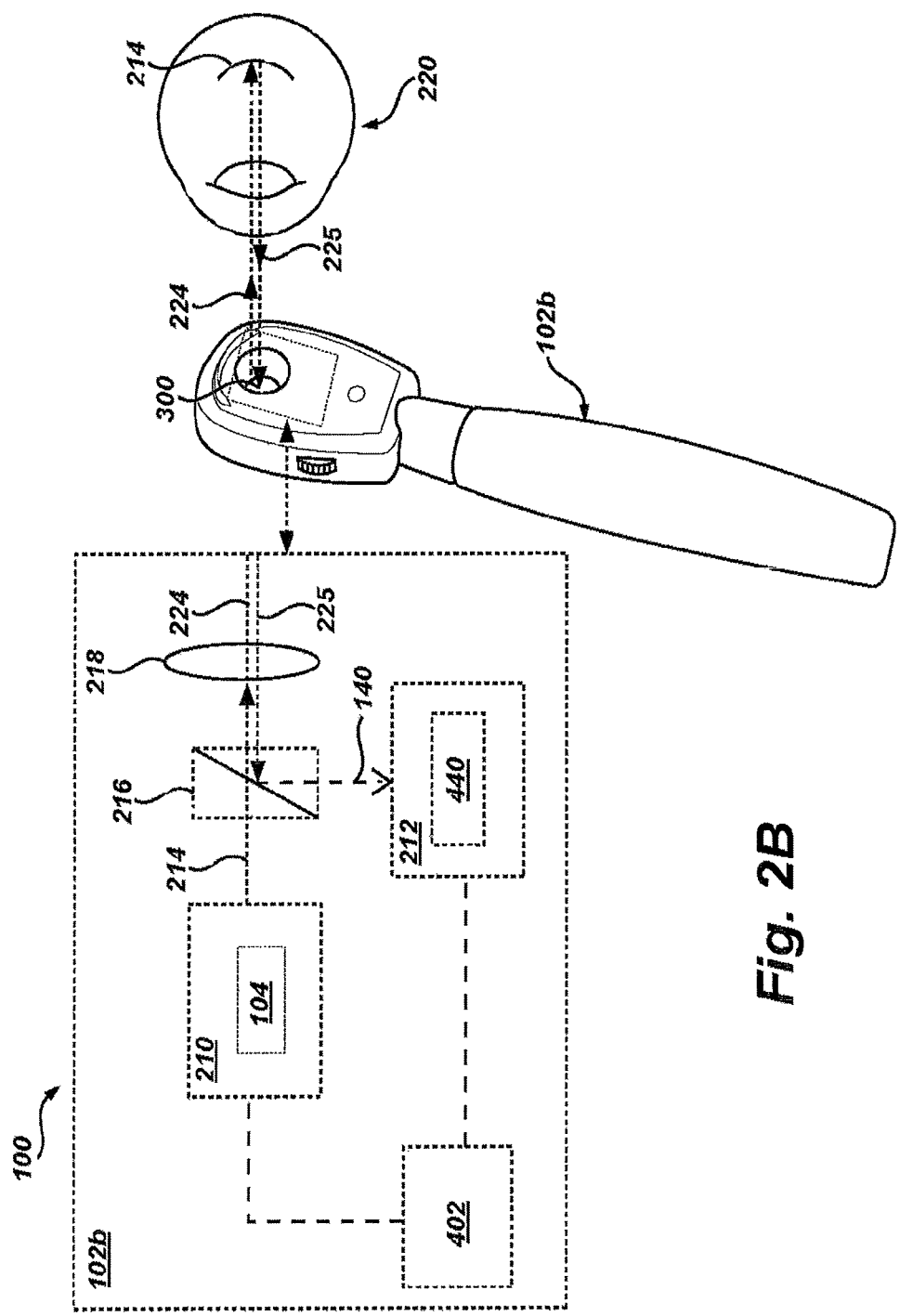
FIG. 2B is a perspective view of a system for monitoring/modulating a plasmodium parasitic activity according to one illustrated embodiment.

FIG. 2B shows a system 100 for optically monitoring/modulating a plasmodium parasitic activity. In an embodiment, the system 100 includes a scanning/projection system 210 and a detection subsystem 212 operating under at least one controller 402. The system 100 may be implemented in a variety of formats, such as, but not limited to, an optical scanner-based system, such as that described in one or more of U.S. Pat. No. 6,445,362, U.S. 2006/0284790 and/or U.S. 2005/0020926.

In one approach, the scanning/projection system 210 directs one or more electromagnetic energy stimuli 214 through a beam splitter 216 and through an optical lens assembly 218 toward a biological subject's eye 220. For example, the system 100 directs an effective amount of an electromagnetic energy stimulus 214 onto one or more focal volumes of a biological subject to produce scattered radiation from the biological subject, and detects using a dark field detection configuration at least a portion of the scattered radiation 225.

In an illustrative embodiment, the system 100 employs one or more energy-emitting components 104, such as laser diodes or fiber coupled lasers a having a peak emission wavelength ranging from about 690 nanometers to about 2100 nanometers, for at least one of the illuminating beams 214. The monitoring/modulating system 210 scans the illuminating beams 214 through a raster pattern or a Lissajous pattern, for example.

The optical lens assembly 218 couples the scanned illuminating beam 214 into the eye, through its pupil where the illuminating beam of light 214 strikes the retina 222. In some approaches, the optical lens assembly 218 may provide a beam 224 that converges in a field of interest, such as at or near the surface of a retina 222. In other approaches, the beam may be substantially collimated. The beam splitter 216 may be any of a variety of optical structures that can selectively transmit and/or re-direct at least a portion of light along one or more paths. In an illustrative embodiment, the beam splitter may be responsive to one or more wavelengths of light to selectively transmit and/or re-direct at least a portion of light. As will be described herein, some of the light that returns from the field of interest is collected using a differential illumination configuration. The beam splitter 216 may be configured to selectively transmit to the eye light at an input wavelength, while selectively redirecting light at a scattered wavelength, and/or the input wavelength. Note that the beam splitter may also redirect all or a portion of the returned light responsive to polarization or other characteristics of light.

Figure 3A:
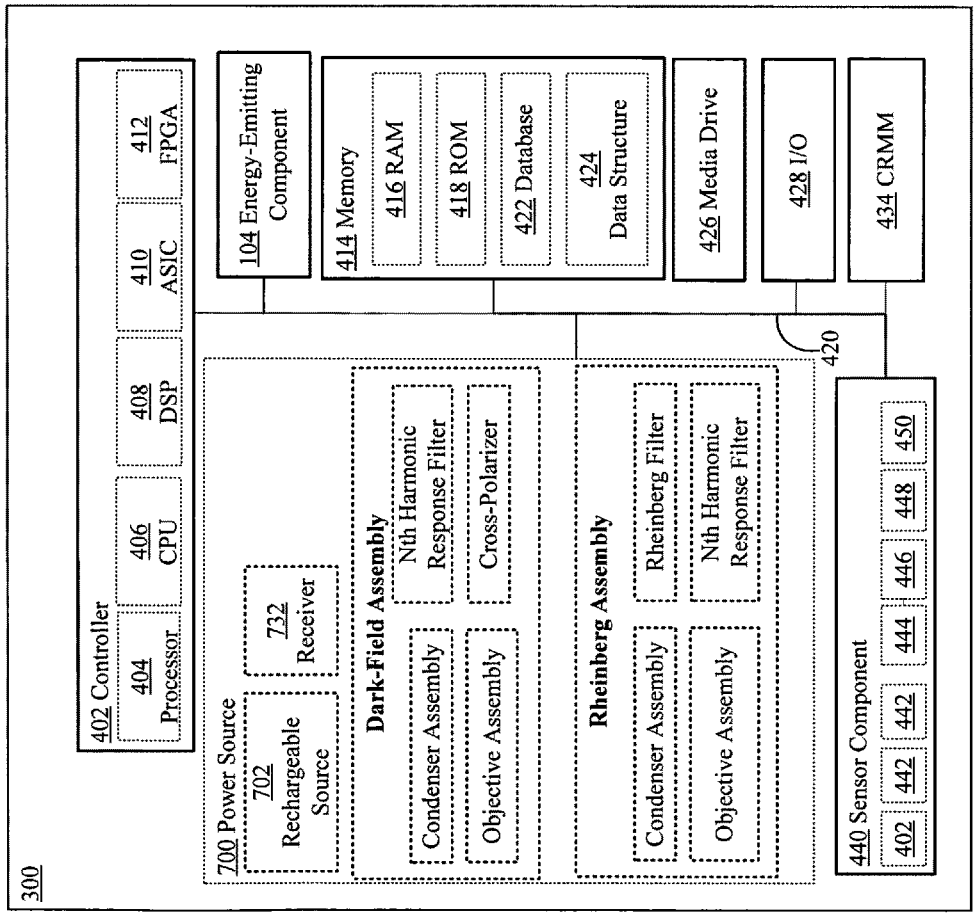
FIG. 3A is a perspective view of a hemozoin-monitoring device according to one illustrated embodiment.

FIG. 3A shows a hemozoin-monitoring device 300 in which one or more methodologies or technologies may be implemented. The hemozoin-monitoring device 300 includes, among other things, a sensor component 440 configured to detect a nonlinear multi-harmonic response profile associated with hemozoin nanoparticles in a biological tissue within multiple focal volumes interrogated by an electromagnetic energy stimulus (e.g., a pulsed electromagnetic energy stimulus, a spatially-patterned electromagnetic energy stimulus, a multiplexed electromagnetic energy stimulus, a spatially-patterned pulsed multiplexed electromagnetic energy stimulus, a temporally patterned electromagnetic energy stimulus, or the like). In an embodiment, the sensor component 440 is configured to detect a nonlinear multi-harmonic response profile using one or more differential illumination configurations (e.g., dark-field illumination, Rheinberg illumination, or the like). In an embodiment, the sensor component 440 is configured to detect a nonlinear multi-harmonic response profile using at least one of a dark-field detection configuration and a Rheinberg detection configuration. In an embodiment, the sensor component 440 is configured to detect a spectral signature characteristic for hemozoin optionally using at least one of a dark-field detection configuration and a Rheinberg detection configuration.

The hemozoin-monitoring device 300 can includes, among other things, one or more computer-readable storage media including executable instructions stored thereon that, when executed on a computer, instruct a controller to retrieving from storage one or more parameters associated with reference hemozoin nonlinear response information, and perform a comparison of a detected nonlinear multi-harmonic response profile to the retrieved one or more parameters. In an embodiment, the hemozoin-monitoring device 300 includes a transceiver configured to concurrently or sequentially transmit or receive information.

Figure 3B:
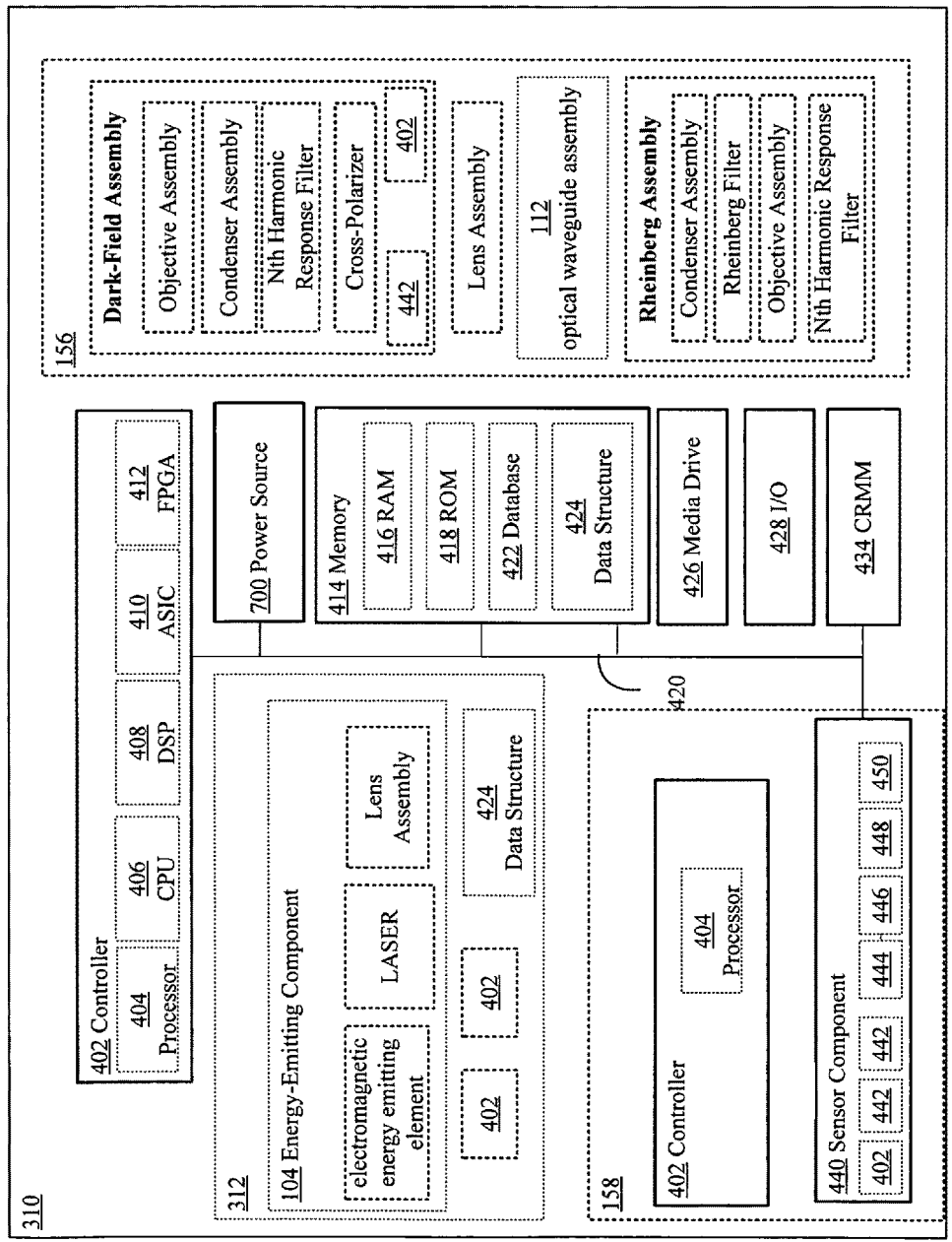
FIG. 3B is a perspective view of a medical diagnostic device according to one illustrated embodiment.

FIG. 3B shows a medical diagnostic device 310 in which one or more methodologies or technologies may be implemented. The medical diagnostic 310 includes, among other things, circuitry 312 configured to generate a multiplexed pulsed electromagnetic energy stimulus having a peak power ranging from about 400 gigawatts to about 8 terawatts. In an embodiment, the medical diagnostic device 310 includes circuitry 156 configured to direct the multiplexed pulsed electromagnetic energy stimulus on a plurality of focal volumes in a biological subject. In an embodiment, the medical diagnostic device 310 includes circuitry 158 configured to detect a multi-harmonic response associated with a plurality of hemozoin nanoparticles in a biological tissue within one or more of the plurality of focal volumes interrogated by the multiplexed pulsed electromagnetic energy stimulus.

Figure 3C:
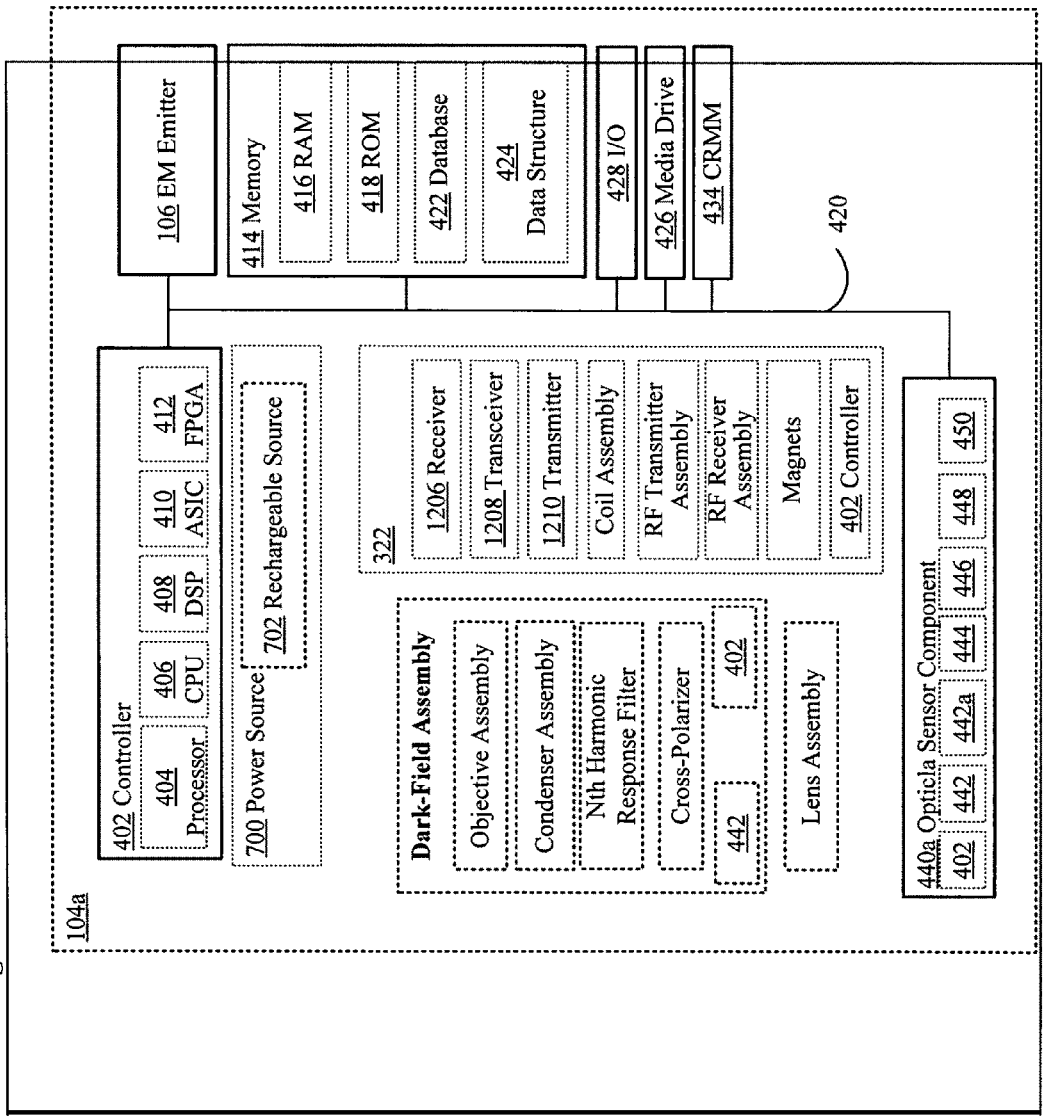
FIG. 3C is a perspective view of a medical diagnostic device according to one illustrated embodiment.

FIG. 3C shows a medical diagnostic device 320 which one or more methodologies or technologies may be implemented. The medical diagnostic device 320 includes, among other things, a dark-field electromagnetic energy emitting component 104a. In an embodiment, the dark-field electromagnetic energy emitting component 104a is configured to deliver a multi-mode dark-field interrogation stimulus to at least one blood vessel. The medical diagnostic device 320 can includes, among other things, a magnetic field component 322. In an embodiment, the magnetic field component 322 is configured to generate a magnetic field of a character and for a duration sufficient to magnetically align, in vivo, a plurality of hemozoin nanoparticles. The medical diagnostic device 320 includes, among other things, an optical energy sensor component 440a. In an embodiment, the optical energy sensor component 440a is configured to detect scatter optical energy from the plurality of hemozoin nanoparticles interrogated by the multi-mode dark-field interrogation stimulus in the presence of the magnetic field.

Figure 3D:
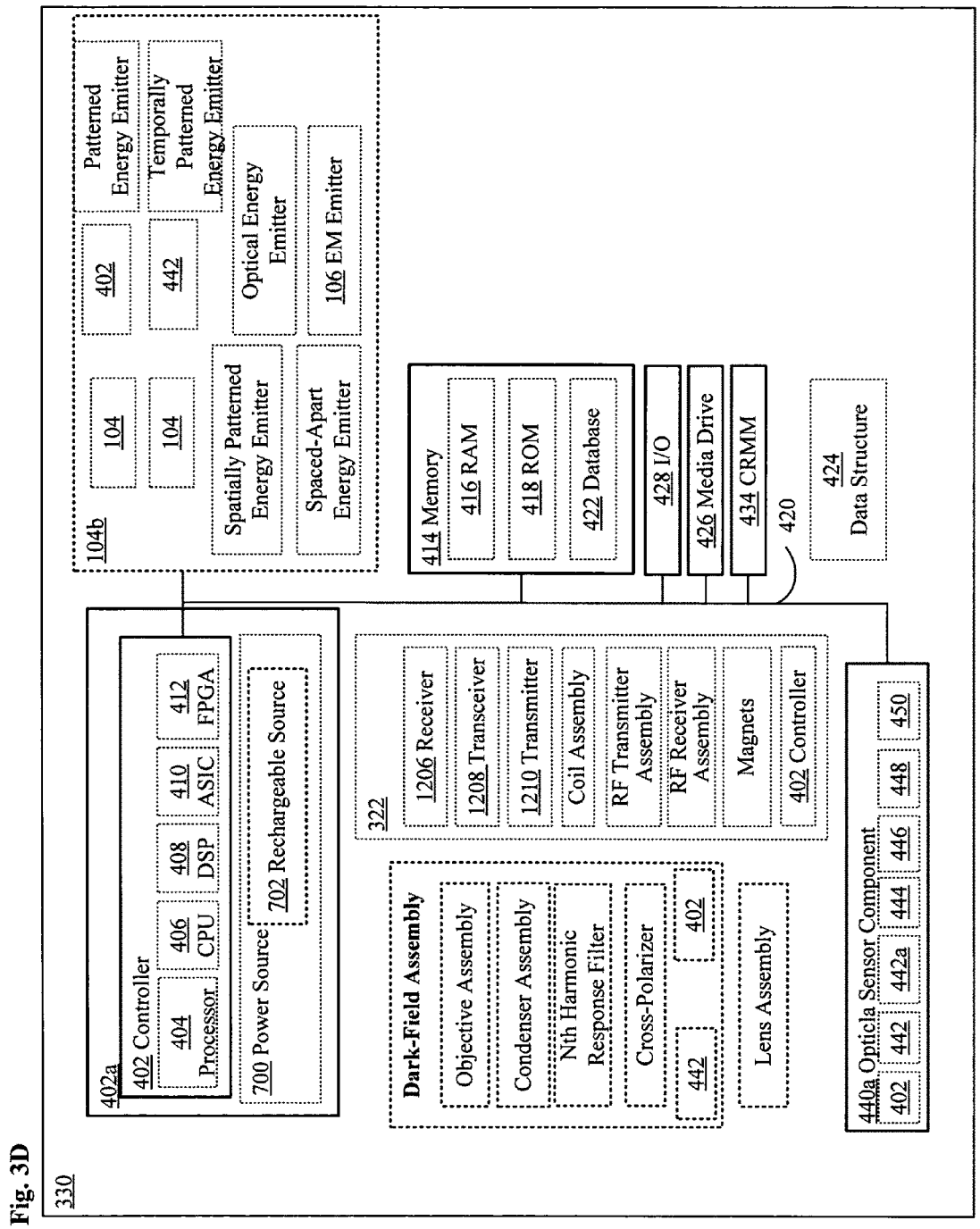
FIG. 3D is a perspective view of an in situ hemozoin-monitoring device according to one illustrated embodiment.

FIG. 3D shows an in situ hemozoin-monitoring device 330 in which one or more methodologies or technologies may be implemented. The in situ hemozoin-monitoring device 330 includes, among other things, an actively-controllable excitation component 104b configured to deliver a spatially-patterned pulsed electromagnetic energy stimulus to one or more focal volumes and configured to elicit a non-linear multi-harmonic response information from hemozoin nanoparticles in a biological tissue within the multiple focal volumes. In an embodiment, the in situ hemozoin-monitoring device 330 includes a control means 332 operably coupled to the actively-controllable excitation 104b component and configured to regulate at least one of a numerical aperture, a spaced-apart delivery pattern parameter, and a temporal delivery pattern parameter associated with the delivery of the spatially-patterned pulsed electromagnetic energy stimulus. In an embodiment, the actively-controllable excitation component 104b is configured to regulate at least one of parameter associated with a peak power, a peak irradiance, a focal spot size, and a pulse width.

Figure 3E:
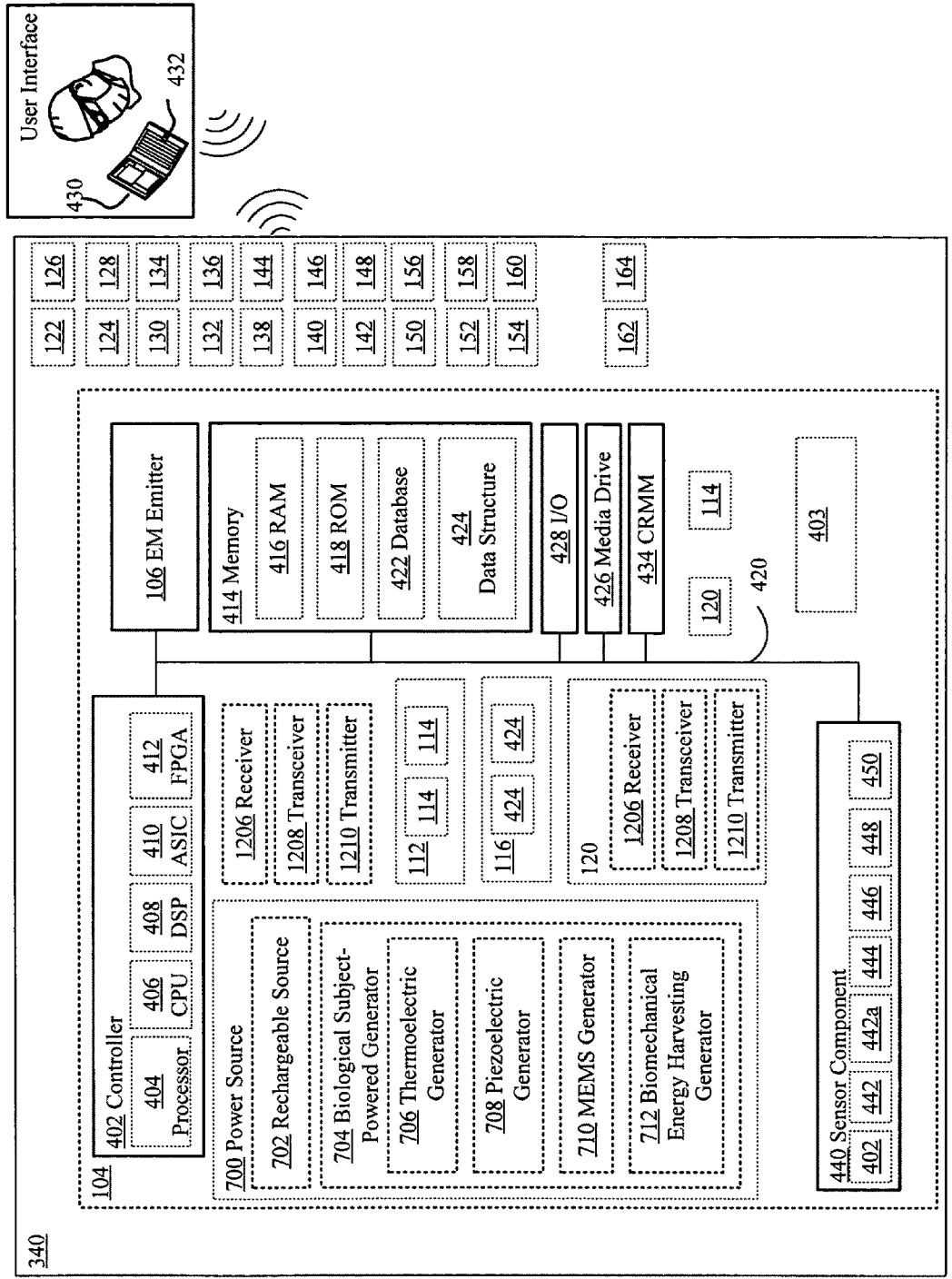
FIG. 3E is a perspective view of an anti-malarial therapeutic device according to one illustrated embodiment.

FIG. 3E shows an anti-malarial therapeutic device 340 in which one or more methodologies or technologies may be implemented. In an embodiment, the anti-malarial therapeutic device 340 includes, among other things, a sensor component 440 including at least one sensor configured to detect nonlinear multi-harmonic response energy associated with hemozoin nanoparticles within at least one focal volume of a biological tissue interrogated by an electromagnetic energy stimulus. In an embodiment, the anti-malarial therapeutic device 340 includes an energy-emitting component 104 configured to deliver an effective amount of a electromagnetic energy stimulus to elicit a nonlinear optical response from hemozoin nanoparticles within the biological tissue, the elicited nonlinear response of a character and for a duration sufficient to modulate a biological activity of a malarial infectious agent within the biological tissue. In an embodiment, the anti-malarial therapeutic device 340 includes a controller 402 operably coupled to at least one sensor of the sensor component 440 and the energy-emitting component 104, the controller 402 configured to provide a control signal to the energy-emitting component.

Figure 4A:
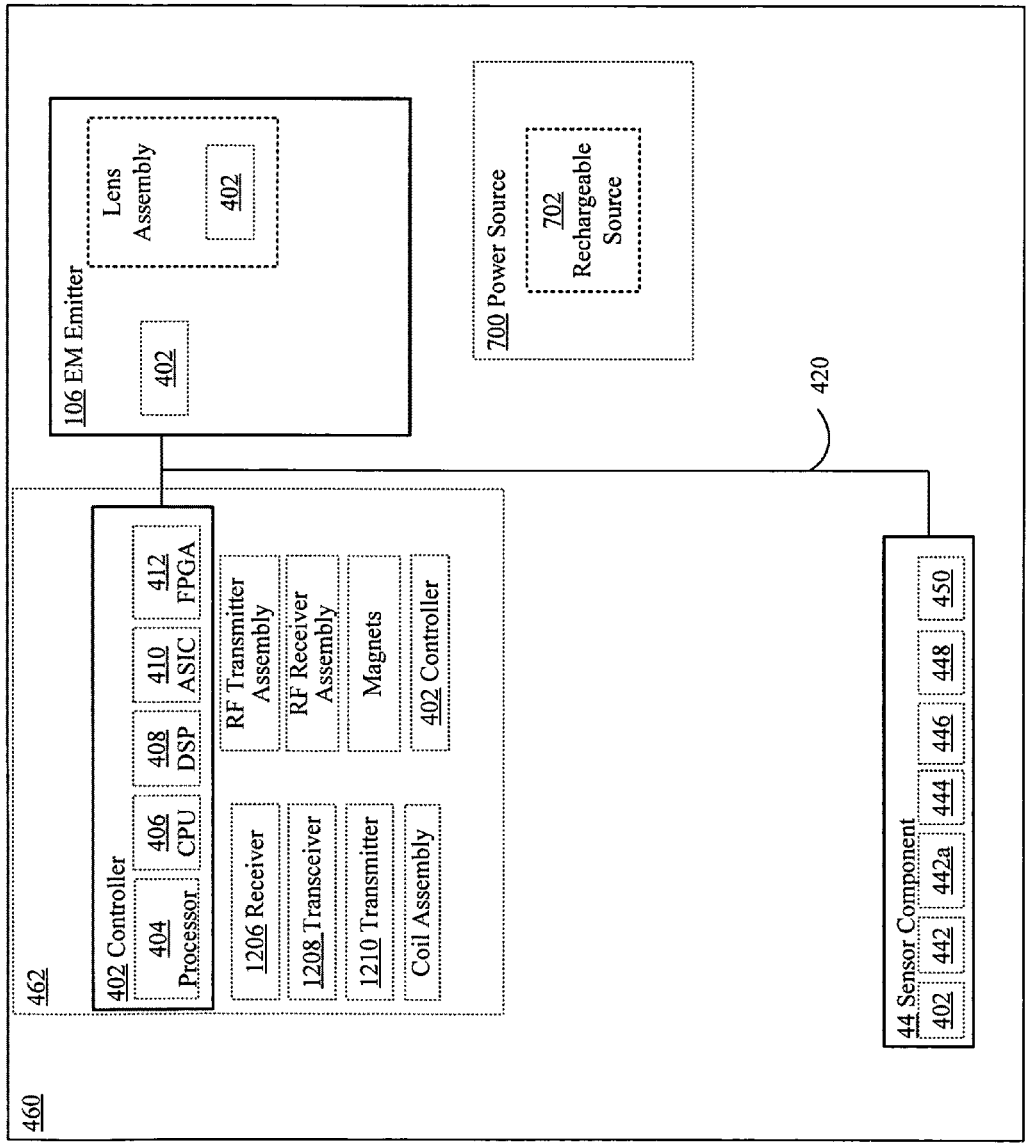
FIG. 4A is a perspective view of an apparatus according to one illustrated embodiment.

FIG. 4A shows an apparatus 460 in which one or more methodologies or technologies may be implemented. The apparatus 460 includes, among other things, an actively-controllable magnetic field generator 462 and a controller operatively coupled to the actively-controllable magnetic field generator 462. In an embodiment, the actively-controllable magnetic field generator 462 is configured to deliver a varying magnetic field stimulus at a dose sufficient to cause heat generation from hemozoin nanoparticles within a biological sample. In an embodiment, the controller 402 is operatively coupled to the actively-controllable magnetic field generator 462, and includes one or more processors 404 for controlling at least one of a magnetic field ON duration, a magnetic field strength, a magnetic field frequency, and a magnetic field waveform.

Figure 4B:
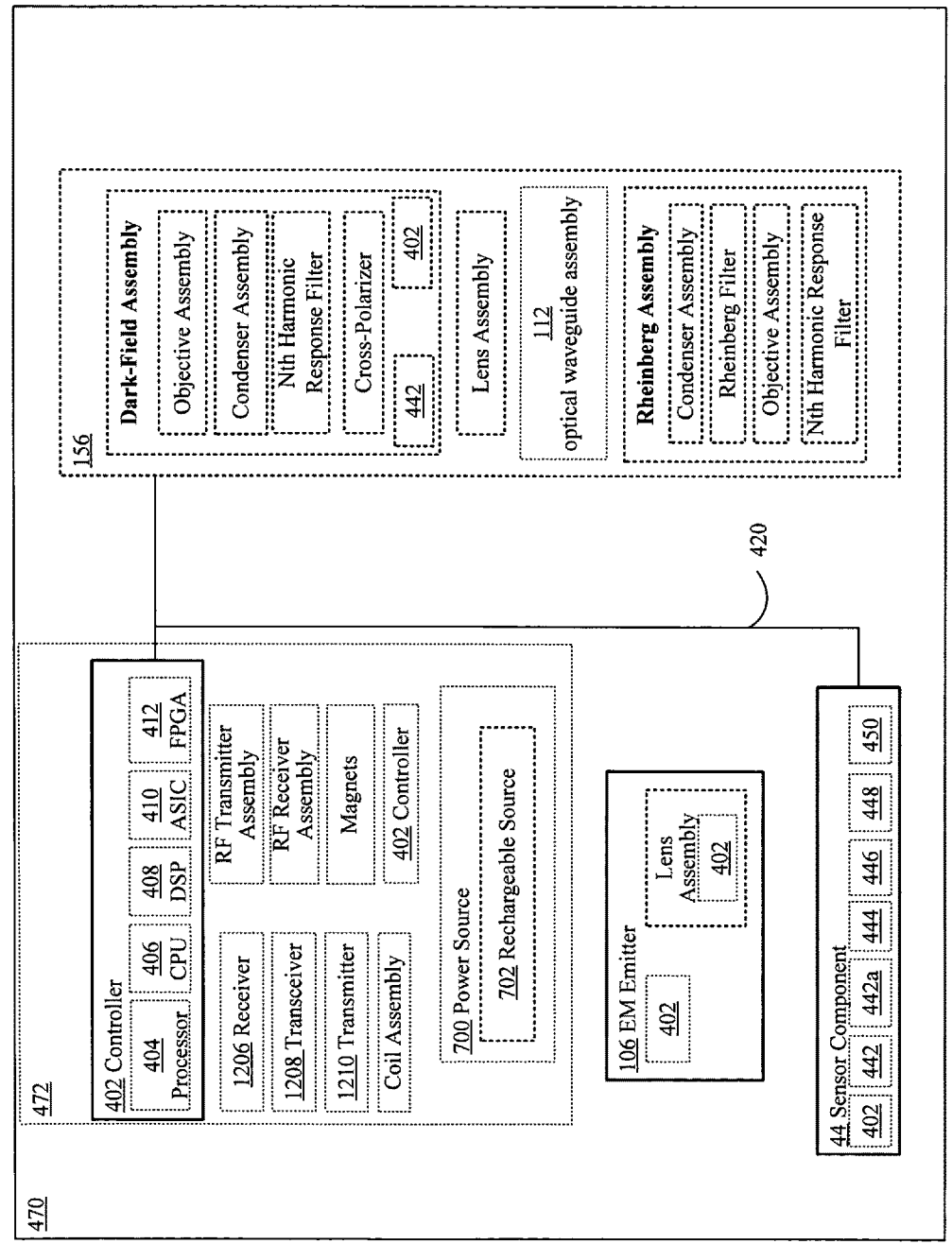
FIG. 4B is a perspective view of an apparatus according to one illustrated embodiment.

FIG. 4B shows an apparatus 470 in which one or more methodologies or technologies may be implemented. In an embodiment, the apparatus 460 includes a magnetic field generator 472 configured to concurrently or sequentially generate at least a first electromagnetic energy stimulus and a second electromagnetic energy stimulus, the first electromagnetic energy stimulus of a character and for a duration sufficient to magnetically align hemozoin nanoparticles in a biological tissue, the second electromagnetic energy stimulus of a character and for a duration sufficient to magnetically induce at least one of an oscillation, a translation, and a rotation of the hemozoin nanoparticles in the biological tissue.

Figure 5:
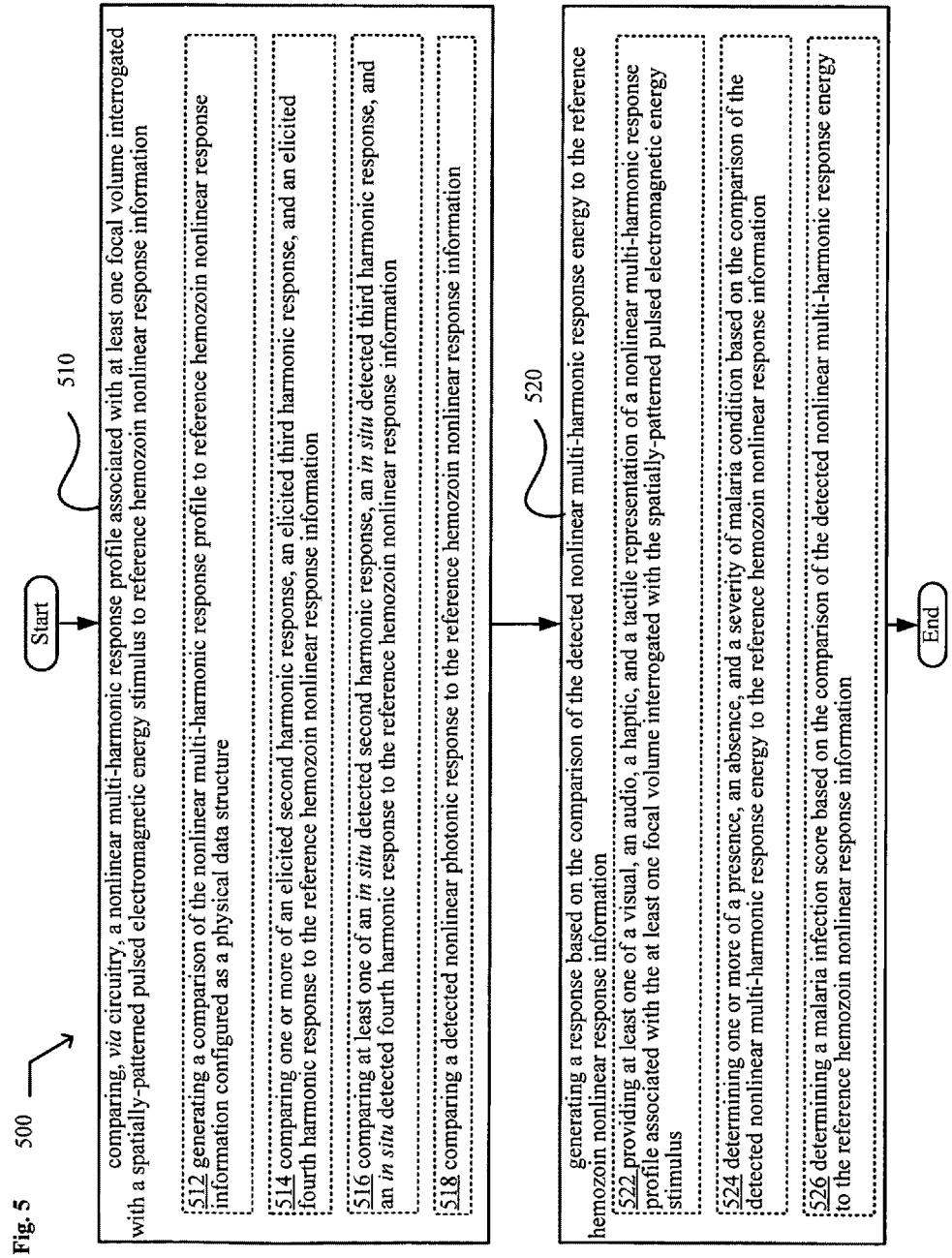
FIG. 5 is a flow diagram of a method according to one illustrated embodiment.

FIG. 5 shows an example of a method 500 for detecting a condition associated with plasmodium-infected erythrocytes. At 510, the method 500 includes comparing, via circuitry, a nonlinear multi-harmonic response profile associated with at least one focal volume interrogated with a spatially-patterned pulsed electromagnetic energy stimulus to reference hemozoin nonlinear response information. At 512, comparing, using circuitry, the nonlinear multi-harmonic response profile associated with the at least one focal volume interrogated with the spatially-patterned pulsed electromagnetic energy stimulus to the reference hemozoin nonlinear response information includes generating a comparison of the nonlinear multi-harmonic response profile to reference hemozoin nonlinear response information configured as a physical data structure. At 514, comparing, using circuitry, the nonlinear multi-harmonic response profile associated with the at least one focal volume interrogated with the spatially-patterned pulsed electromagnetic energy stimulus to the reference hemozoin nonlinear response information includes comparing one or more of an elicited second harmonic response, an elicited third harmonic response, and an elicited fourth harmonic response to the reference hemozoin nonlinear response information. At 516, comparing, using circuitry, the nonlinear multi-harmonic response profile associated with the at least one focal volume interrogated with the spatially-patterned pulsed electromagnetic energy stimulus to the reference hemozoin nonlinear response information includes comparing at least one of an in situ detected second harmonic response, an in situ detected third harmonic response, and an in situ detected fourth harmonic response to the reference hemozoin nonlinear response information. At 518, comparing, using circuitry, the nonlinear multi-harmonic response profile associated with the at least one focal volume interrogated with the spatially-patterned pulsed electromagnetic energy stimulus to the reference hemozoin nonlinear response information includes comparing a detected nonlinear photonic response to the reference hemozoin nonlinear response information.

At 520, the method 500 can further include generating a response based on the comparison of the detected nonlinear multi-harmonic response energy to the reference hemozoin nonlinear response information. At 522, generating the response includes providing at least one of a visual, an audio, a haptic, and a tactile representation of a nonlinear multi-harmonic response profile associated with the at least one focal volume interrogated with the spatially-patterned pulsed electromagnetic energy stimulus. At 524, generating the response includes determining one or more of a presence, an absence, and a severity of malaria condition based on the comparison of the detected nonlinear multi-harmonic response energy to the reference hemozoin nonlinear response information. At 526, generating the response includes determining a malaria infection score based on the comparison of the detected nonlinear multi-harmonic response energy to the reference hemozoin nonlinear response information.

Figure 6:
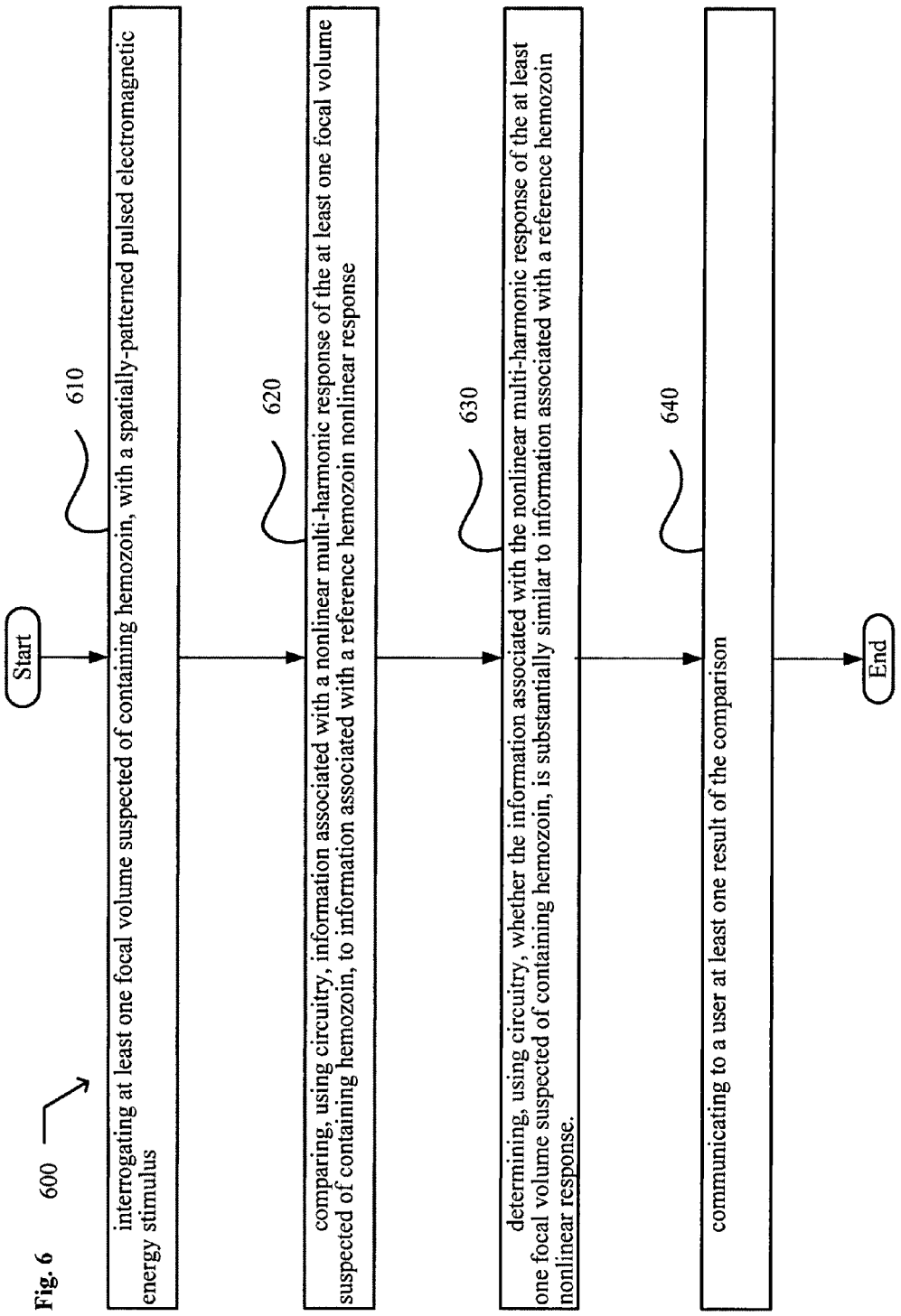
FIG. 6 is a flow diagram of a method according to one illustrated embodiment.

FIG. 6 shows an example of a method 600. At 610, the method 600 includes interrogating at least one focal volume suspected of containing hemozoin, with a spatially-patterned pulsed electromagnetic energy stimulus. At 620, the method 600 can further include comparing, using circuitry, information associated with a nonlinear multi-harmonic response of the at least one focal volume suspected of containing hemozoin, to information associated with a reference hemozoin nonlinear response. At 630, the method 600 can further include determining, using circuitry, whether the information associated with the nonlinear multi-harmonic response of the at least one focal volume suspected of containing hemozoin, is substantially similar to information associated with a reference hemozoin nonlinear response. At 640, the method 600 can further include communicating to a user at least one result of the comparison.

Figure 7:
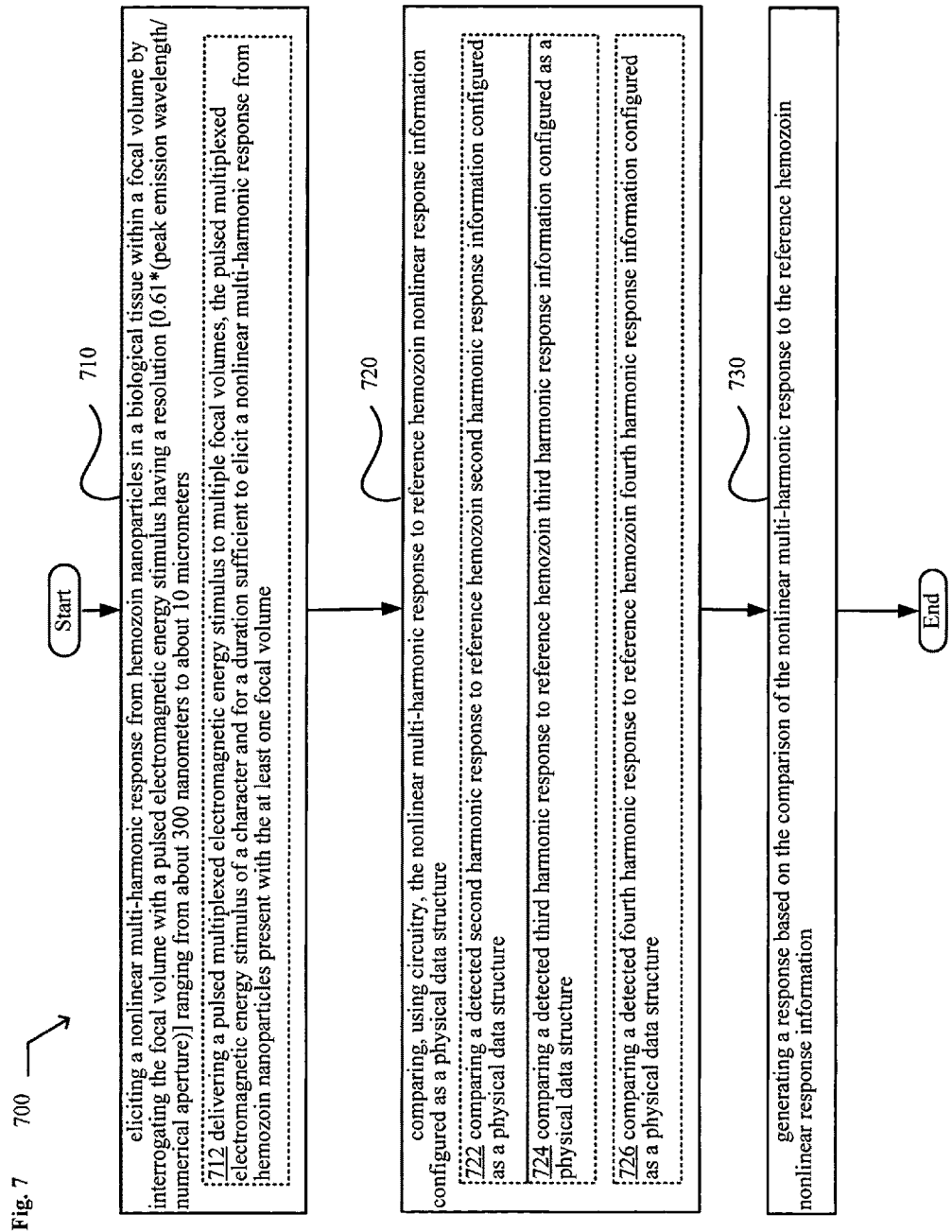
FIG. 7 is a flow diagram of a method according to one illustrated embodiment.

FIG. 7 shows an example of a method 700. At 710, the method 700 includes eliciting a nonlinear multi-harmonic response from hemozoin nanoparticles in a biological tissue within a focal volume by interrogating the focal volume with a pulsed electromagnetic energy stimulus having a resolution [0.61*(peak emission wavelength/numerical aperture)] ranging from about 300 nanometers to about 10 micrometers. At 712, eliciting the nonlinear multi-harmonic response includes delivering a pulsed multiplexed electromagnetic energy stimulus to multiple focal volumes, the pulsed multiplexed electromagnetic energy stimulus of a character and for a duration sufficient to elicit a nonlinear multi-harmonic response from hemozoin nanoparticles present with the at least one focal volume. At 720, the method 700 can further include comparing, using circuitry, the nonlinear multi-harmonic response to reference hemozoin nonlinear response information configured as a physical data structure. At 722, comparing, using circuitry, the nonlinear multi-harmonic response to the reference hemozoin nonlinear response information includes comparing a detected second harmonic response to reference hemozoin second harmonic response information configured as a physical data structure. At 724, comparing, using circuitry, the nonlinear multi-harmonic response to the reference hemozoin nonlinear response information includes comparing a detected third harmonic response to reference hemozoin third harmonic response information configured as a physical data structure. At 726, comparing, using circuitry, the nonlinear multi-harmonic response to the reference hemozoin nonlinear response information includes comparing a detected fourth harmonic response to reference hemozoin fourth harmonic response information configured as a physical data structure.

At 730, the method 700 can further include generating a response based on the comparison of the nonlinear multi-harmonic response to the reference hemozoin nonlinear response information.

FIG. 8 shows an example of a method 800. At 810, the method 800 includes comparing, using circuitry, information associated with a nonlinear multi-harmonic response of at least one focal volume suspected of containing hemozoin, the at least one focal volume interrogated with a spatially-patterned pulsed electromagnetic energy stimulus, to information associated with a reference hemozoin nonlinear multi-harmonic response.

FIG. 9 shows an example of an in situ method 900. At 910, the method 900 includes detecting, via one or more sensors, non-linear multi-harmonic response information associated with multiple focal volumes interrogated with a spatially-patterned pulsed electromagnetic energy stimulus. At 920, the method 900 can includes determining whether the detected non-linear multi-harmonic response information associated with the multiple focal volumes interrogated with the spatially-patterned pulsed electromagnetic energy stimulus satisfies threshold criteria associated with an absence, presence, or severity of hemozoin nanoparticles in a biological tissue. At 930, the method 900 can further includes generating a response in response to determining whether the detected non-linear multi-harmonic response information associated with the multiple focal volumes interrogated with the spatially-patterned pulsed electromagnetic energy stimulus satisfies threshold criteria associated with the presence of hemozoin nanoparticles in a biological tissue.

Figure 10:
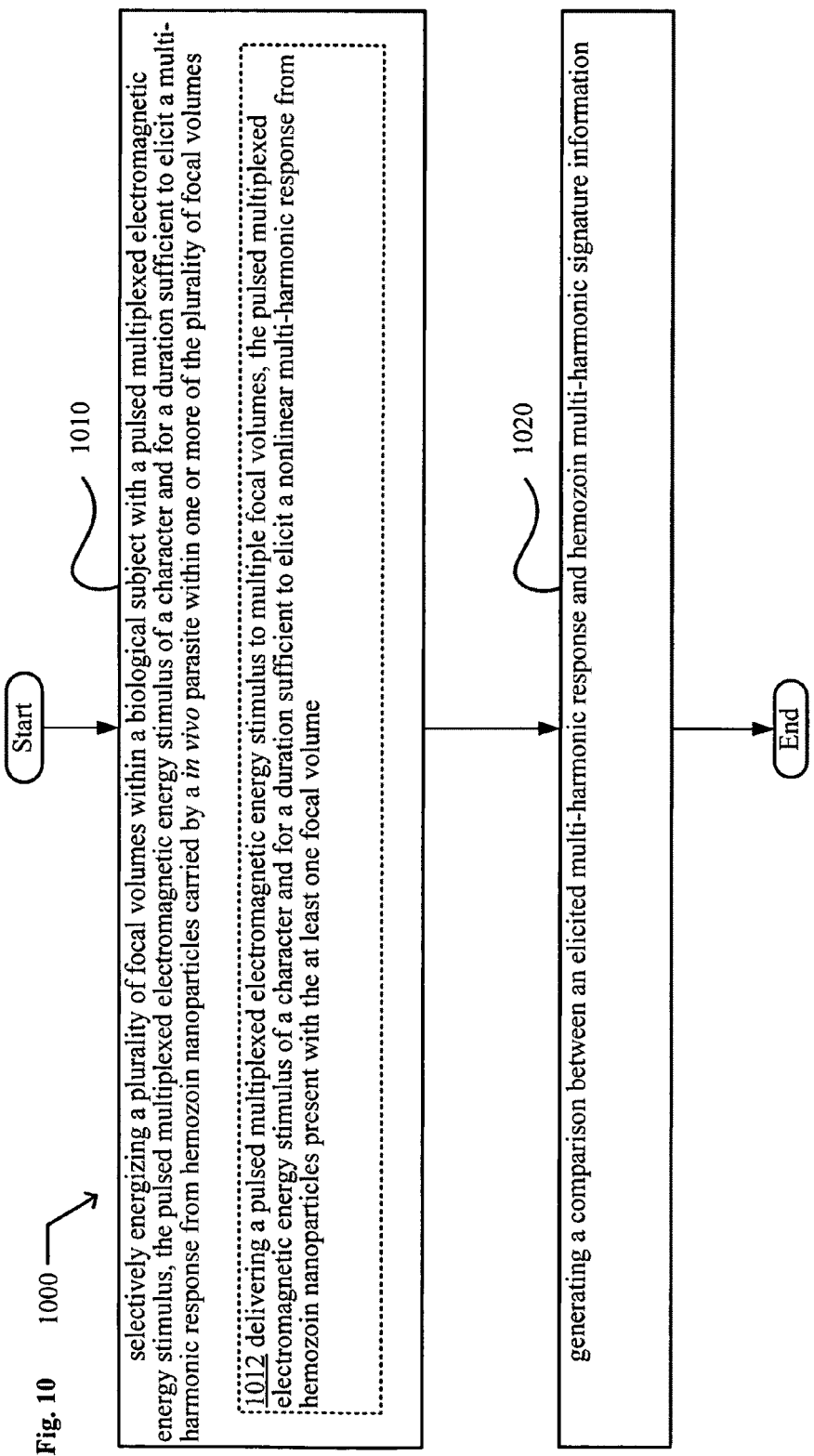
FIG. 10 is a flow diagram of a method according to one illustrated embodiment.

FIG. 10 shows an example of a method 1000. At 1010, the method 1000 includes selectively energizing a plurality of focal volumes within a biological subject with a pulsed multiplexed electromagnetic energy stimulus, the pulsed multiplexed electromagnetic energy stimulus of a character and for a duration sufficient to elicit a multi-harmonic response from hemozoin nanoparticles carried by a parasite within one or more of the plurality of focal volumes. At 1012, selectively energizing the plurality of focal volume includes delivering a pulsed electromagnetic energy stimulus of a character and for a duration sufficient to elicit one or more of a second harmonic response, a third harmonic response, and a fourth harmonic response from hemozoin nanoparticles carried by a parasite. At 1020, the method 1000 includes generating a comparison between an elicited multi-harmonic response and hemozoin multi-harmonic signature information.

FIG. 11 shows an example of a method 1100. At 1110, the method 1100 includes concurrently generating a multi-mode dark-field interrogation stimulus and a magnetic field stimulus. At 1120, the method 1100 includes detecting a scattering response associated with a plurality of hemozoin nanoparticles interrogated by the multiplexed dark-field interrogation stimulus in the presence of the magnetic field. At 1130, the method 1100 can further include varying a direction of the magnetic field stimulus. At 1140, the method 1100 can further include detecting scattering response associated with the plurality of hemozoin nanoparticles interrogated by the multiplexed dark-field interrogation stimulus in the presence of the varying magnetic field. At 1150, the method 1100 can further include varying a strength of the magnetic field stimulus.

At 1160, the method 1100 can further include detecting a scattering response associated with the plurality of hemozoin nanoparticles interrogated by the multiplexed dark-field interrogation stimulus in the presence of the varying magnetic field. At 1162, detecting the scattering response includes detecting a polarization of emerging scattering information. At 1164, detecting the scattering response includes detecting at least one of a diffracted, a reflected, and a refracted light associated with the plurality of hemozoin nanoparticles interrogated by the multiplexed dark-field interrogation stimulus in the presence of the magnetic field.

FIG. 12 shows an example of a method 1200. At 1210, the method 1200 includes concurrently generating a multi-mode dark-field interrogation stimulus of a character and for a duration sufficient to elicit a dark-field scattering response from hemozoin nanoparticles in a biological tissue and a magnetic field stimulus of a character and for a duration sufficient to magnetically align hemozoin nanoparticles in a biological tissue.

At 1220, the method 1200 includes detecting scattered electromagnetic radiation associated with a plurality of target regions within a biological subject interrogated by the multiplexed dark-field interrogation stimulus in the presence of the magnetic field stimulus.

FIG. 13 shows an example of a method 1300 of heat-shocking a plasmodium parasite. At 1310, the method 1300 includes delivering a time varying magnetic field energy to the biological subject, the time varying magnetic field energy sufficient to cause hemozoin nanoparticles in the plasmodium parasite to generate thermal energy.

FIG. 14 shows an example of a method 1400 of treating a biological subject suspected of being infected with a plasmodium parasite. At 1410, the method 1400 includes delivering targeted magnetic heating within a biological subject suspected of having a plasmodium parasite by sufficiently varying an applied magnetic field so as to cause hemozoin nanoparticles within a plasmodium parasite to generate thermal energy. At 1412, delivering the targeted magnetic heating includes providing an alternating external magnetic field stimulus via one or more magnetic energy-emitting components to one or more regions of a biological subject suspected of having a malaria infection, the alternating external magnetic field stimulus of a character and for a duration sufficient to cause heat-induced programmed cell death of plasmodium parasites. At 1414, delivering the targeted magnetic heating includes delivering a time-varying external magnetic field to one or more regions of the biological subject suspected of having hemozoin. At 1416, delivering the targeted magnetic heating includes delivering a time-varying spatially focused external magnetic field to one or more regions of the biological subject suspected of having hemozoin. At 1418, delivering the targeted magnetic heating includes delivering an effective dose of a pulsed magnetic field stimulus to cause one or more of Brown relaxation and Neél relaxation of hemozoin nanoparticles in a biological tissue, the effective dose sufficient to increase the temperature in a region within the plasmodium parasite by about 3° C. to about 22° C. At 1420, delivering the targeted magnetic heating includes delivering an effective dose of a pulsed magnetic field stimulus to induce one or more of Brown relaxation and Neél relaxation of hemozoin nanoparticles in a biological tissue, the effective dose sufficient to increase the temperature in a region within the plasmodium parasite by about 3° C. to about 10° C. At 1422, delivering the targeted magnetic heating includes delivering an effective dose of the pulsed magnetic stimulus to induce one or more of Brown relaxation and Neél relaxation of hemozoin nanoparticles in a biological tissue, the effective dose sufficient to increase the temperature in a region within the plasmodium parasite by about 3° C. to about 4° C. At 1424, delivering the targeted magnetic heating includes delivering a focused magnetic energy stimulus via a radio frequency transmitter to the biological subject suspected of having hemozoin. At 1426, delivering the targeted magnetic heating includes varying at least one of a duty cycle, a magnetic field strength, a magnetic field frequency, and a magnetic field waveform associated with the applied external magnetic field.

FIG. 15 shows an example of a method 1500 of enhancing a Brownian or Neelian process of a hemozoin nanoparticle. At 1510, the method 1500 includes comparing, using circuitry, (a) a nonlinear multi-harmonic response profile information associated with at least one focal volume interrogated with a spatially patterned pulsed electromagnetic energy stimulus to (b) a reference hemozoin nonlinear response information. At 1520, the method 1500 includes applying a varying magnetic field to the at least one focal volume, the varying magnetic field energy sufficient to cause hemozoin nanoparticles to at least one of oscillate, a translate, and a rotate.

FIG. 16 shows an example of a method 1600 of method of treating a plasmodium parasitic infection. At 1610, the method 1600 includes comparing, using circuitry, (a) a nonlinear multi-harmonic response profile information associated with at least one focal volume interrogated with a spatially patterned pulsed electromagnetic energy stimulus to (b) a reference hemozoin nonlinear response information. At 1620, the method 1600 includes magnetically inducing at least one of an oscillation, a translation, and a rotation of hemozoin nanoparticles in the at least one focal volume. At 1622, magnetically inducing the at least one of the oscillation, the translation, and the rotation of hemozoin nanoparticles in the at least one focal volume includes energizing one or more conductive coils for a duration sufficient to generate a time-varying magnetic field of a character and for a duration sufficient to cause hemozoin nanoparticles to at least one of oscillate, translate, and rotate. At 1624, magnetically inducing the at least one of the oscillation, the translation, and the rotation of hemozoin nanoparticles in the at least one focal volume includes delivering an effective dose of a pulsed magnetic field stimulus to affect the integrity of an organelle of a malarial infectious agent based in part on the comparison of the nonlinear multi-harmonic response profile associated with the at least one focal volume to the reference hemozoin nonlinear response information. At 1626, magnetically inducing the at least one of the oscillation, the translation, and the rotation of hemozoin nanoparticles in a biological tissue includes providing a radio frequency coil assembly an effective amount of an applied current, the effective amount of an applied current of a character and for a duration sufficient to generate a magnetic field of a character and for a duration sufficient to cause one or more of oscillation, translation, and rotation of hemozoin nanoparticles in a biological tissue. At 1628, magnetically inducing the at least one of the oscillation, the translation, and the rotation of hemozoin nanoparticles in a biological tissue includes delivering an effective dose of a pulsed magnetic field stimulus to cause one or more of oscillation, translation, and rotation of hemozoin nanoparticles in a biological tissue. At 1630, magnetically inducing the at least one of the oscillation, the translation, and the rotation of hemozoin nanoparticles in a biological tissue includes delivering an effective dose of an electromagnetic energy stimulus to cause one or more of oscillation, translation, and rotation of hemozoin nanoparticles in a biological tissue.

FIG. 17 shows an example of a method 1700. At 1710, the method 1700 includes At 1710, the method 1700 includes generating a comparison between (a) a detected scattering profile information associated with a plurality of target regions within a biological tissue interrogated by a dark-field interrogation stimulus in the presence of a magnetic field stimulus and (b) reference hemozoin dark field scattering information. At 1712, generating the comparison includes comparing, using circuitry, a detected scattering profile associated with a plurality of target regions within a biological subject interrogated by a multiplexed dark-field interrogation stimulus in the presence of a magnetic field stimulus and reference hemozoin dark field scattering information. At 1714, generating the comparison includes comparing, using circuitry, a detected scattering profile obtained using a Rheinberg illumination configuration in the presence of a magnetic field stimulus and reference hemozoin Rheinberg illumination spectral information.

At 1720, the method 1700 includes magnetically perturbing hemozoin nanoparticles in the biological tissue based in part on the comparison. At 1722, magnetically perturbing the hemozoin nanoparticles in a biological tissue includes applying a magnetic field stimulus of a character and for a duration sufficient to cause the hemozoin nanoparticles in a biological tissue to affect the integrity of a digestive food vacuole of a malaria parasite. At 1724, magnetically perturbing the hemozoin nanoparticles in a biological tissue includes applying an alternating magnetic field stimulus of a character and for a duration sufficient to cause the hemozoin nanoparticles in a biological tissue to rupture a membrane of a digestive food vacuole of a malaria parasite. At 1726, magnetically perturbing the hemozoin nanoparticles in a biological tissue includes applying a time-varying magnetic field stimulus of a character and for a duration sufficient to cause a reduction in a parasitemia level.

Figure 18A:
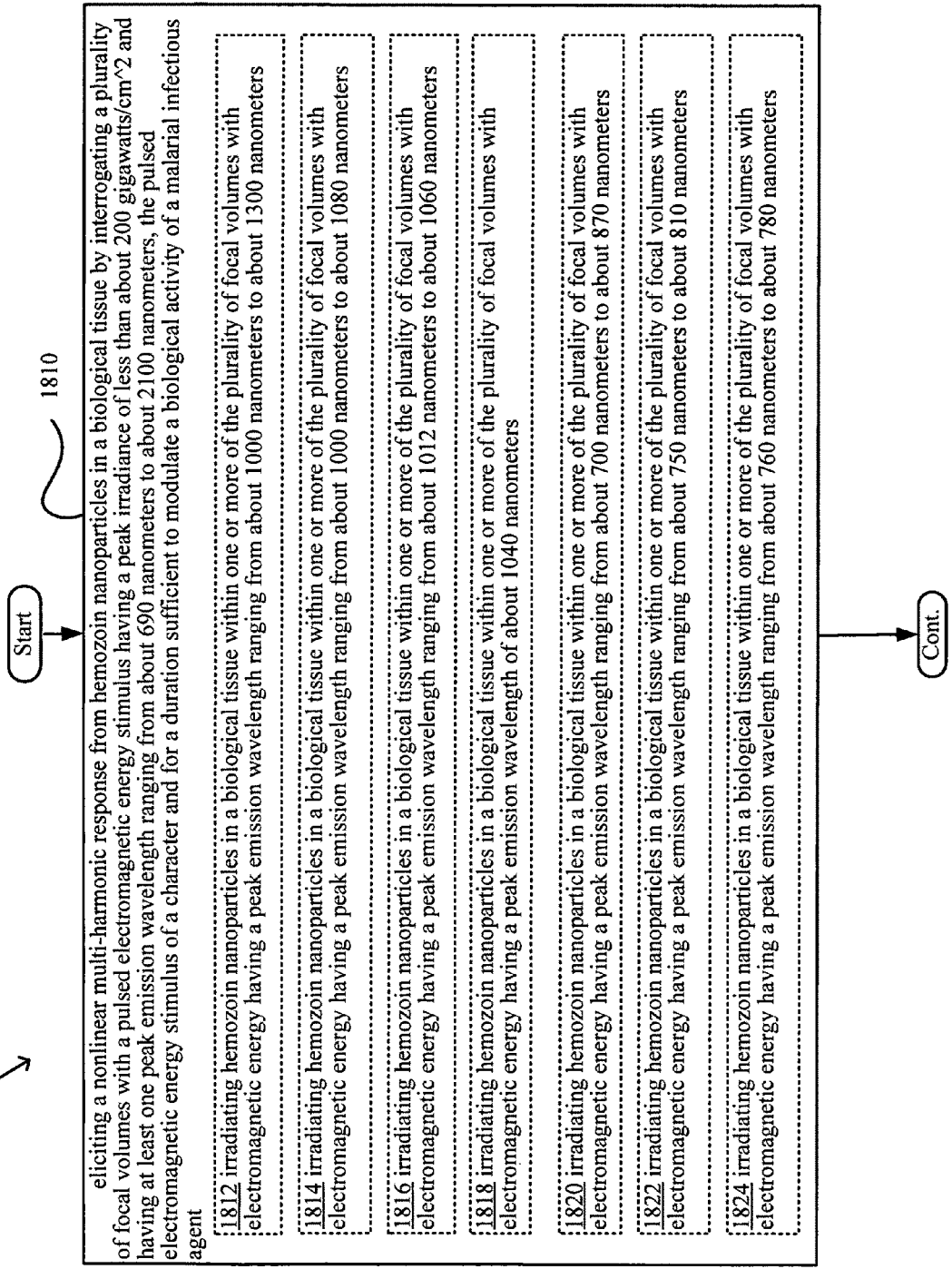
FIGS. 18A and 18B show a flow diagram of a method according to one illustrated embodiment.
Figure 18B:
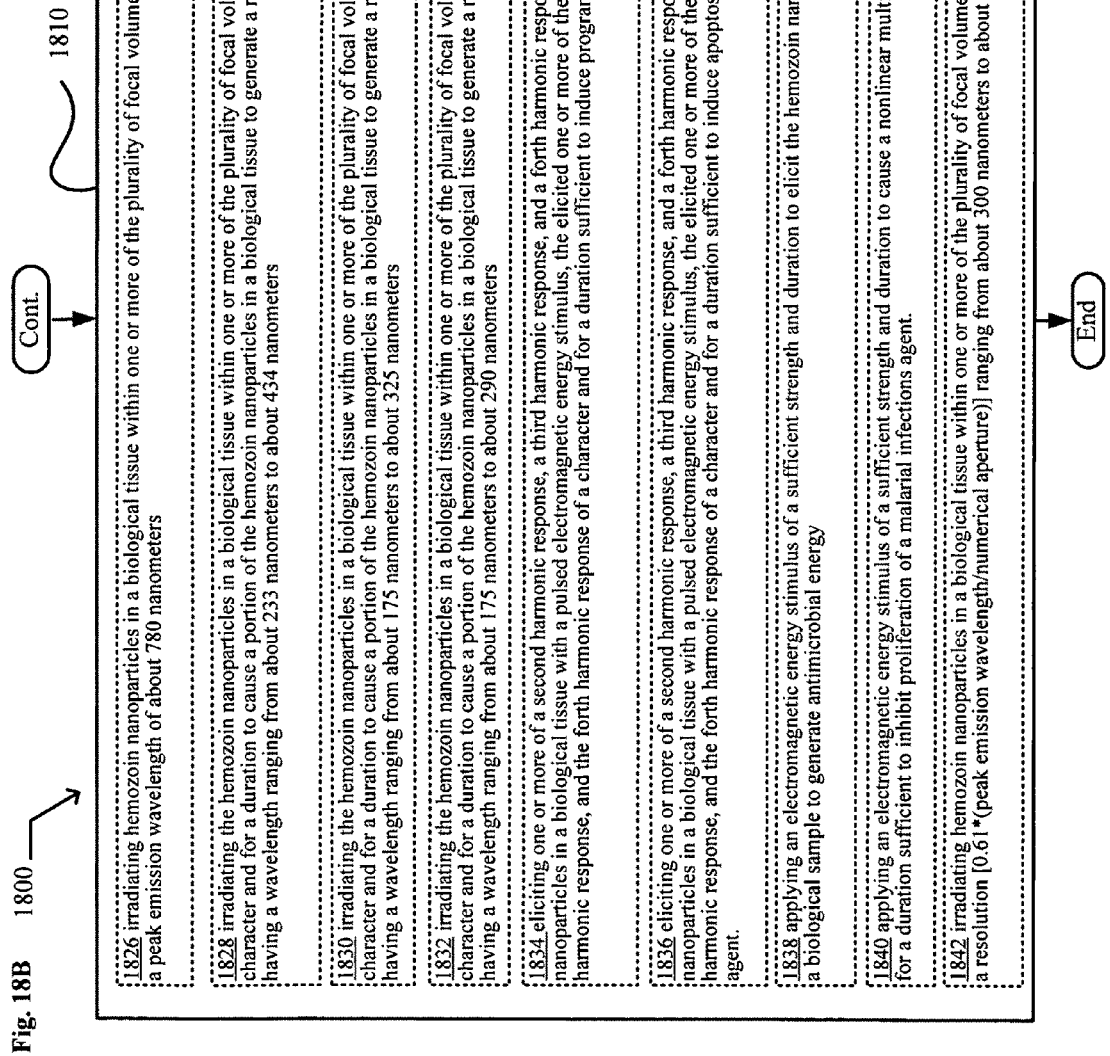

FIG. 18 shows an example of a method 1800 for modulating plasmodium parasitic activity. At 1810, the method 1800 includes eliciting a nonlinear multi-harmonic response from hemozoin nanoparticles in a biological tissue by interrogating a plurality of focal volumes with a pulsed electromagnetic energy stimulus having a peak irradiance of less than about 200 gigawatts/cm^2 and having at least one peak emission wavelength ranging from about 690 nanometers to about 2100 nanometers, the pulsed electromagnetic energy stimulus of a character and for a duration sufficient to modulate a biological activity of a malarial infectious agent. At 1812, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 1000 nanometers to about 1300 nanometers. At 1814, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 1000 nanometers to about 1080 nanometers. At 1816, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 1012 nanometers to about 1060 nanometers. At 1818, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength of about 1040 nanometers. At 1820, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 700 nanometers to about 870 nanometers. At 1822, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 750 nanometers to about 810 nanometers. At 1824, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength ranging from about 760 nanometers to about 780 nanometers. At 1826, eliciting the nonlinear multi-harmonic response from hemozoin nanoparticles in a biological tissue includes irradiating hemozoin nanoparticles in a biological tissue within one or more of the plurality of focal volumes with electromagnetic energy having a peak emission wavelength of about 780 nanometers. At 1828, eliciting the nonlinear multi-harmonic response from hemozoin nanoparticles in a biological tissue includes irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 233 nanometers to about 434 nanometers. At 1830, eliciting the nonlinear multi-harmonic response from hemozoin nanoparticles in a biological tissue includes irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 175 nanometers to about 325 nanometers.

At 1832, eliciting the nonlinear multi-harmonic response from hemozoin nanoparticles in a biological tissue includes irradiating the hemozoin nanoparticles in a biological tissue within one or more of the plurality of focal volumes with electromagnetic energy of a character and for a duration to cause a portion of the hemozoin nanoparticles in a biological tissue to generate a nonlinear multi-harmonic response having a wavelength ranging from about 175 nanometers to about 290 nanometers. At 1834, eliciting the nonlinear multi-harmonic response from hemozoin nanoparticles in a biological tissue includes eliciting one or more of a second harmonic response, a third harmonic response, and a forth harmonic response by interrogating the hemozoin nanoparticles in a biological tissue with a pulsed electromagnetic energy stimulus, the elicited one or more of the second harmonic response, the third harmonic response, and the forth harmonic response of a character and for a duration sufficient to induce programmed cell death of an infectious agent. At 1836, eliciting the nonlinear multi-harmonic response from hemozoin nanoparticles in a biological tissue includes eliciting one or more of a second harmonic response, a third harmonic response, and a forth harmonic response by interrogating the hemozoin nanoparticles in a biological tissue with a pulsed electromagnetic energy stimulus, the elicited one or more of the second harmonic response, the third harmonic response, and the forth harmonic response of a character and for a duration sufficient to induce apoptosis of a host cell carrying an infectious agent. At 1838, eliciting the nonlinear multi-harmonic response from hemozoin nanoparticles in a biological tissue includes applying an electromagnetic energy stimulus of a sufficient strength and duration to elicit the hemozoin nanoparticles in a biological tissue within a biological sample to generate antimicrobial energy. At 1840, eliciting the nonlinear multi-harmonic response from hemozoin nanoparticles in a biological tissue includes applying an electromagnetic energy stimulus of a sufficient strength and duration to cause a nonlinear multi-harmonic response of a character and for a duration sufficient to inhibit proliferation of a malarial infectious agent. At 1842, eliciting the nonlinear multi-harmonic response from hemozoin nanoparticles in a biological tissue includes irradiating hemozoin nanoparticles in a biological tissue within one or more of the plurality of focal volumes with electromagnetic energy having a resolution [0.61*(peak emission wavelength/numerical aperture)] ranging from about 300 nanometers to about 10 micrometers.

Figure 19:
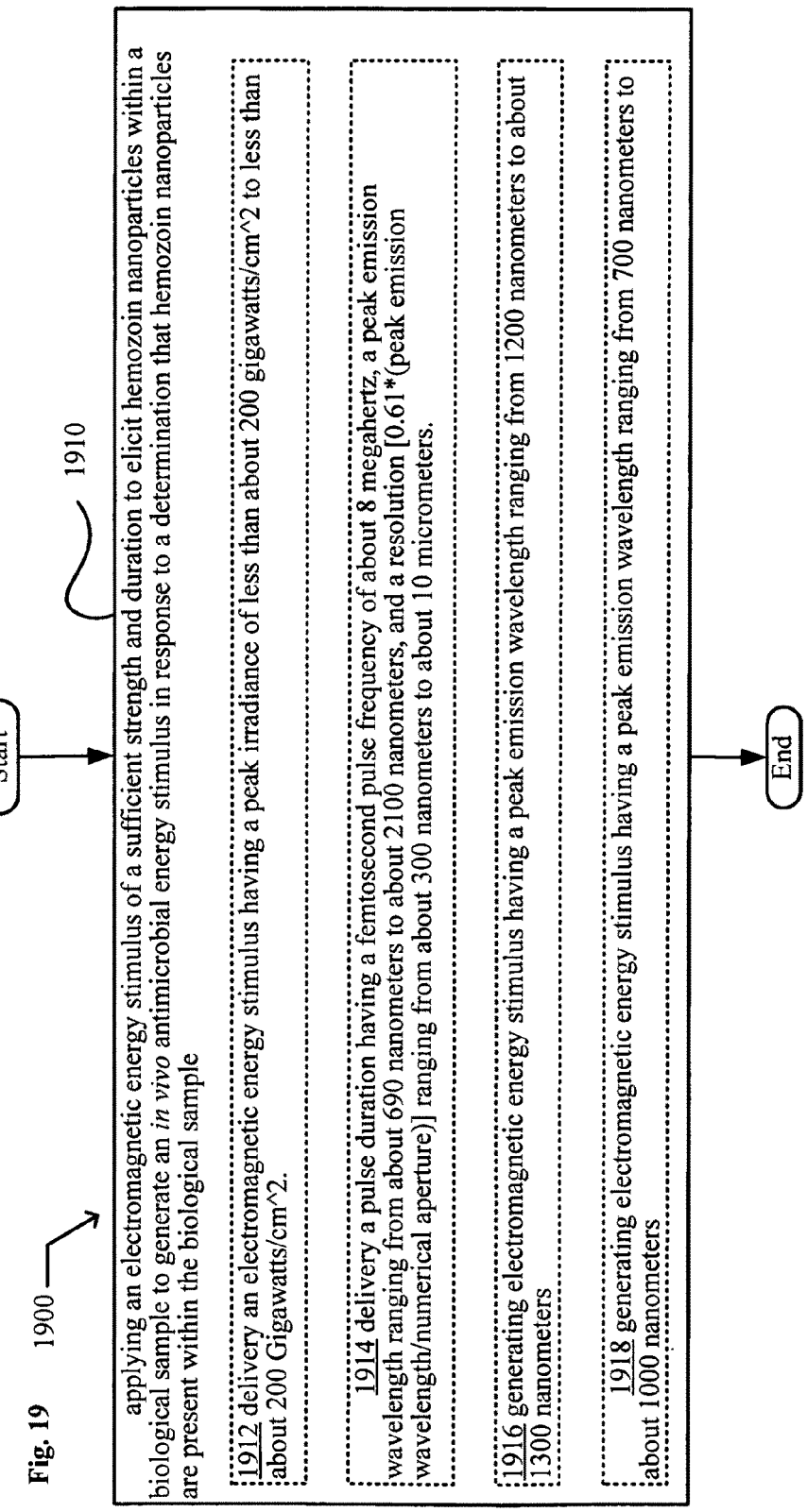
FIG. 19 is a flow diagram of a method according to one illustrated embodiment.

FIG. 19 shows an example of an anti-malarial therapeutic method 1900. At 1910, the method 1900 includes applying an electromagnetic energy stimulus of a sufficient strength and duration to elicit hemozoin nanoparticles within a biological sample to generate an in vivo antimicrobial energy stimulus in response to a determination that hemozoin nanoparticles are present within the biological sample. At 1912, applying the electromagnetic energy stimulus includes delivery an electromagnetic energy stimulus having a peak irradiance of less than about 200 gigawatts/cm^2 to less than about 200 Gigawatts/cm^2. At 1914, applying the electromagnetic energy stimulus includes delivery a pulse duration having a femtosecond pulse frequency of about 8 megahertz, a peak emission wavelength ranging from about 690 nanometers to about 2100 nanometers, and a resolution [0.61*(peak emission wavelength/numerical aperture)] ranging from about 300 nanometers to about 10 micrometers. At 1916, applying the electromagnetic energy stimulus includes generating electromagnetic energy stimulus having a peak emission wavelength ranging from 1200 nanometers to about 1300 nanometers. At 1918, applying the electromagnetic energy stimulus includes generating electromagnetic energy stimulus having a peak emission wavelength ranging from 700 nanometers to about 1000 nanometers.

At least a portion of the devices and/or processes described herein can be integrated into a data processing system. A data processing system generally includes one or more of a system unit housing, a video display device, memory such as volatile or non-volatile memory, processors 404 such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system may be implemented utilizing suitable commercially available components, such as those typically found in data computing/communication and/or network computing/communication systems.

As shown in Example 1, nonlinear optical response information, spectral information, and the like associated with for example, hemozoin nanoparticles can be determined by one or more in vivo or in vitro technologies or methodologies.

Example 1

In Vitro Analysis of Hemozoin Nanoparticles

A method is described for detecting nonlinear multi-harmonic response energy properties of materials having hemozoin nanoparticles. For this analysis, synthetic hemozoin crystals were crushed into a fine powder and suspended with isopropanol in a volume ratio of five parts isopropanol to one part hemozoin crystals. A droplet of the hemozoin/isopropanol suspension was placed onto a quartz coverslip (0.25 mm thickness) and the isopropanol allowed to evaporate to generate a thin-film of hemozoin. The hemozoin thin-film was further heated at 70° C. for one minute to eliminate any residual condensation. The integrity and distribution of hemozoin crystals in the hemozoin thin-film were assessed at a magnification ranging from 20× to 100×. Crystals observed in the hemozoin thin-film ranged in size from under 1 micron to about 10-20 microns.

Figure 20:
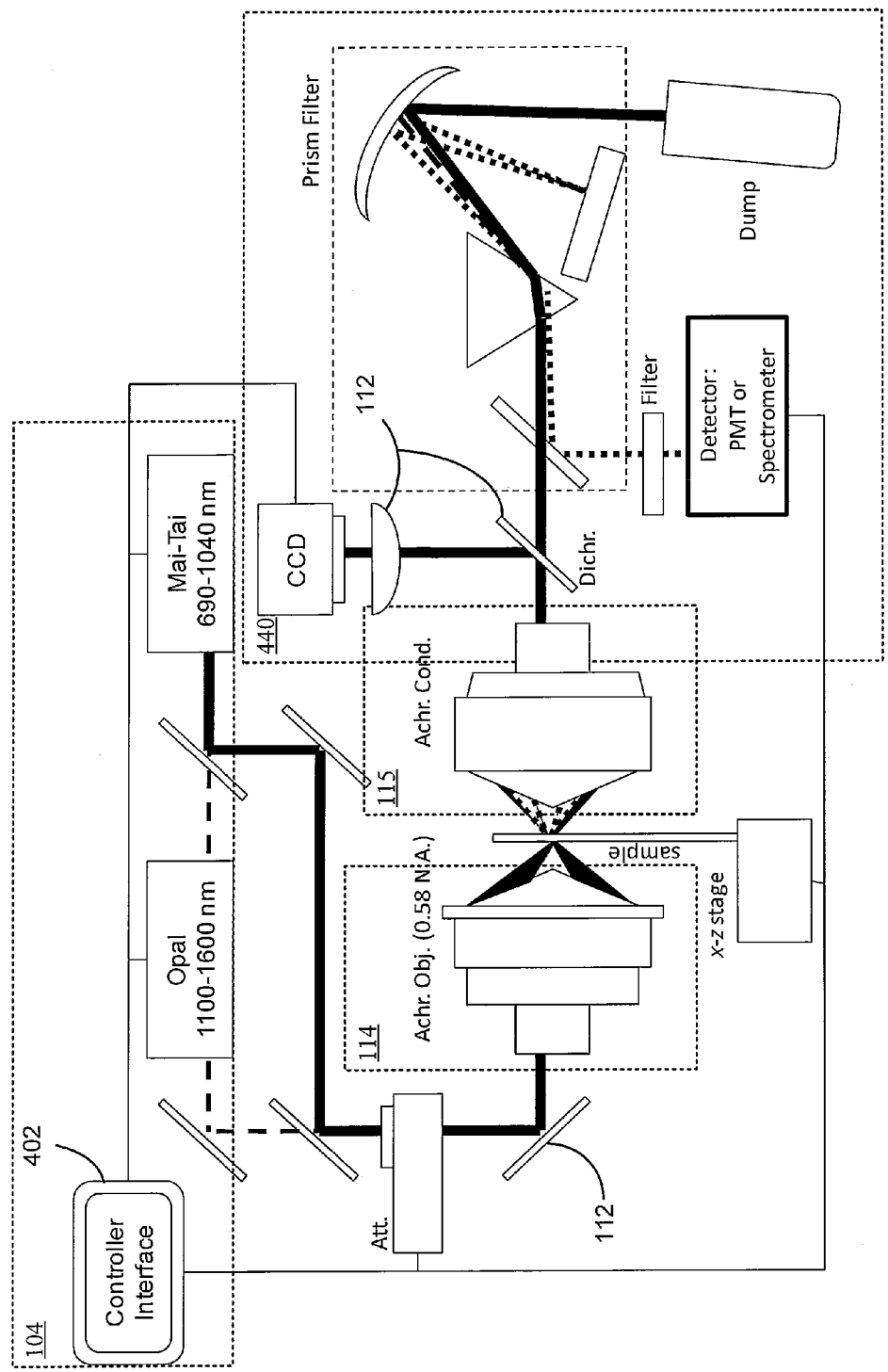
FIG. 20 is a perspective view of a monitor/treatment device configuration according to one illustrated embodiment.

The hemozoin thin-film was exposed to a pulsed electromagnetic energy stimulus to elicit a nonlinear optical response from the hemozoin nanoparticles using the experimental configuration outlined in FIG. 20. The experimental configuration provided for a pulsed electromagnetic energy stimulus in an overall range of 690 nm to 1600 nm using a Ti:Sapphire laser to scan wavelengths from 690-1040 nm and an optical parametric, oscillator (OPO). The quartz coverslip containing the hemozoin thin-film was attached to a nanoscale positioning stage to allow scanning of the sample along the optical axis (z-scan) and along the lateral surface (lateral scan). The sample was placed between an achromatic objective (0.58 numerical aperture) and an achromatic condenser. A prism and filtering system were used as a spatial filter to cover peak emission wavelengths ranging from 175 nm to 650 nm. Non-linear multi-harmonic response energy from the hemozoin particles was detected using either a spectrometer or a photomultiplier tube. Various components of the experimental configuration were linked to a controller interface (e.g., computer) including the Ti:Sapphire laser, the OPO, the detector, and the nanoscale positioning stage.

Figure 21B:
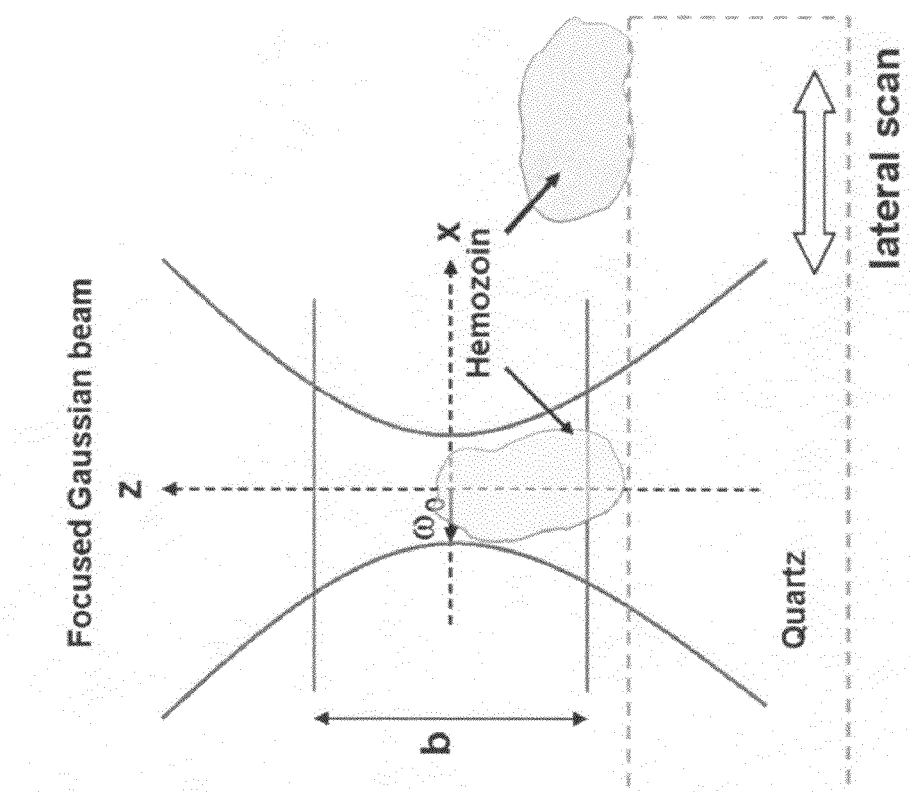
FIGS. 21A and 21B show top plan views of respective representative z-scan and lateral scans methodologies from hemozoin thin-films according to one illustrated embodiment.
Figure 21A:
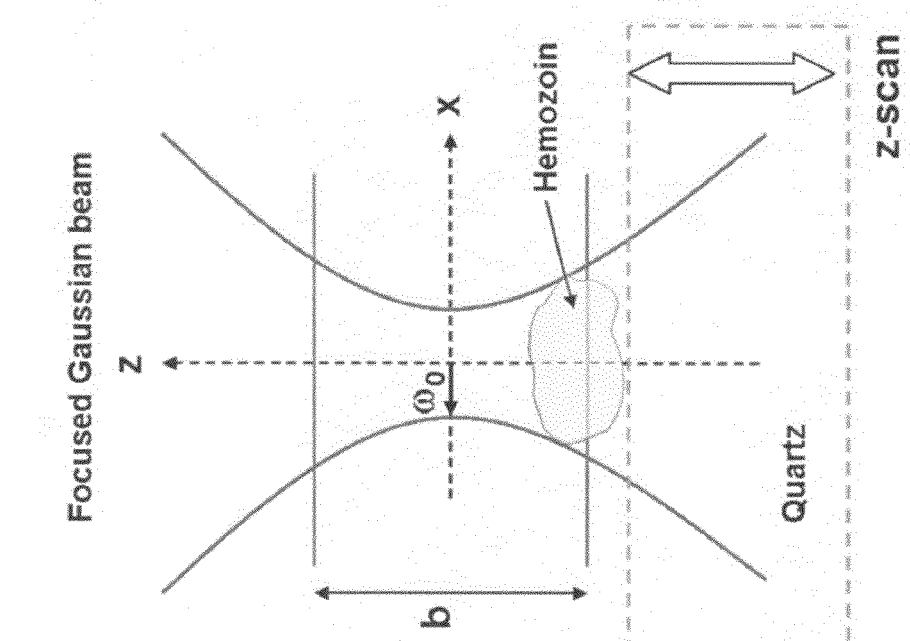
Figure 22:
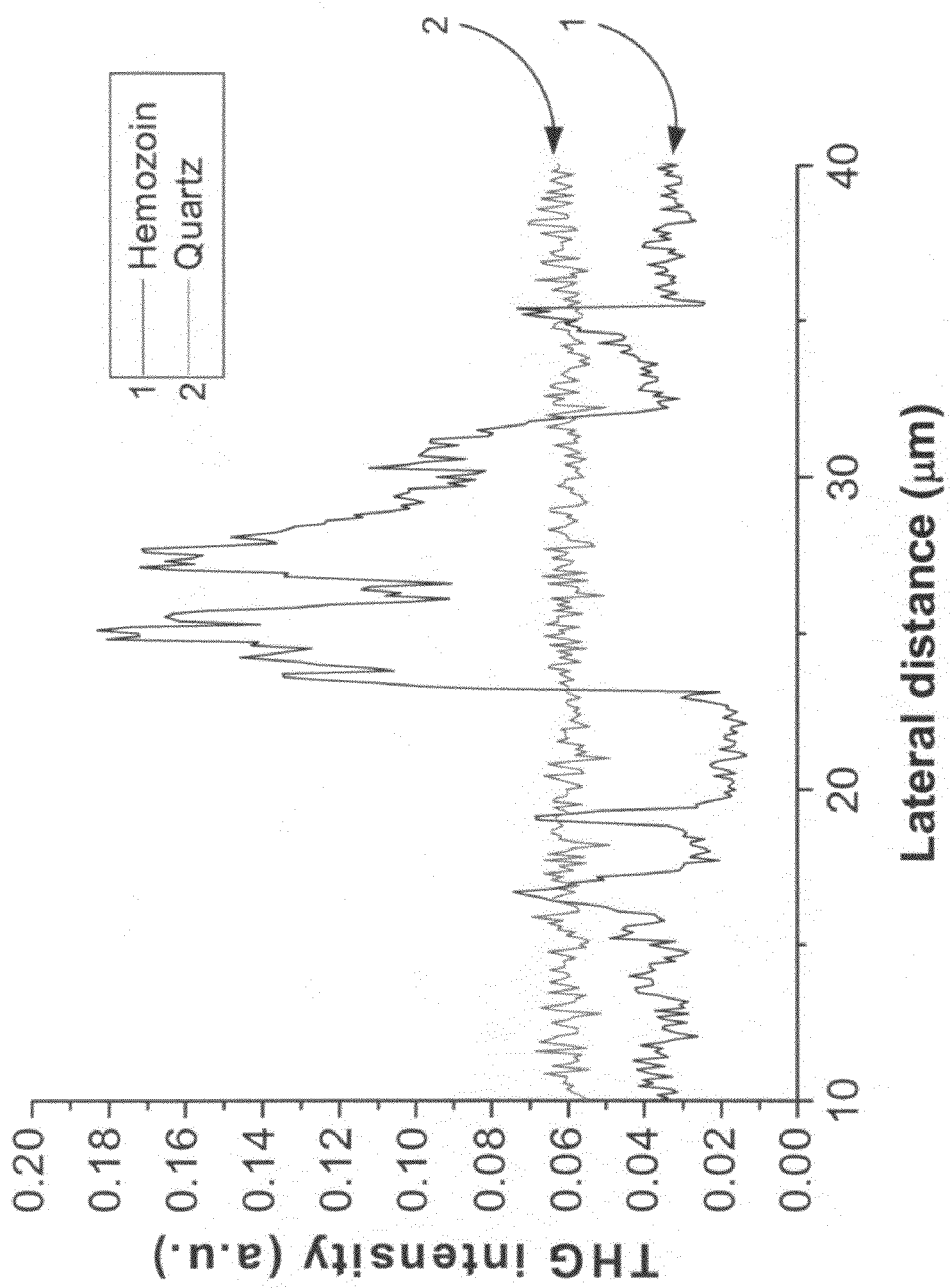
FIG. 22 Third Harmonic Generation (THG) Intensity vs. Lateral Distance plot of (1) hemozoin and (2) quartz according to one illustrated embodiment.
Figure 23:
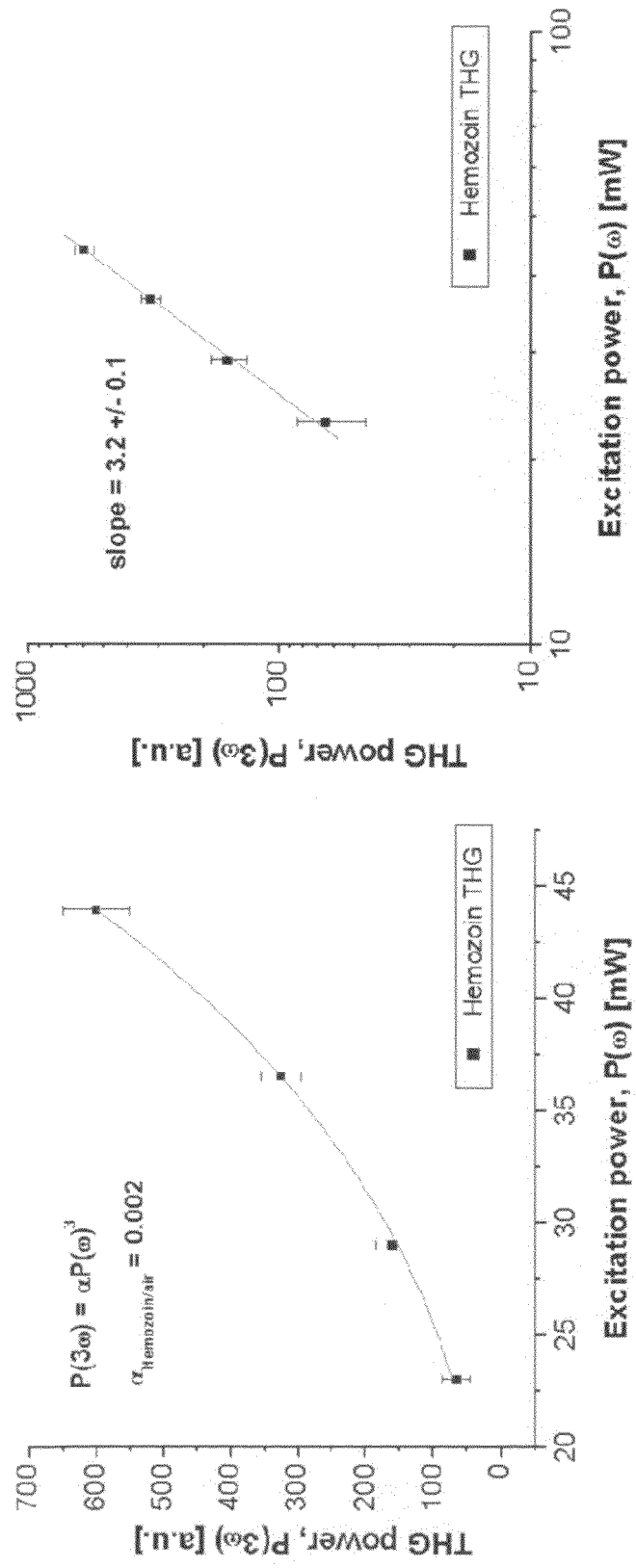
FIGS. 23A and 23B show Third Harmonic Generation (THG) Power vs. Excitation Power plots according to multiple illustrated embodiments.

In one set of experiments designed to measure a third harmonic response, the hemozoin thin-film was scanned along the optical axis (z-scan) and through the focal volume of an excitation energy of 810 nm. In this instance, a 100× objective with a 0.9 numerical aperture was used. The third harmonic response energy and excitation light were collimated, passed through a UG-11 colored glass filter (transmits wavelengths of 250-350 nm and of 700-800 nm) and a 265 nm notch filter and sent to a photomultiplier tube. The anode current from the photomultiplier tube was directly measured with an electrometer, linearly converted to a voltage, and recorded on a computer via a data acquisition card. FIG. 21A shows a representative z-scan from the hemozoin thin-film using this methodology. Also shown is the control measurement of the quartz substrate. The width of the peak in both cases was less than 5 μM, consistent with a beam size of less than 800 nm (based on 100× objective and 0.9 numerical aperture). The magnitude of the hemozoin peak varied up to 20% depending on the size of the hemozoin crystal and the amount of the focal volume filled with hemozoin. A lateral scan (FIG. 21B) was also performed using the parameters described above by first performing a z-scan analysis to find a maximum third harmonic response and a lateral scan was performed at this z-position. FIG. 22 shows an example of the third harmonic response through a lateral scan (1) of the hemozoin thin-film relative to a lateral scan (2) through the quartz substrate The third harmonic response efficiency is inversely proportional to the square of the spot size ($A_{spot}^2$) and the square of the pulse width ($\tau^2$) and therefore it is important to monitor and minimize both of these variables. The focal volume of the pulsed electromagnetic energy stimulus was profileld using a standard knife-edge diffraction technique to measure the beam waist at several positions along the optical axis. An autocorrelater was used to measure the pulse-width of the beam. The third order dependence on power output from the pulsed electromagnetic energy stimulus was demonstrated by plotting the laser excitation power, $P(\omega)$[mW] against the third harmonic response power, $P(3\omega)$ [arbitrary units] as shown in FIG. 23. A log-log scale plot of this data generated a line with a slope of approximately 3.

The herein described subject matter sometimes illustrates different components contained within, or connected with, different other components. It is to be understood that such depicted architectures are merely examples, and that in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

FIGS. 23A and 23B show $3^{rd}$ order power dependence of hemozoin plotted on (FIG. 23A linear and (FIG. 23A) log-log scale.

Figure 24:
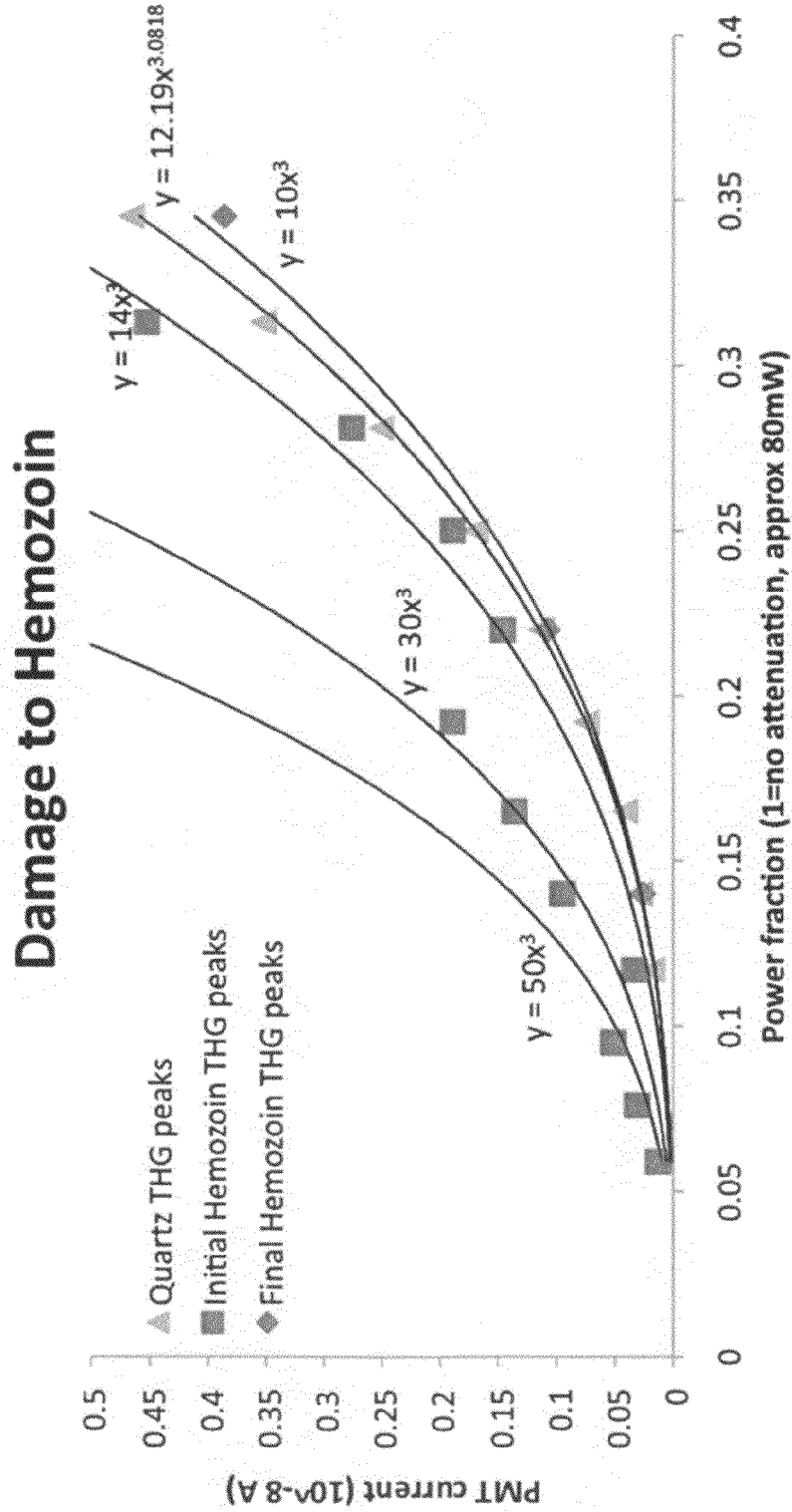
FIG. 24 is a Photo Multiplier Tube (PMT) current vs. Power Fraction plot according to one illustrated embodiment.

FIG. 24 shows a $3^{rd}$ order dependence of hemozoin on incident power.

Figure 25:
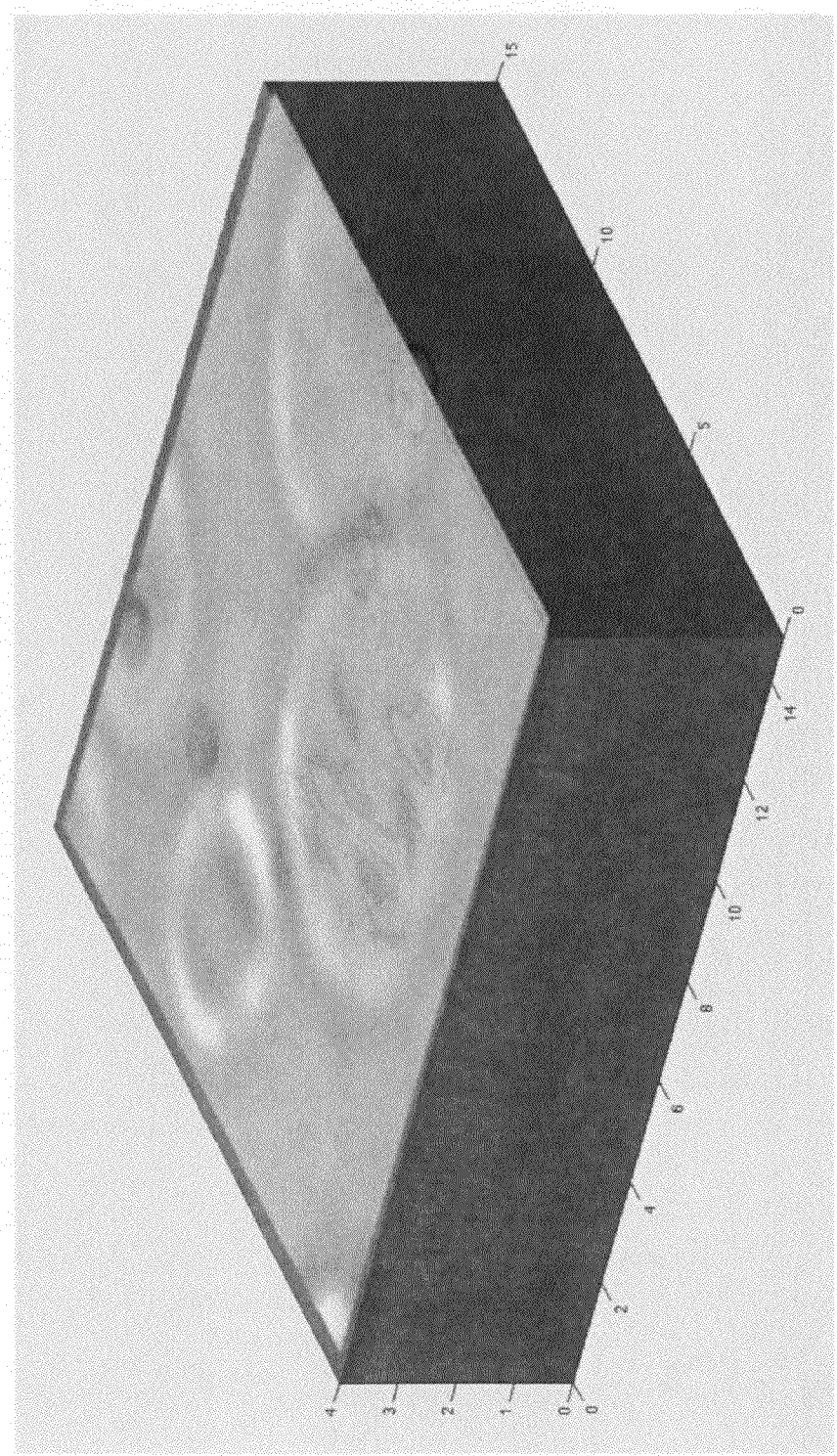
FIG. 25 is a voxel image of hemozoin crystals in infected red blood cells according to one illustrated embodiment.

FIG. 25 is a voxel image of hemozoin crystals 2502 in infected red blood cells 2504.

Figure 26:
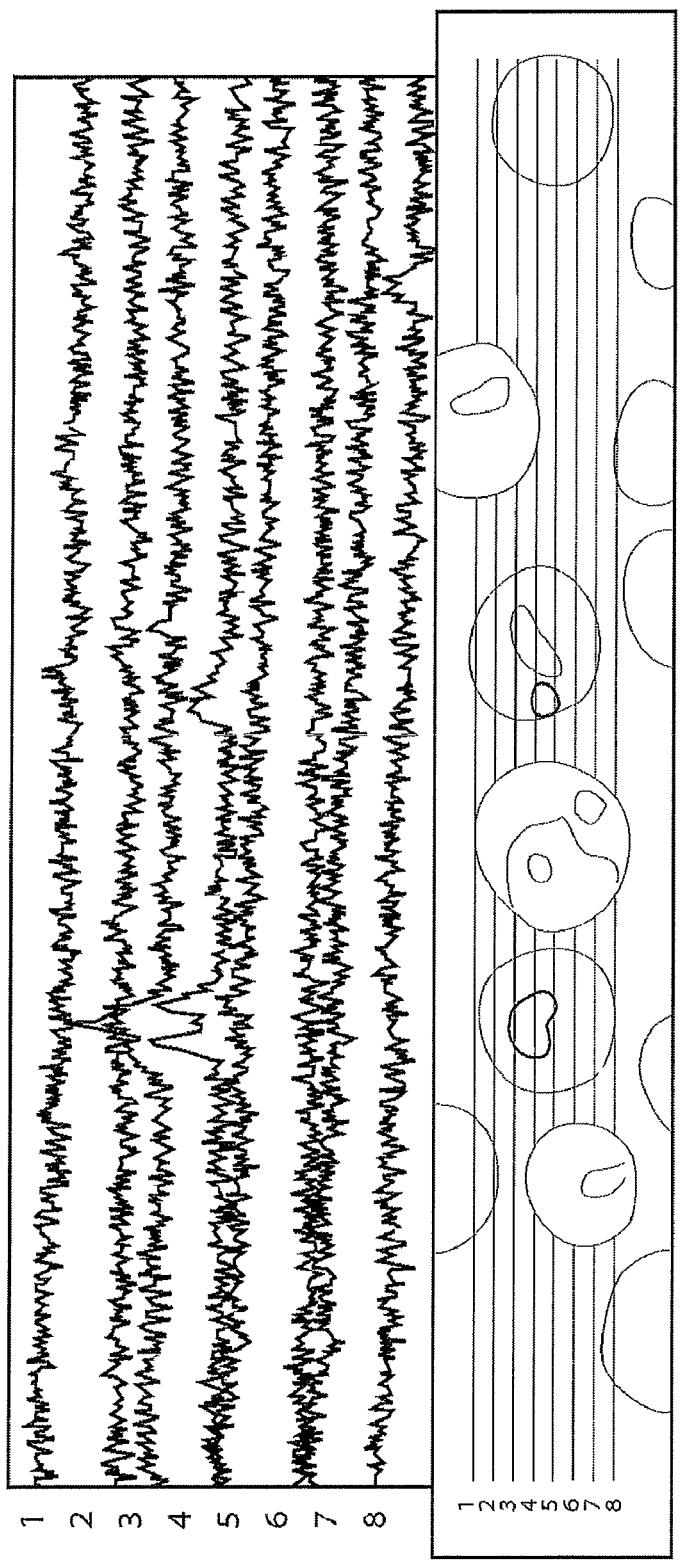
FIG. 26 is a two-dimensional spatial scan of infected and uninfected erythrocytes showing intensity peaks that correspond to hemozoin crystals in the infected cells, according to one illustrated embodiment.

FIG. 26 shows a two-dimensional spatial scan of infected and uninfected erythrocytes showing intensity peaks that correspond to hemozoin crystals in the infected cells.

Figure 27:
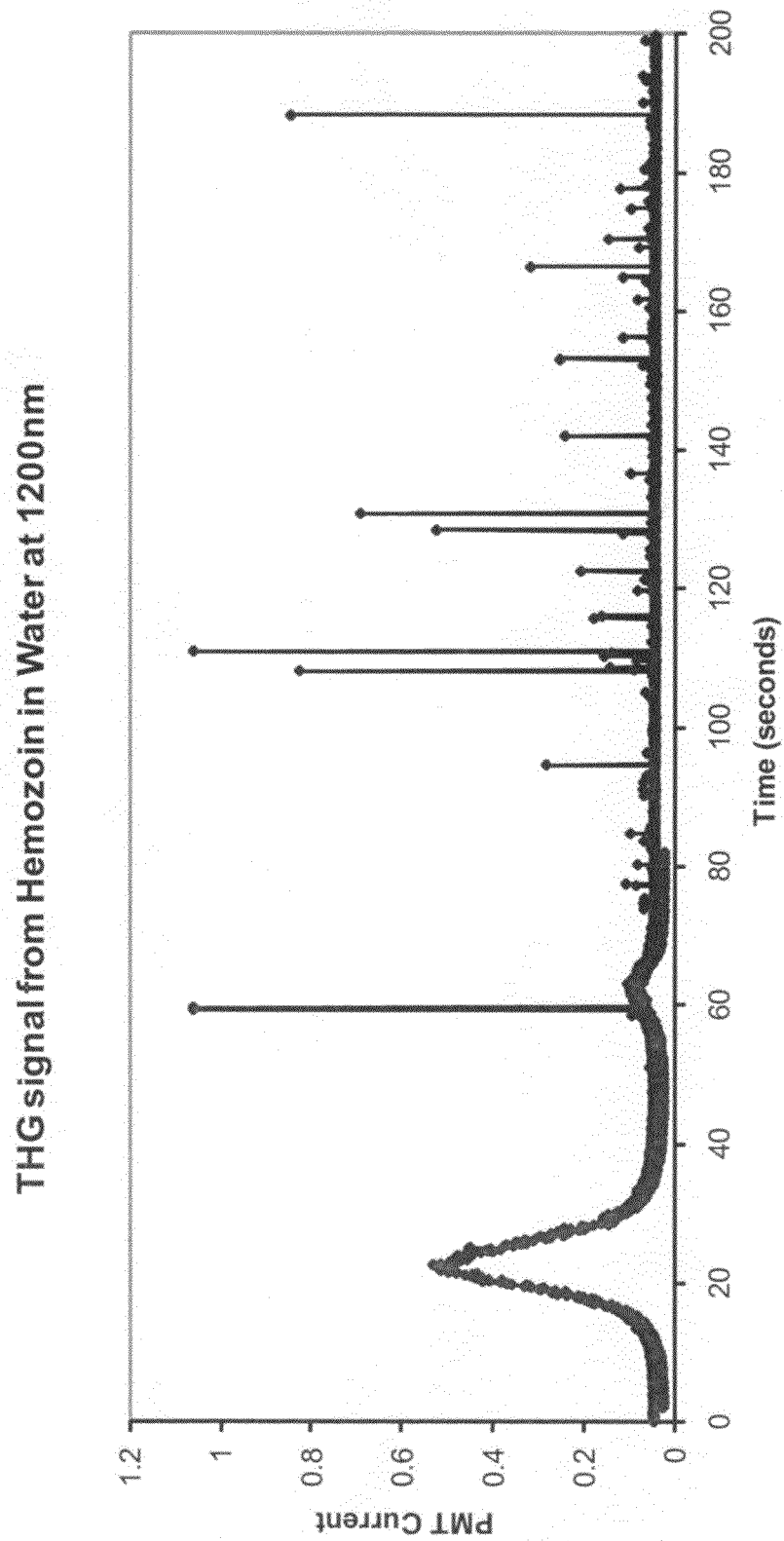
FIG. 27 is a Photo Multiplier Tube (PMT) current vs. Time plot according to one illustrated embodiment.

FIG. 27 shows Third Harmonic Generation (THG) signal from hemozoin nanoparticles suspended in water.

Figure 28:
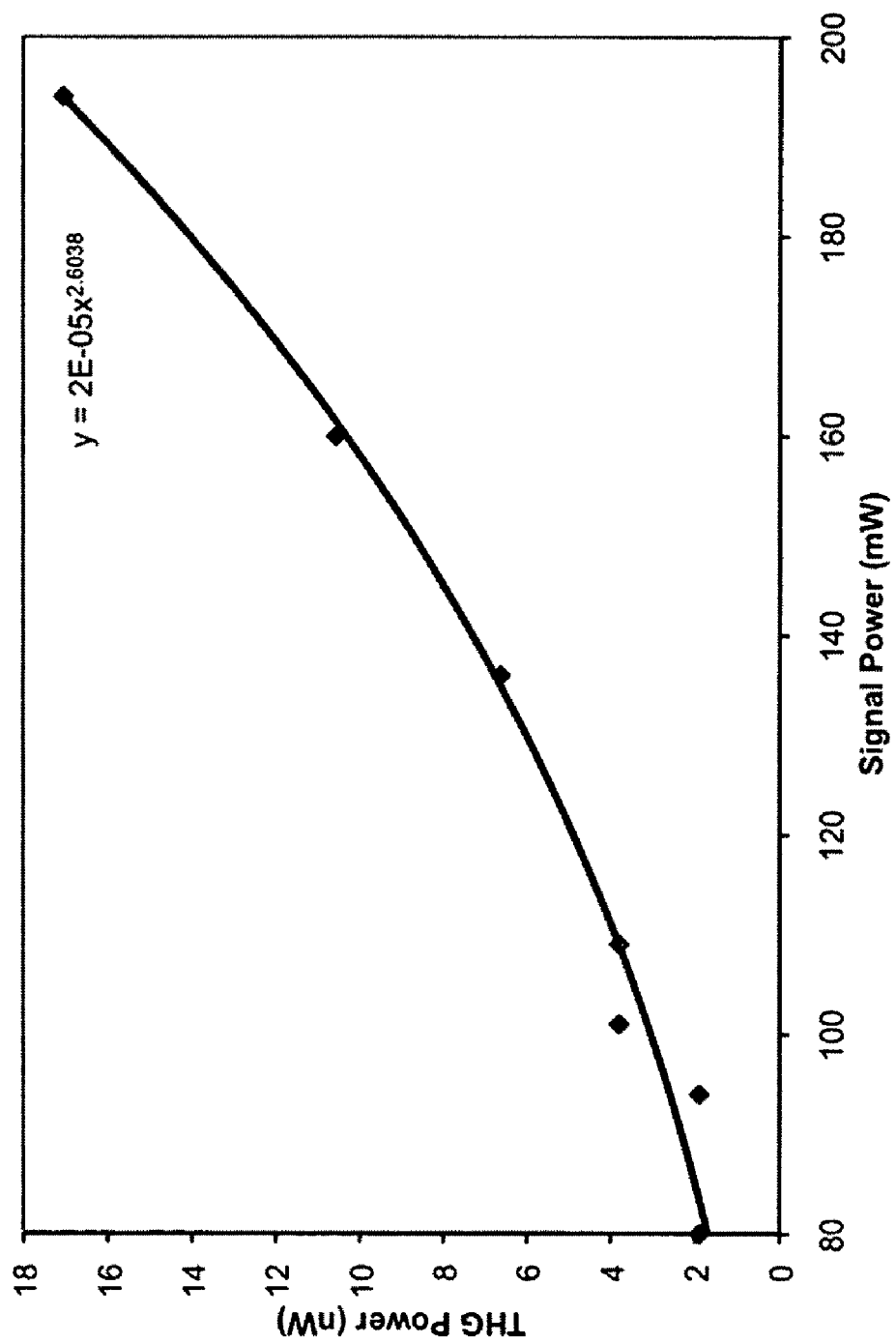
FIG. 28 is a Third Harmonic Generation (THG) vs. Signal Power plot according to one illustrated embodiment.

FIG. 28 shows the absolute Third Harmonic Generation (THG) power from hemozoin showing $3^{rd}$ order dependence.

Figure 29:
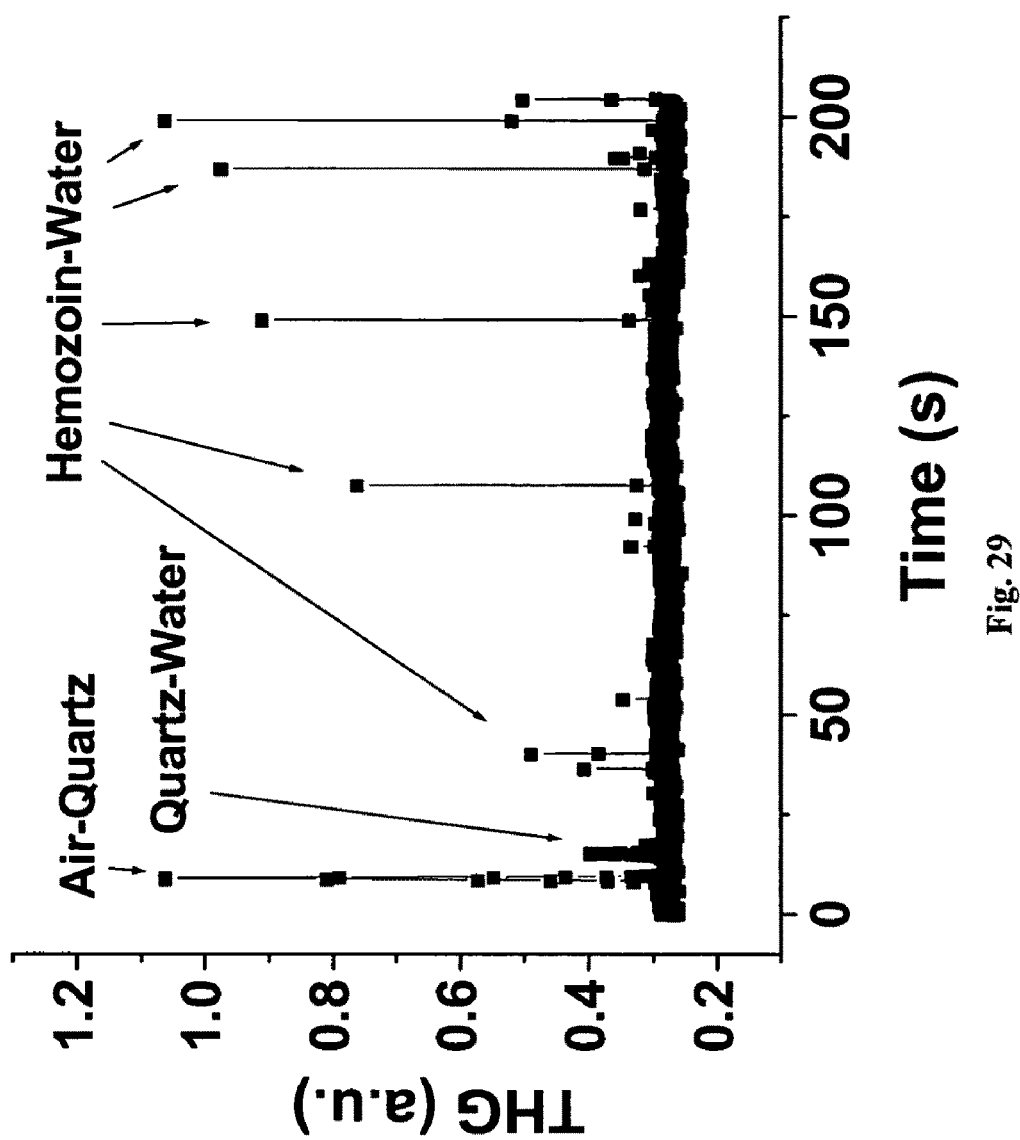
FIG. 29 is a Third Harmonic Generation (THG) vs. Time plot according to one illustrated embodiment.

FIG. 29 Shows Hemozoin-water Third Harmonic Generation (THG) intensity.

Figure 30:
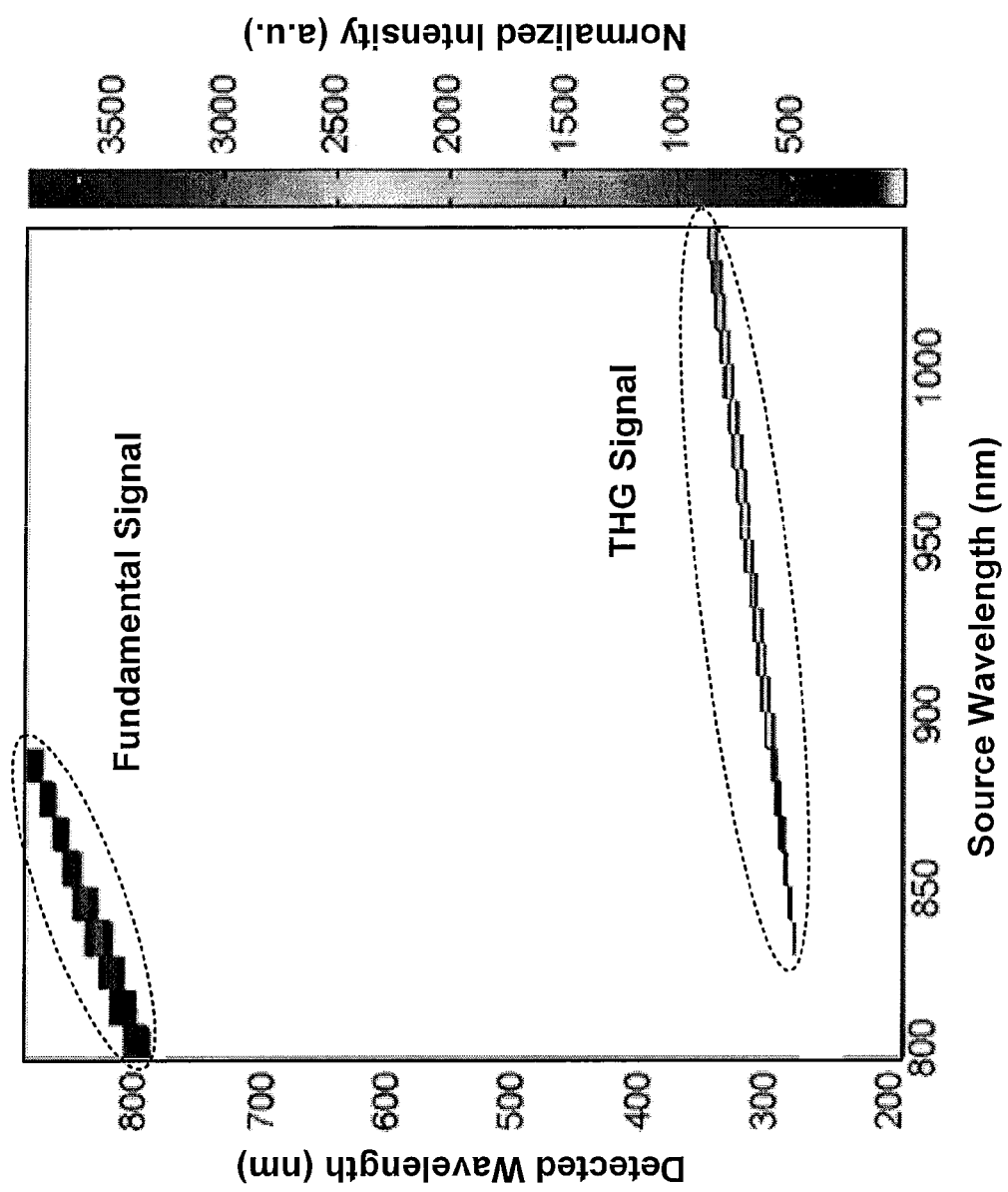
FIG. 30 is a Detected Wavelength vs. Source Wavelength plot according to one illustrated embodiment.

FIG. 30 shows a two-dimensional plot of Third Harmonic Generation (THG) signal as a function of source and detected wavelength.

FIG. 31A show a monitor/treatment device according to one illustrated embodiment.

FIG. 31B an example of a monitor/treatment device using an epi-detection setup.

Figure 32A:
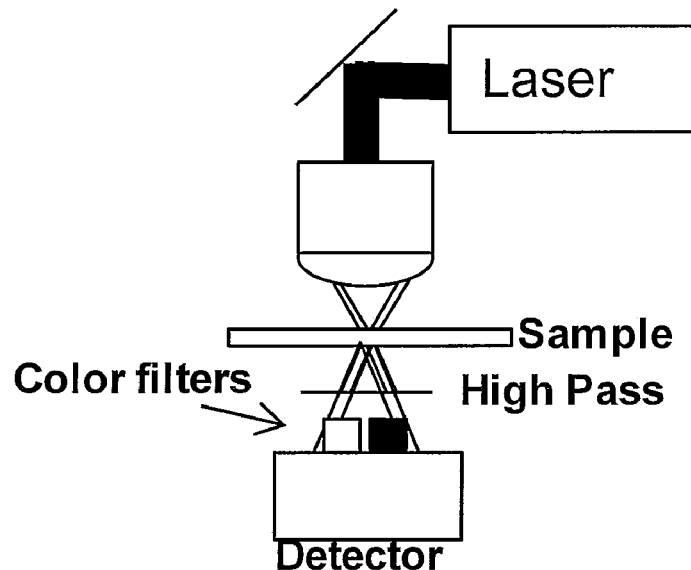
FIG. 32A is a prospective view of a monitor/treatment device using Third Harmonic Generation (THG) detection according to one illustrated embodiment.

FIG. 32A shows an example of a monitor/treatment device using a Third Harmonic Generation (THG) detection setup.

Figure 32B:
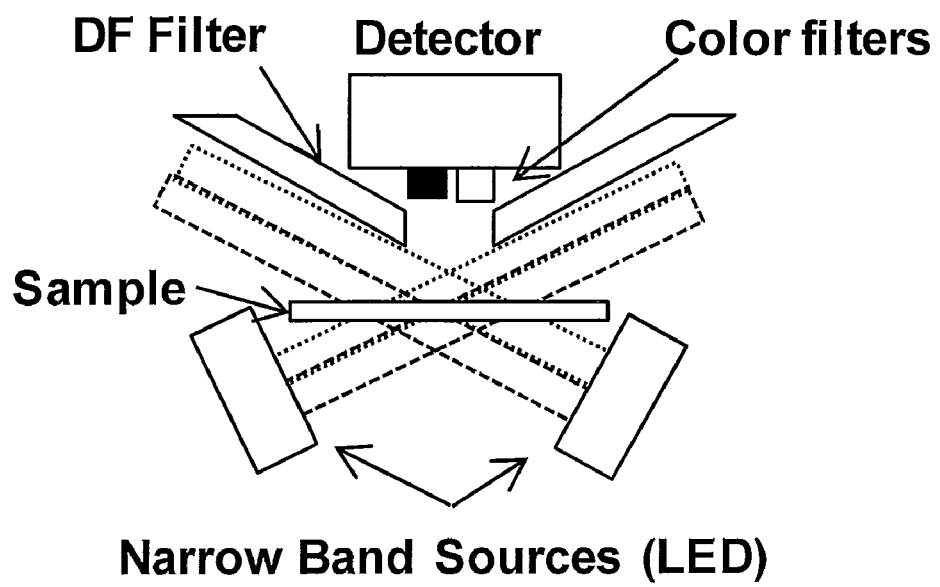
FIG. 32B is a prospective view of a monitor/treatment device using Dark-field detection according to one illustrated embodiment.

FIG. 32B shows an example of a monitor/treatment device using Dark-field detection according to one illustrated embodiment.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors 404 (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transceiver, transmission logic, reception logic, etc.), etc.).

While particular aspects of the present subject matter described herein have been shown and described, it will be apparent to the reader that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless Context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A system, comprising:
   circuitry configured to detect a scattered energy from a biological tissue in at least one of a dark-field detection configuration and a Rheinberg detection configuration; and
   circuitry configured to magnetically perturb hemozoin nanoparticles in the biological tissue in response to a comparison between detected scattered energy information and reference hemozoin nanoparticles scattered energy information;
   wherein the circuitry configured to magnetically perturb hemozoin nanoparticles in a biological tissue includes one or more processors that, when activated, generate a control signal that causes the comparison between the detected scattered energy and the reference hemozoin nanoparticles scattered energy information.

2. The system of claim 1, further comprising:
   circuitry configured to impart an effective amount of an electromagnetic energy stimulus in a dark-field configuration onto one or more regions of the biological tissue to produce scattered energy from the biological tissue.

3. The system of claim 2, wherein the circuitry configured to impart the effective amount of an electromagnetic energy stimulus includes a lens array assembly configured to focus one or more incident electromagnetic energy stimuli onto the biological subject and to receive scattered energy therefrom.

4. The system of claim 1, wherein the circuitry configured to detect the scattered energy includes at least one sensor configured to receive a portion of the scattered energy in a dark-field detection configuration.

5. The system of claim 1, wherein the circuitry configured to detect the scattered energy includes at least one sensor configured to receive a portion of the scattered energy in a Rheinberg detection configuration.

6. The system of claim 1, wherein the circuitry configured to detect the scattered energy includes a lens array assembly configured receive at least a portion of the scattered energy from a biological subject.

7. The system of claim 1, wherein the circuitry configured to detect the scattered energy includes a Rheinberg differential color illumination assembly configured receive at least a portion of the scattered energy from the biological subject.

8. The system of claim 1, wherein the circuitry configured to detect the scattered energy includes at least one Rheinberg filter.

9. The system of claim 1, wherein the circuitry configured to magnetically perturb hemozoin nanoparticles in a biological tissue includes a coil assembly configured to magnetically induce at least one of an oscillation, a translation, and a rotation of hemozoin nanoparticles in a biological tissue.

10. The system of claim 1, wherein the circuitry configured to magnetically perturb hemozoin nanoparticles in a biological tissue includes one or more conductive traces configured to cause at least one of an oscillation, a translation, and a rotation of hemozoin nanoparticles in a biological tissue.

* * * * *

UNITED STATES PATENT AND TRADEMARK OFFICE
CERTIFICATE OF CORRECTION

PATENT NO. : 8,388,509 B2
APPLICATION NO. : 12/658589
DATED : March 5, 2013
INVENTOR(S) : Hegg et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this
Twentieth Day of August, 2013

Teresa Stanek Rea
*Acting Director of the United States Patent and Trademark Office*